US011280745B2

(12) United States Patent
MacDonald et al.

(10) Patent No.: US 11,280,745 B2
(45) Date of Patent: Mar. 22, 2022

(54) RESONANT SENSING DEVICE

(71) Applicant: Mezent Corporation, Westlake Village, CA (US)

(72) Inventors: Perry Allen MacDonald, Newbury Park, CA (US); Daniel Joseph Denninghoff, Thousand Oaks, CA (US)

(73) Assignee: Mezent Corporation, Newbury Park, CA (US)

( * ) Notice: Subject to any disclaimer, the term of this patent is extended or adjusted under 35 U.S.C. 154(b) by 254 days.

(21) Appl. No.: 16/503,544

(22) Filed: Jul. 4, 2019

(65) Prior Publication Data

US 2020/0011811 A1    Jan. 9, 2020

Related U.S. Application Data

(60) Provisional application No. 62/836,650, filed on Apr. 20, 2019, provisional application No. 62/694,073, filed on Jul. 5, 2018.

(51) Int. Cl.
| | | |
|---|---|---|
| *G01N 22/00* | (2006.01) | |
| *H04B 1/00* | (2006.01) | |
| *G01R 1/00* | (2006.01) | |

(52) U.S. Cl.
CPC .................... *G01N 22/00* (2013.01)

(58) Field of Classification Search
CPC ....... H04B 1/00; H04B 2201/00; H01L 21/00; H01P 1/00; H01Q 1/00; G01R 1/00
See application file for complete search history.

(56) References Cited

U.S. PATENT DOCUMENTS

| | | |
|---|---|---|
| 7,223,608 B2 | 5/2007 | Gopalsami et al. |
| 7,263,398 B2 | 8/2007 | Carr |
| 7,518,472 B2 | 4/2009 | Mukaiyama et al. |
| 10,092,225 B2 | 10/2018 | Bharj |
| 2006/0025664 A1 | 2/2006 | Kim et al. |
| 2007/0203405 A1 | 8/2007 | Shimomura |
| 2007/0235184 A1 | 10/2007 | Thompson et al. |
| 2008/0024133 A1 | 1/2008 | Vaughan et al. |
| 2008/0142828 A1 | 6/2008 | Yang |
| 2008/0200790 A1 | 8/2008 | Kim et al. |
| 2008/0224922 A1 | 9/2008 | Cleland et al. |

(Continued)

FOREIGN PATENT DOCUMENTS

| | | |
|---|---|---|
| JP | 6504504 B2 | 4/2019 |
| KR | 1020110043918 A | 4/2011 |
| WO | 2018129122 A2 | 7/2018 |

OTHER PUBLICATIONS

Roy, Subhanwit, "Microwave resonant sensor for measurement of ionic concentration in aqueous solutions." 125 pages, 2017.

(Continued)

*Primary Examiner* — Jermele M Hollington
*Assistant Examiner* — Temilade S Rhodes-Vivour

(57) ABSTRACT

A sensing device can use electromagnetic resonance to detect properties of a sample. For example, the sensing device can be immersed into a sample, placed in proximity to a sample, or otherwise located within sensing range of a sample. The sensing device can transmit a signal onto the sample and receive a reflected signal using a resonating structure. The sensing device can analyze the reflected signal to detect a constituent in the sample, such as a concentration of the constituent in the sample.

22 Claims, 29 Drawing Sheets

(56) References Cited

U.S. PATENT DOCUMENTS

| | | | |
|---|---|---|---|
| 2008/0289403 | A1 | 11/2008 | Palacios Donaque |
| 2010/0244992 | A1 | 9/2010 | Kasashima et al. |
| 2012/0150000 | A1 | 6/2012 | Al-Shamma'a et al. |
| 2014/0090454 | A1 | 4/2014 | Surman et al. |
| 2016/0051171 | A1 | 2/2016 | Pikov et al. |
| 2016/0084761 | A1* | 3/2016 | Rothberg ............. C12Q 1/6874 506/4 |
| 2016/0315661 | A1* | 10/2016 | Henry ................... G01R 31/44 |
| 2016/0344240 | A1* | 11/2016 | Yeh ....................... A61N 1/3605 |
| 2017/0053737 | A1* | 2/2017 | Kurs .................. H01F 27/2823 |
| 2017/0082083 | A1 | 3/2017 | Lowery et al. |
| 2018/0115082 | A1* | 4/2018 | Johnson ................ H01Q 15/14 |
| 2018/0166761 | A1* | 6/2018 | Henry ................ H04B 17/3911 |

OTHER PUBLICATIONS

Lin, Tamar, et al., "Non-invasive Glucose Monitoring: A Review of Challenges and Recent Advances," Current Trends in Biomedical Engineering & Biosciences, Juniper, vol. 6, Issue 5, 8 pages, Jul. 2017.

Siegel, Peter, et al., "First Millimeter-wave Animal In Vivo Measurements of L-glucose and D-glucose: Further Steps Towards a Non-invasive Glucometer," 41st IEEE Int. Conf. on Infrared, Millimeter, and THz Waves (IRMMW-THz), Copenhagen, Denmark, 3 pages, Sep. 2016.

Siegel, Peter, et al., "Compact Non-invasive Millimeter-wave Glucose Sensor," 40th IEEE Int. Conf, on Infrared, Millimeter, and THz Waves (IRMMW-THz), Hong Kong, China, 3 pages, Aug. 2015.

Siegel, Peter, et al., "Millimeter-wave Non-invasive Monitoring of Glucose in Anesthetized Rats," 39th IEEE Int. Conf. on Infrared, Millimeter, and THz Waves (IRMMW-THz), Tucson, AZ, 2 pages, Sep. 2014.

Keysight Technologies, Inc., N1501A Dielectric Probe Kit 10 MHz to 50 GHz, Online: https://literature.cdn.keysight.com/litweb/pdf/5992-0264EN.pdf?id=2605692.

Glucose Meter [online], [retrieved Sep. 13, 2019], Retrieved from the Internet: <URL: https://en.wikipedia.org/wiki/Glucose_meter>, 8 pages.

Boybay, Muhammed, et al., "Material Characterization Using Complementary Split-Ring Resonators," IEEE Transactions on Instrumentation and Measurement, vol. 61, No. 11, pp. 3039-3046, Nov. 2012.

Lee, Dong-Kyu, et al., "Highly sensitive and selective sugar detection by terahertz nano-antennas," Nature, Scientific Reports, vol. 5, pp. 154-159, Oct. 23, 2015.

Olivo, Jacopo, et al., "Glucose and Lactate Monitoring in Cell Cultures with a Wireless Android Interface," 2014 IEEE Biomedical Circuits and Systems Conference (BioCAS) Proceedings, Lausanne, 2014, pp. 400-403.

Athey, T. et al., "Measurement of Radio Frequency Permittivity of Biological Tissues with an Open-ended Coaxial Line: Part I," IEEE Transactions on Microwave Theory and Techniques, vol. 30, No. 1, pp. 87-92, Jan. 1982.

Stuchly, M. et al., "Measurement of Radio Frequency Permittivity of Biological Tissues with an Open-ended Coaxial Line: Part II-Experimental Results," IEEE Transactions on Microwave Theory and Techniques, vol. MTT-30, No. 1, Jan. 1982.

Glucosewise [online], [retrieved on Sep. 20, 2019]. Retrieved from the Internet:<URL: http://gluco-wise.com/beta/>, 7 pages.

Glucotrack, Model DF-F, Integrity Applications, Inc. [online], [retrieved Sep. 20, 2019]. Retrieved from the Internet: <URL: http://www.glucotrack.com/about-glucotrack/>, 4 pages.

Single-use Bioprocessing, Thermo Fisher Scientific, Inc. [online], [retrieved on Sep. 20, 2019]. Retrieved from the Internet: <URL: https://www.thermofisher.com/us/en/home/life-science/bioproduction/single-use-bioprocessing.html>, 3 pages.

Integrity Applications [online], [retrieved on Sep. 25, 2019], Retrieved from the Internet:< URL: http://www.integrity-app.com>, 3 pages.

International Search Report dated Oct. 25, 2019 for PCT/US2019/040659, 4 pages.

Written Opinion of ISA dated Oct. 25, 2019 for PCT/US2019/040659, 6 pages.

\* cited by examiner

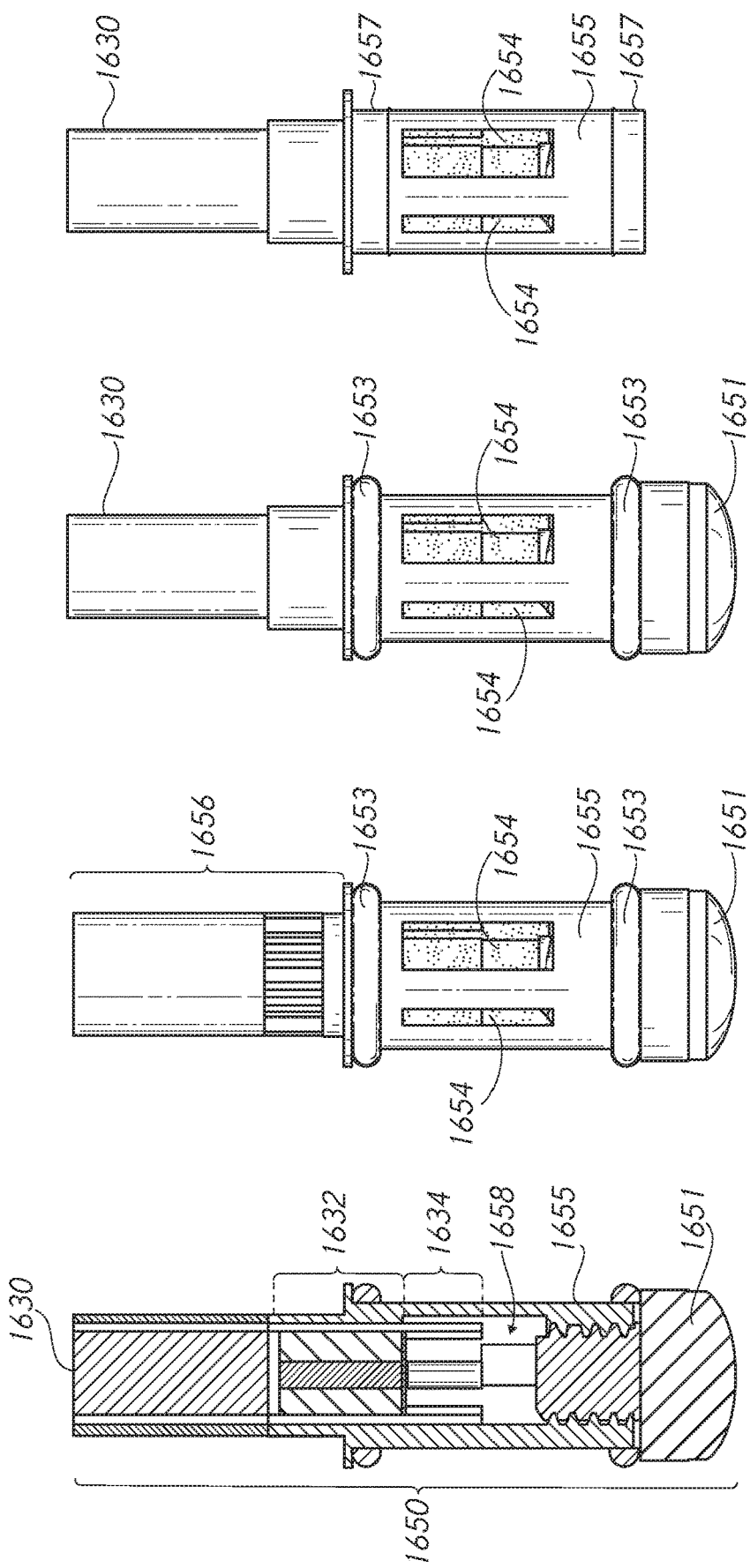

RESONANT SENSING DEVICE

CROSS-REFERENCE TO RELATED APPLICATIONS

This application claims priority to U.S. Provisional Application No. 62/694,073, filed Jul. 5, 2018, and entitled IMMERSION PROBE SENSING DEVICE AND METHOD, and to U.S. Provisional Application No. 62/836,650, filed Apr. 20, 2019, and entitled IMMERSION PROBE SENSING DEVICE AND METHOD, the disclosures of which are hereby incorporated by reference in their entirety.

BACKGROUND

Field

The present disclosure relates to the field of sensor devices.

Description of the Related Art

Information relating to the concentration and/or presence of constituents in sample media, including biological elements and/or compounds can be useful for various purposes. Sensor devices and systems can have various structures and functionality.

SUMMARY

Described herein are one or more methods and/or devices for detecting properties of a sample and/or one or more constituents thereof using electromagnetic resonance.

In some implementations, the present disclosure relates to a sensing system comprising a sensor and control circuitry electrically coupled to the sensor. The sensor includes a transmitting portion including a first outer conductor portion and a dielectric material disposed at least partially within the first outer conductor portion and a resonating portion including a second outer conductor portion that forms a resonator cavity. The control circuitry is configured to transmit a first signal using the sensor, receive a first reflected signal using the resonator portion of the sensor, determine a resonant frequency associated with the resonating portion based at least in part on the reflected signal.

The control circuitry can be further configured to determine a concentration of a constituent in a sample based at least in part on the resonant frequency. The control circuitry can be further configured to transmit a second signal using the sensor, receive a second reflected signal using the resonator portion of the sensor, and determine the resonant frequency based at least in part on the first reflected signal and the second reflected signal. In some embodiments, the control circuitry is configured to determine the resonant frequency based on one or more of an amplitude of the first reflected signal and a phase of the first reflected signal.

In some embodiments, the transmitting portion is proximate to the control circuitry and the resonating portion is distal to the control circuitry. The sensing system can further comprise a container structure configured to receive the sensor, wherein the container structure includes an opening and a semi-permeable membrane associated with the opening. In some embodiments, the sensing system further comprises an interface configured to communicate data based on at least one of the signal, the reflected signal, the resonant frequency to a computing device that is communicatively coupled to the interface.

In some implementations, the present disclosure relates to a sensor. The sensor comprises a proximal elongate transmitting portion and a distal resonating portion. The proximal elongate transmitting portion includes a first outer conductor portion and an interior portion defined at least in part by the first outer conductor portion. The distal resonating portion includes a second outer conductor portion that forms a resonator cavity. The resonator cavity can be fluidly isolated from the interior of the transmitting portion.

In some embodiments, the sensor further comprises an electrically absorptive material disposed at an interface between the interior portion of the proximal elongate transmitting portion and the resonator cavity of the distal resonating portion. The sensor has an elongated form and further comprises an inner conductor that extends along a center axis of the sensor. In some embodiments, the absorptive material is disposed between the first outer conductor portion and the inner conductor. The inner conductor can extend through the proximal elongate transmitting portion and the distal resonating portion.

In some embodiments, the first outer conductor portion and the second outer conductor portion are portions of a single unitary outer conductor form. The second outer conductor portion can include at least one slot. In some embodiments, the at least one slot extends axially from a distal end of the distal resonating portion. The sensor can have any shape or form, such as a cylindrical elongated form.

In some implementations, the present disclosure relates to a sensor. The sensor comprises a transmitting portion and a resonating portion. The transmitting portion includes a first outer conductor portion, a dielectric material disposed at least partially within an interior of the transmitting portion formed at least in part by the first outer conductor portion, and an interface configured to electrically couple to control circuitry. The resonating portion includes a second outer conductor portion that forms a resonator cavity. The resonator cavity is fluidly isolated from the interior of the transmitting portion.

In some embodiments, the transmitting portion has a structure that conforms to one or more of a microstrip transmission line structure, a stripline transmission line structure, and a coplanar waveguide transmission line structure. The sensor can have any shape or form, such as an elongated form, wherein a transverse cross-section of the sensor has a substantially rectangular shape.

In some implementations, the present disclosure relates to a method of using a sensor. The method comprises providing a volume of sample media, transmitting, using the sensor, a signal onto a sample, receiving, using a resonating portion of the sensor, a reflected signal, and determining, by control circuitry that is coupled to the sensor, a resonant frequency associated with the sample based at least in part on the reflected signal. The sensor can include a transmitting portion and the resonating portion. The transmitting portion can include a dielectric material and the resonating portion can include a cavity.

In some embodiments, the transmitting includes transmitting multiple signals having different frequencies, the receiving includes receiving multiple reflected signals, and the determining includes determining the resonant frequency based at least in part on the multiple reflected signals. The method can further comprise determining, by the control circuitry, a concentration of a constituent in the sample based at least in part on the resonant frequency.

For purposes of summarizing the disclosure, certain aspects, advantages and novel features have been described.

It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIG. 15-1 illustrates an example system with a sensing system implemented at least in part with a circuit board(s).

FIG. 15-2 illustrates another example system with a sensing system implemented at least in part with a circuit board(s).

FIG. 16A illustrates a cross-sectional view of an example membrane structure and sensor.

FIG. 16B illustrates the membrane structure and sensor of FIG. 16A.

FIG. 16C illustrates the membrane structure and sensor of FIG. 16A with the cylinder-shaped shrinkable encasing material removed.

FIG. 16D illustrates the membrane structure and the sensor of FIG. 16A with the cylinder-shaped shrinkable encasing material, the cap, and the elastic securing rings removed.

DETAILED DESCRIPTION

Figure 1:
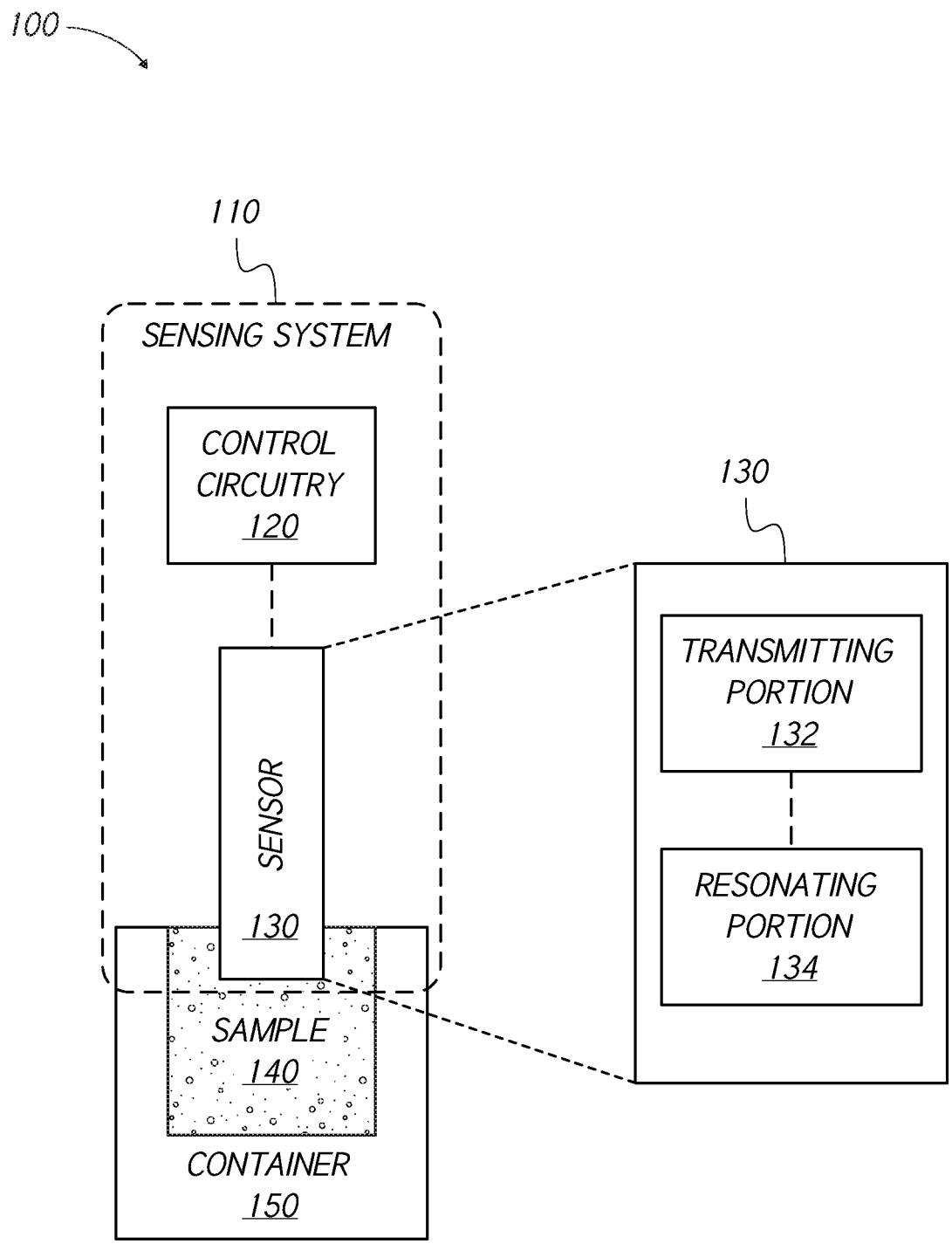
FIG. 1 illustrates an example system that includes a sensing device and/or system configured to detect a constituent in a sample in accordance with one or more embodiments of the present disclosure.

The headings provided herein are for convenience only and do not necessarily affect the scope or meaning of the claimed inventive subject matter. The present disclosure relates to systems, devices, and methods for detecting properties of a sample and/or one or more constituents thereof using electromagnetic resonance.

Although certain preferred embodiments and examples are disclosed below, inventive subject matter extends beyond the specifically disclosed embodiments to other alternative embodiments and/or uses, and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Electromagnetic signals or waves can be used to detect and sense the presence of biological compounds, such as glucose, in biological tissue and other media in accordance with various processes and techniques. For example, in some implementations, electromagnetic signals are transmitted through biological tissue or other media on one side of the tissue/media and detected on the opposite side of the tissue/media. A comparison between the known input signals and the measured output signals can be used to determine the concentration of the target biological constituent. However, transmission and detection of signals through tissue/media can be difficult or untenable in some situations. For example, with respect to signal transmission through human tissue, relatively few tissue locations may be available that have suitable tissue thickness and/or sample (e.g., blood) concentration characteristics for adequate constituent detection.

In some implementations, a needle probe is inserted into tissue or other media, wherein the needle is used to transmit electromagnetic signals within the tissue/media to detect the concentration of the target biological constituent. In some implementations, human skin is punctured to cause bleeding to produce a sample of blood that can be directly accessed and tested using, for example, a disposable test strip. For example, a disposable test strip can be placed into a meter device to measure a level of a target constituent, such as glucose, in the blood. However, implementing needle puncture and/or other bleeding inducement can be painful and/or potentially damaging to the patient. Furthermore, contamination of an extracted sample can occur that materially impacts the accuracy of any associated measurements.

Certain solutions utilize a biological reactor to grow cells in a solution that includes, for example, glucose and/or other target constituent(s). In order to maintain the glucose at an appropriate level, a portion of the solution can be removed from the biological reactor periodically (e.g., once a day) and measured in a machine. Such machines can often be very expensive, costing a hundred thousand dollars or more. Furthermore, as the solution is removed and placed back in the biological reactor, some amount of solution can be lost. Additionally, extraction and reintroduction of the sample media can undesirably disrupt the cells or other substances in the solution.

In addition to the described issues, the various solutions presented above can suffer from limitations with respect to the amount of sample required for compound detection, the measurability of parameters that can be relatively difficult to detect (e.g., phase variation of sensing signals), and/or limited frequency bandwidth constraints.

In some implementations, the present disclosure relates to sensing devices and/or techniques that use electromagnetic resonance to detect properties of a sample and/or one or more constituents thereof. For example, sensing devices in accordance with aspects of the present disclosure can be immersed into a sample, placed in proximity to a sample, or otherwise located within sensing range of a sample. The sensing device can transmit a signal into the sample and receive a reflected signal using a resonating structure. In some implementations, the reflected signal can be analyzed to detect the presence and/or concentration of one or more constituents in the sample. Certain systems, devices, and methods disclosed herein can advantageously allow for detection of a constituent in a sample substantially without removing the sample from a container or other structure (e.g., anatomy) in which the sample is at least partially disposed. Furthermore, in some embodiment the devices and/or techniques can be implemented while maintaining the sample and/or structure containing the sample in its initial state.

FIG. 1 illustrates an example system 100 that includes a sensing device and/or system 110 configured to detect a constituent in a sample 140 in accordance with one or more embodiments of the present disclosure. For example, the sample 140 may be disposed and/or contained at least partially within a container 150. The sensor device/system 110 may be a single device, an assembly of devices and/or components, and/or a system of separate devices collectively configured to provide the described sensing and/or computational functionality associated with embodiments of the present disclosure. In some embodiments, the sensing system 110 is configured to sense constituent(s) of the sample 140 using a resonating structure and/or circuitry. As illustrated, the sensing system 110 includes control circuitry 120 and a sensor 130 electrically coupled to the control circuitry 120.

In some embodiments, the sensor 130 advantageously includes a transmitting portion 132 and a resonating portion 134 electrically coupled to the transmitting portion 132. The transmitting portion 132 and the resonating portion 134 may form a single structure in some implementations. In some implementations, the transmitting portion 132 and the resonating portion 134 are separate components that are configured to be physically and/or electrically coupled to one another, such as through cables, wires, threading, fasteners, electrically conductive adhesive, etc. The transmitting portion 132 can include an outer conductor and/or an inner conductor. In some embodiments, the transmitting portion 132 includes a dielectric material disposed at least partially within the outer conductor. The resonating portion 134 can likewise include an outer conductor and/or an inner conductor. The outer conductor may be configured to form a resonator cavity structure. For example, the cavity structure may provide an at least partially hollow cavity. The sensor 130 can take on a variety of forms in accordance with inventive aspects of the present disclosure, such as a cylinder-shaped coaxial transmission line, a square-axial transmission line, a dielectric-filled waveguide, a microstrip transmission line, a stripline transmission line, a coplanar waveguide transmission line, and the like. In some embodiments, the sensor 130 can comprise and/or be formed at least partially with a printed circuit board that forms a transmission line.

The control circuitry 120 can interface with the sensor 130 to receive/determine signals indicating the presence and/or concentration of one or more constituents in the sample 140. To such end, the control circuitry 120 may be electrically and/or physically coupled to the sensor 130 using one or more connectors or other structures or components. In some embodiments, the control circuitry 120 is electrically coupled to the sensor 130 using capacitive and/or inductive coupling with respect to one or more components or portions of the sensor 130. Although the control circuitry 120 and sensor 130 are shown as separate blocks in the system 100 of FIG. 1, it should be understood that the control circuitry 120 and sensor 130 may be integrated with one another in some respects and certain embodiments. For example, in some embodiments, the sensor 130 comprises an outer housing (e.g., conductor) configured to house one or more portions of dielectric material, inner conductors, and/or the like, wherein such housing additionally houses or is otherwise coupled or associated with one or more components or elements of the control circuitry 120. For example, the sensor 130 and/or an at least partially rigid housing or structure thereof may serve to house one or more circuit boards or other substrates for circuitry and associated devices.

The control circuitry 120 can advantageously be configured to transmit a signal into the sample 140 using the sensor 130. For example, the signal can be propagated through the transmitting portion 132 and the resonating portion 134, and onto the sample 140 via one or more electrodes of the resonating portion 134 that contact or are positioned in physical proximity to at least a portion of the sample 140. The control circuitry 120 can receive a reflected signal using the resonating portion 134 and the transmission line portion 132 of the sensor 130. For example, the reflected signal may be received using one or more electrodes of the resonating portion 134. The control circuitry 120 can be configured to analyze certain properties of the reflected signal to determine a resonant frequency associated with the sample 140 and/or resonating portion 134. For example, the control circuitry 120 can analyze an amplitude and/or a phase of the reflected signal. In some implementations, the control circuitry 120 is configured to determine the resonant frequency of the sample 140 and/or resonating portion 134 by analyzing signals over a range of frequencies. For example, the control circuitry 120 can transmit multiple signals of different frequencies and analyze respective reflected signals associated therewith to identify a reflected signal that is associated with the resonant frequency of the sample/resonator. With respect to certain description of embodiments of the present disclosure herein, references to a resonant frequency of a target sample should be understood to refer to a resonant frequency of a resonator device or assembly in the presence of, and/or influenced by, the target sample. That is, the target sample may introduce certain electrical characteristics to the resonating portion 134 that alter and/or determine the resonant characteristics of the resonating portion 134. The resonant frequency of the resonating portion 134 under such conditions is referred to herein as the resonant frequency of the target sample and or the resonating portion 134. Based on the determined resonant frequency of the sample 140, the control circuitry 120 can be configured to determine a presence and/or concentration of a particular constituent, such as glucose, in the sample 140. For example, the resonant frequency associated with the sample 140 can correlate to a concentration of the relevant constituent in the sample 140.

As noted above, in some embodiments the sensing system 410 can analyze an amplitude of a reflected signal to determine a resonant frequency of the sample 140. To facilitate such detection, the sensor 430 can include an absorptive material (not illustrated in FIG. 4) disposed at an interface between the transmitting portion 432 and the resonating portion 434, as shown in various figures discussed hereafter. In some embodiments, an amplitude of a signal is more easily and/or accurately detected than a phase of a reflected signal. As such, in some embodiments, by analyzing an amplitude of a reflected signal, the sensing system 410 can more accurately detect a resonant frequency associated with a sample.

The sample 140 can include any substance in a solid, liquid, or gaseous form. For example, the sample 140 can include one or more biological compositions, organic chemical compositions, inorganic chemical compositions, and/or combinations thereof. For example, in some sensing systems in accordance with aspects of the present disclosure, a target sample can comprise food (e.g., fruit, vegetables, dairy products (such as yogurt), beer, etc.). The term "constituent" is used herein according to its broad and ordinary meaning, and may refer to any component part of a material, substance, compound, solution, element, object, and/or combination thereof. Furthermore, with respect to biological constituents, the term "constituent" may be used herein to refer to a biological element and/or biological compound. Example constituents that may be relevant to embodiments of the present disclosure include, but are not limited to, glucose, lactase, alcohol, and the like.

The container 150 can comprise any structure and/or material to hold or contain the sample 140. For example, the container 150 can comprise a biological reactor (also referred to as a bioreactor), a petri dish, a jar, a test strip, human tissue, and so on. In some embodiments, the container 150 is at least partially rigid. The container 150 may comprise a container portion and a lid portion in some implementations. In some embodiments, the container 150 comprises a bag structure (e.g., polymer bag) that is at least partially flexible and/or amorphous.

Figure 2:
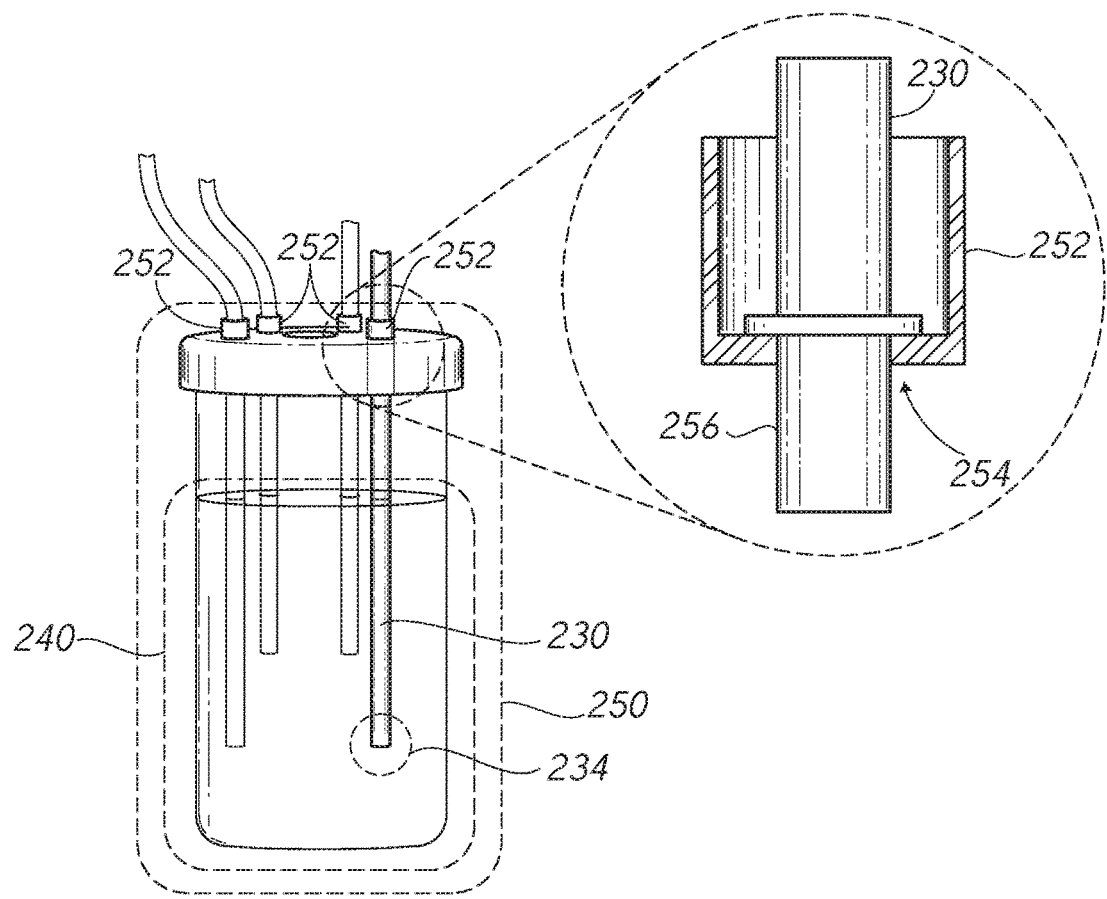
FIG. 2 illustrates an example sensor that is configured to be at least partially inserted into and/or disposed within a container.

FIG. 2 illustrates an example sensor 230 that is configured to be at least partially inserted into and/or disposed within a container 250. In this example, the container 250 is implemented as a bioreactor. However, it should be understood that the container 250 can be implemented as any of the containers discussed herein, and the sensor 230 can be implemented as any of the sensors discussed herein.

A bioreactor can comprise physical structure configured and/or designed to be used as a system that provides a biologically active environment. For example, a bioreactor container may be used to house and/or contain a liquid medium, solid medium, or any combination thereof suitable to maintain an organism or biochemical substance therein. For example, a bioreactor can contain a solution of glucose and water used as a substrate to grow cells or tissue (e.g., blood cell culture). Such cells/tissue can be programmed to grow, for example, a substance of interest, such as a protein. It should be understood that a variety of solutions, organisms, and/or substances can be contained within a bioreactor in accordance with system embodiments disclosed herein.

A bioreactor can include a variety of components to facilitate a biologically-active environment. For example, a bioreactor can include one or more of a vessel to contain a solution, an agitation system to agitate the solution, an air system to provide air to the solution, an aerator to assist in providing air to the solution, a pump to push solution into the bioreactor and/or remove solution from the bioreactor, a sensor to detect a substance in the vessel (e.g., an oxygen sensor, a PH sensor, etc.), and so on.

In the example of FIG. 2, the bioreactor 250 includes ports 252 to enable components to be connected to the bioreactor 250. As illustrated, each port 252 includes an opening or access 254 to enable a component to be inserted there through into an interior portion of the bioreactor 250 that houses the sample 240. In the illustrated embodiment of FIG. 2, the sensor 230 and components 258 are inserted through the ports 252. The sensor 230, and/or one or more components associated therewith, is configured to be inserted into/through the access/opening 254, so that the sensor 230 can be partially immersed into the sample 240 while the sample 240 remains in the bioreactor 250. In some embodiments, the sensor 230 can be designed based on a structure of the bioreactor 250. For instance, the sensor 230 can be configured to have a diameter that is less than a diameter of the access/opening 254, a length that enables the sensor 230 to be immersed into the sample 240, etc.

In some embodiments, a resonating portion 234 of the sensor 230 can be used to detect a constituent in the sample 240. For example, the sample 240 can at least partially fill and/or occupy a resonator cavity of the resonating portion 234 when the resonating portion 234 is disposed at least partially within the sample 240. Therefore, the resonating portion 234 may advantageously be associated with a distal end portion of the sensor 230, such that the resonating portion 234 is generally disposed farthest within and/or contacts first the sample 240 when inserted into the container 250 via the port 252. The sensor 230 can be connected to, and/or operate in concert with, certain control circuitry (not illustrated) for the purpose of transmitting an electromagnetic signal into the sample 240 and/or analyzing a reflected signal received from the resonating portion 234 and the sample 240. The reflected signal can be analyzed to detect, for example, the presence and/or a concentration of glucose or another constituent(s) in the sample 240.

In some embodiments, a grommet structure 256 is disposed over at least a portion of the sensor 230 when the sensor 230 is disposed in the bioreactor 250 to isolate one or more devices/components associated with the sensor 230, and/or the outside environment, from the sample 240. In some implementations, the present disclosure relates to the grommet structure 256 including a flange portion configured to secure the sensor 230 in a position associated with a desired vertical offset; that is, the flange feature may prevent the sensor 230 from advancing too far into the sample 240. The grommet structure 256 can be physically attached to and/or integrated with the sensor 230, or may be a separate component.

In some embodiments, the sensor 230 is associated with a filter/cover (not shown) that at least partially covers the resonating portion 234 of the sensor 230. The filter can allow liquid to pass into a resonator cavity while at least partially preventing cells and other substances outside the resonator cavity from passing into the resonating chamber of the resonating portion 234. The filter can include a semi-permeable membrane to enable a substance of a particular size to pass through. The semi-permeable membrane can include relatively small pores (e.g., less than 100 micrometers). In some embodiments, the cover is disposed at least partially over the distal end portion of the sensor 230, and may be limited to that portion of the sensor 230. Alternatively, in some embodiments, no cover is associated with the resonating portion 234 and/or distal end portion of the sensor 230, such that the sample media can flow substantially freely therein.

In some implementations, the sample 240 can be become undesirably disrupted if removed from the bioreactor 250. As such, the examples sensor 230 of FIG. 2 can be provided through the port 252 to maintain the sample 240 in a substantially unaltered/undisturbed state. This can avoid loss of the sample 240 associated with transferring portion(s) thereof to a separate device/location for measuring levels of a constituent, such as glucose. Furthermore, since the sensor 230 can be maintained in the bioreactor 250, the sensor 230 can be configured to continuously monitor the sample 240 in some implementations.

Figure 3:
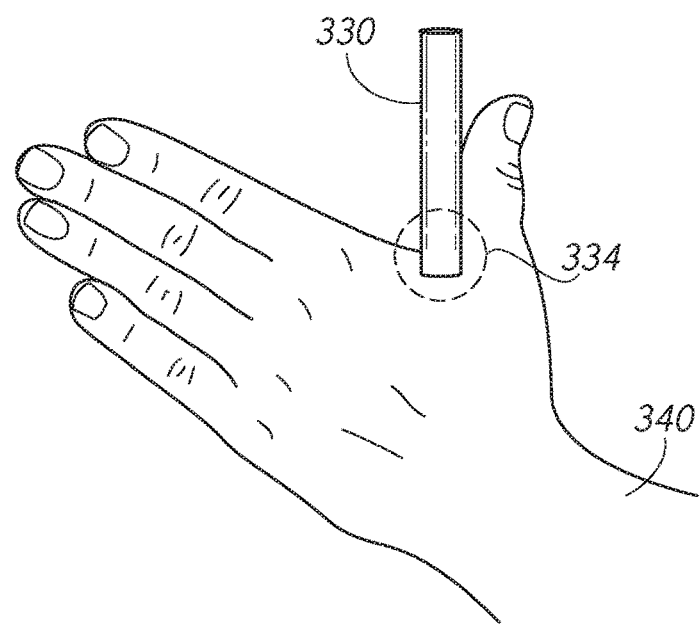
FIG. 3 illustrates an example sensor that is configured to contact or be placed in physical proximity to human tissue of a member of a patient to detect a constituent blood or another substance within or associated with the human tissue.

FIG. 3 illustrates an example sensor 330 that is configured to contact or be placed in physical proximity to human tissue 340 of a member of a patient to detect a constituent blood or another substance within or associated with the human tissue 340. In the illustrated implementation, the human tissue 340 (e.g., skin and/or adjacent tissue) can represent a container that houses a sample, wherein the sample is blood flowing or contained therein and/or other biological substance. The sensor 330 can be representative of any of the sensors discussed herein.

In some embodiments, a resonating portion 334 of the sensor 330 can be used to detect a presence and/or concentration of a constituent in the human tissue 340. For example, the resonating portion 334 of the sensor 330 can contact the human tissue 340 at a location where a concentration of blood is relatively high, such as in proximity to a blood vessel (e.g., vein or artery), and/or in a region in which one or more blood vessels are relatively close to the skin. In the example of FIG. 3, the sensor 330 is placed between the thumb and index finger. However, it should be understood that the sensor 330 can be placed in a variety of locations on a human body, such as on an ear lobe. The sensor 330 can be electrically and/or physically coupled/connected to control circuitry (not illustrated) to facilitate the transmission of a signal into the human tissue 340 using the sensor 330 and analyze reflected signal(s) received by the sensor 330 from the human tissue 340. The reflected signal(s) can be analyzed to detect, for example, a concentration of glucose or another constituent in blood associated with the human tissue 340.

In some embodiments, the sensor 330 is not limited to through- or multi-detector measurement configurations. For example, a sample can be detected by having the sensor 330 contact just one side of human tissue, without requiring a signal to be transmitted through the human tissue and received on an opposing side of the human tissue. Further, the sensor 330 can allow a sample to remain pure and/or unperturbed using non-destructive and non-altering electromagnetic energy. For example, a sample can be detected without removing the sample from a container.

Figure 4:
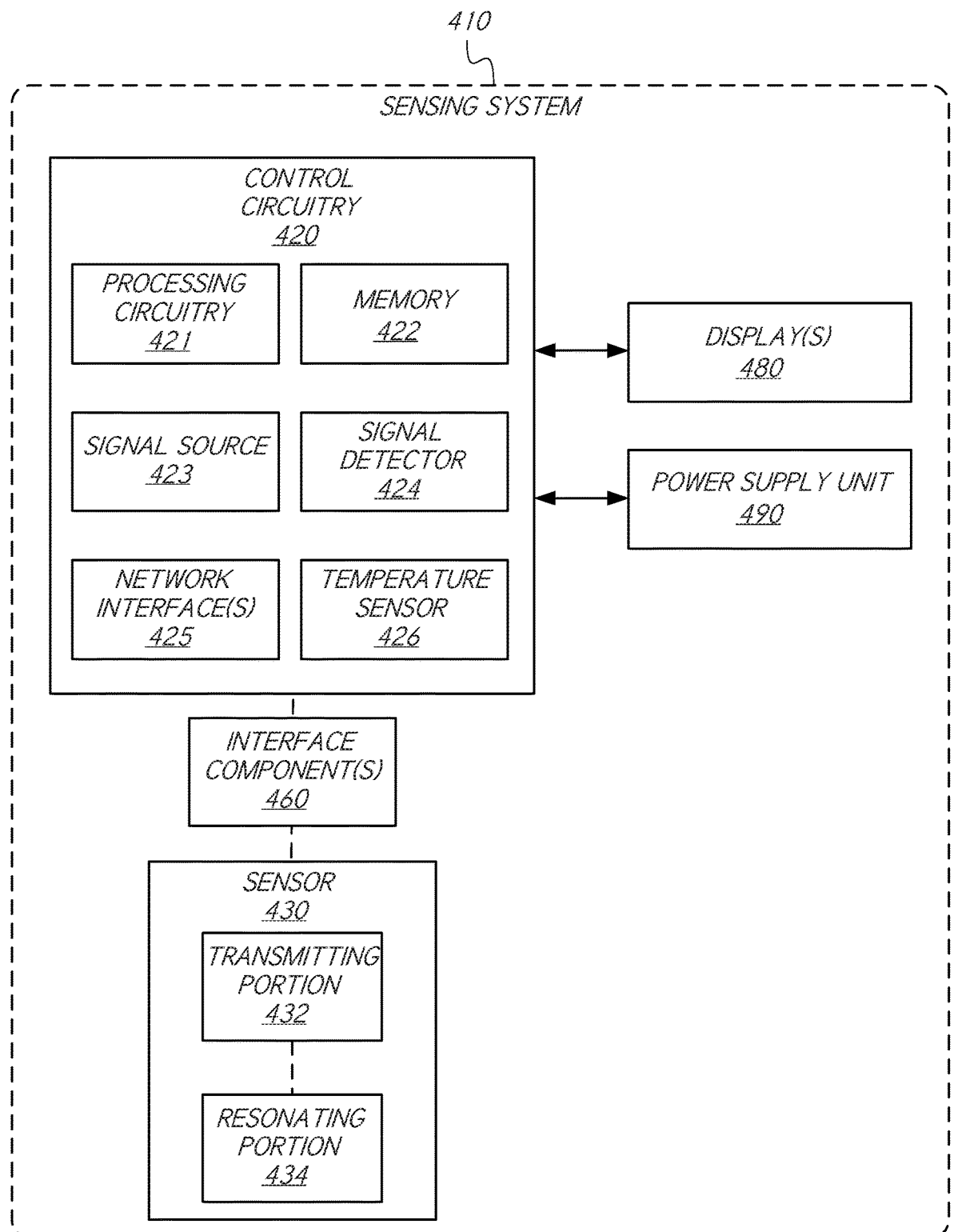
FIG. 4 illustrates an example block diagram of a sensing system that can be implemented in any of the example embodiments discussed herein.

FIG. 4 illustrates an example block diagram of a sensing system 410 that can be implemented in any of the example embodiments discussed herein. The sensing system 410 can include control circuitry 420 electrically coupled to a sensor 430 via one or more interface components 460. Although the one or more interface components 460 are illustrated in FIG. 4, in some examples the sensing system 410 can be implemented without the one or more interface components 460. The term "interface" is used herein according to its broad and ordinary meaning and may refer to any structure, device(s), and/or mechanism(s) configured to facilitate electrical, wireless/electromagnetic, and/or physical coupling between two or more structures, devices, components, elements, or the like. The sensing system 410 can also include one or more displays 480 and/or a power supply unit 490 that are communicatively coupled to the control circuitry 420 and/or other components of the sensing system 410.

As illustrated, the control circuitry 420 can include one or more of processing circuitry 421, memory 422, a signal source 423, and a signal detector 424. In some embodiments, the processing circuitry 421, the memory 422, the signal source 423, and/or the signal detector 424 can operate in cooperation to facilitate various operations discussed herein. For example, the processing circuitry 421 can be configured to execute instructions that are stored in the memory 422 to facilitate the various operations. In some embodiments, the processing circuitry 421 is configured to control the signal source 423 and/or the signal detector 424 for the purpose of determining the resonant frequency of a resonating portion 434 of the sensor 430, which can indicate the presence and/or concentration of a target constituent in a target sample, as described in detail herein. Although the processing circuitry 421, memory 422, signal source 423, and signal detector 424 are illustrated as separate components, any of these components can be combined and/or implemented within another component. For example, the processing circuitry 421 and memory 422 can be part of first control circuitry (e.g., a first computing device), while the signal source 423 and/or signal detector 424 can be part of second control circuitry (e.g., a second computing device). In some implementations, one or more functional components of the control circuitry 420, and/or one or more portions thereof, are embodied in one or more electronic chips, such as surface-mount chip(s), or the like. Additionally or alternatively, one or more functional components of the control circuitry 420, and/or one or more portions thereof, can be implemented within and/or on one or more printed circuit boards or other substrate(s).

In some embodiments, the processing circuitry 421 can operate in cooperation with the signal source 423 to provide a signal to the resonating portion 434 and/or to a target sample, wherein the resonating portion 434 is disposed at least partially within and/or adjacent to the target sample. For instance, the processing circuitry 421 can direct or cause the signal source 423 to transmit a signal to the sensor 430 using the interface component(s) 460 (e.g., electrical connectivity circuitry). The signal can be propagated at least partially through the sensor 430 and through/near a sample (not illustrated). In some embodiments, the signal source 423 can include an oscillator, such as voltage-controlled oscillator (VCO). In some embodiments, the processing circuitry 421 can direct or cause the signal source 423 to sweep across a range of frequencies. That is, the signal source 423 can be directed to transmit multiple signals at different frequencies over a range of frequencies. The multiple signals may be transmitted (and analyzed) sequentially, for example. The range of frequencies can be associated with a constituent that is being detected and/or a sample in which the constituent is disposed. For example, if glucose is being detected in a solution including water, it can be estimated that glucose will be within a certain concentration range in the solution. That concentration range can be correlated to a frequency range that is associated with glucose and/or water. In some embodiments, the signal source 423 can generate a signal that has a relatively high frequency, such as a microwave frequency (e.g., a frequency between 300 MHz and 300 GHz) or other radiofrequency radiation. However, the signal source 423 can be configured to generate signals of any frequency.

In some embodiments, certain properties of an electromagnetic signal transmitted to the resonating portion 434 are changed at least in part as the signal passes through a sample. For example, properties of the signal can be affected by one or more constituents in the sample and/or a concentration of the constituents in the sample. In some implementations, an amplitude and/or phase of a signal can be changed at least in part by a concentration of a constituent in a sample. For example, the properties of a signal can be changed in a correlated manner (e.g., proportional, inversely proportional, etc.) to a concentration of the constituent. In some embodiments, glucose is associated with a relatively high polar moment (e.g., above a certain threshold), which can affect properties of an electromagnetic signal passing through the glucose.

In some embodiments, the processing circuitry 421 can operate in cooperation with the signal detector 424 to detect a reflected signal from a sample. For instance, the processing circuitry 421 can receive a reflected signal from the signal detector 424. The reflected signal can initially be received at the sensor 430 and passed on to the signal detector 424. The processing circuitry 421 can analyze properties of the reflected signal to identify a resonant frequency associated with a sample. The processing circuitry 421 can generally be configured to analyze an amplitude and/or a phase of the reflected signal. In some embodiments, the signal detector 424 can include a component configured to detect a signal, such as a directional coupler and/or similar circuitry. In some embodiments, the processing circuitry 421 can analyze multiple reflected signals associated with different frequencies. For instance, the control circuitry 420 can analyze multiple reflected signals to identify a reflected signal that is associated with a lowest (or highest) amplitude/magnitude (e.g., identify a null or lowest point in the analyzed reflected signals frequencies). In some embodiments, the processing circuitry 421 is configured to analyze amplitude with respect to voltage.

In some embodiments, the memory 422 can be configured and coupled to store data regarding a target constituent. For example, the memory 422 can be configured to store data indicating a resonant frequency associated with a sample, data indicating a concentration of a constituent in a sample, etc.

The processing circuitry 421 can include one or more processors, such as one or more central processing units (CPUs), one or more microprocessors, one or more graphics processing units (GPUs), one or more digital signal processors (DSPs), etc. Alternatively or additionally, the processing circuitry 421 can include one or more application specific integrated circuits (ASIC), one or more field-programmable gate arrays (FPGAs), one or more program-specific standard products (ASSPs), one or more complex programmable logic devices (CPLDs), and/or the like.

The memory 422 can include any suitable or desirable type of computer readable media. For example, computer readable media of the data storage 422 can include one or more volatile data storage devices, non-volatile data storage devices, removable data storage devices, and/or nonremovable data storage devices implemented using any technology, layout, and/or data structure(s)/protocol, including any suitable or desirable computer readable instructions, data structures, program modules, or other data types. Computer readable media that may be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer readable media may not generally include communication media, such as modulated data signals and carrier waves. As such, computer readable media should generally be understood to refer to non-transitory media.

The control circuitry 420 can also include one or more network interfaces 425. The one or more network interfaces 425 can be configured to communicate with one or more device over a communication network. For example, the one or more network interfaces 425 can send/receive data in a wireless or wired manner over a network. A communication network in accordance with embodiments of the present disclosure can include a local area network (LAN), a wide area network (WAN) (e.g., the Internet), personal area network (PAN), body area network (BAN), etc. In some embodiments, the one or more network interfaces 425 can implement a wireless technology such as Bluetooth, Wi-Fi, near field communication (NFC), or the like. In some embodiments, the control circuitry 420 can send/receive data regarding a sample using the one or more network interfaces 425, such as data indicating a resonant frequency associated with a sample, data indicating a concentration of a constituent in a sample, and/or other data related to certain aspects of the present disclosure. In some embodiments, the control circuitry 420 can report data regarding a sample using the one or more network interfaces 425. For example, the control circuitry 420 can continuously or periodically, or at any other time measure a sample and report such measurement data to a remote device.

Further, the control circuitry 420 can include a temperature sensor 426 configured to detect a temperature of the sensing system 410. The temperature can be used to calibrate the sensor 430 and/or correct measurements by the sensor 430, which may include materials that are temperature dependent. In some embodiments, the temperature sensor 426 can be integrated into the transmitting portion 432 of the sensor 430.

The one or more displays 480 can be configured to display data associated with certain aspects of the present disclosure. For example, the data can include data indicating a resonant frequency associated with a sample, data indicating a concentration of a constituent in a sample, a graph of such information, and/or the like. Additionally or alternatively, the one or more displays 480 can be configured to present a graphical user interface (GUI) to facilitate operation of the sensing system 410. The one or more displays 480 can include a liquid-crystal display (LCD), a light-emitting diode (LED) display, an organic LED display, a plasma display, an electronic paper display, or any other type of technology. In some embodiments, the one or more displays 480 include one or more touchscreens and/or other user input/output (I/O) devices. The sensing system 410 can also include other types of input and/or output components, such as a keyboard, a mouse, a camera, microphone, USB port, etc. As such, in some implementations, the control circuitry 420 and/or one or more displays 480 can receive input from a user using such I/O device(s). Although the one or more displays 480 are illustrated as being included within the sensing system 410, in some embodiments, the one or more displays 480 are separate from the sensing system 410 or are not implemented/included.

The power supply unit 490 can include a mains power connector that is configured to couple to an alternating current (AC) or direct current (DC) mains power source. Alternatively or additionally, the power supply unit 490 can include one or more batteries, such as lithium-based, lead-acid, alkaline, and/or other type(s) of batteries. In some embodiments in which the sensing system 410 is implemented as a handheld or other type of mobile device, the power supply unit 490 can advantageously include one or more batteries.

Although the one or more displays 480 and the power supply unit 490 are illustrated outside the control circuitry 420, in some examples the one or more displays 480 and/or the power supply unit 490 are included within the control circuitry 420.

The one or more interface components 460 can include a variety of components to electrically and/or physically couple the control circuitry 420 to the sensor 430. For example, the one or more interface components 460 can include connectors, splitters, separators, couplers, etc. Additionally or alternatively, the one or more interface components 460 can be configured to communicate to a remote device. For instance, the control circuitry 420 can be located remotely to the sensor 430 and the one or more interface components 460 can communicate with the control circuitry 420 in a wireless and/or wired manner. As such, in some examples the one or more interface components 460 can enable communication over a network.

In some embodiments, the sensing system 110 is implemented as a handheld device. For example, the sensing system 110 can include housing and/or other components that enable a user to hold the sensing system 110. Further, the control circuitry 420 of the sensing system 410 can be configured to operate in a manner that optimizes power consumption. For example, the sensing system 410 can include a battery, and the control circuitry 420 can operate in a reduced-power configuration to conserve battery life. In some embodiments, in a handheld configuration, the control circuitry 420 can use a periodic or pulsating process(es) for monitoring constituent levels in a sample, as opposed to continuous transmission and/or detection of signals by the sensor 430 as in some embodiments of the present disclosure.

In some embodiments, the control circuitry 420 includes a network analyzer, which may be used and configured to facilitate analysis of reflected signals for constituent measurement in accordance with aspects of the present disclosure. The sensing system 410 and/or control circuitry 420 may further comprise one or more additional computing devices, one or more circuit boards (e.g., a single-board computer (SBC)), and/or other device(s), which may be used to generate and/or analyze electromagnetic signals in accordance with embodiments of the present disclosure. Moreover, one or more components of the sensing system 410 can include a variety of conductive elements, such as wires, traces, cables, buses, or other connectivity circuitry to connect components of the system 410 and/or elements within each component.

Figure 5A:
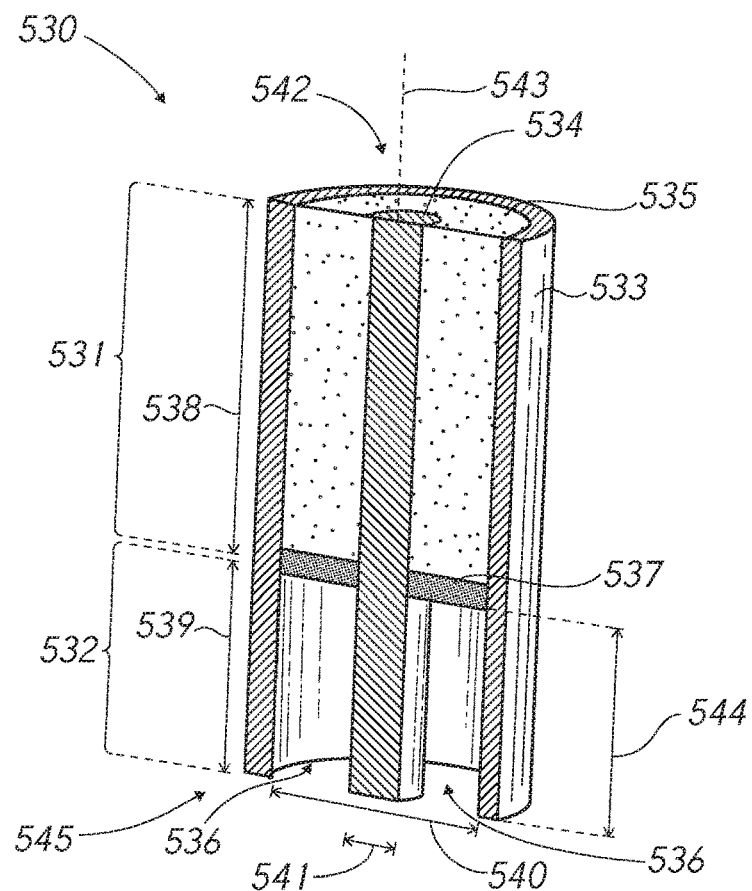
FIG. 5A illustrates a perspective view of a portion of an example sensor that has a substantially cylindrical shape in accordance with one or more embodiments of the present disclosure.
Figure 5B:
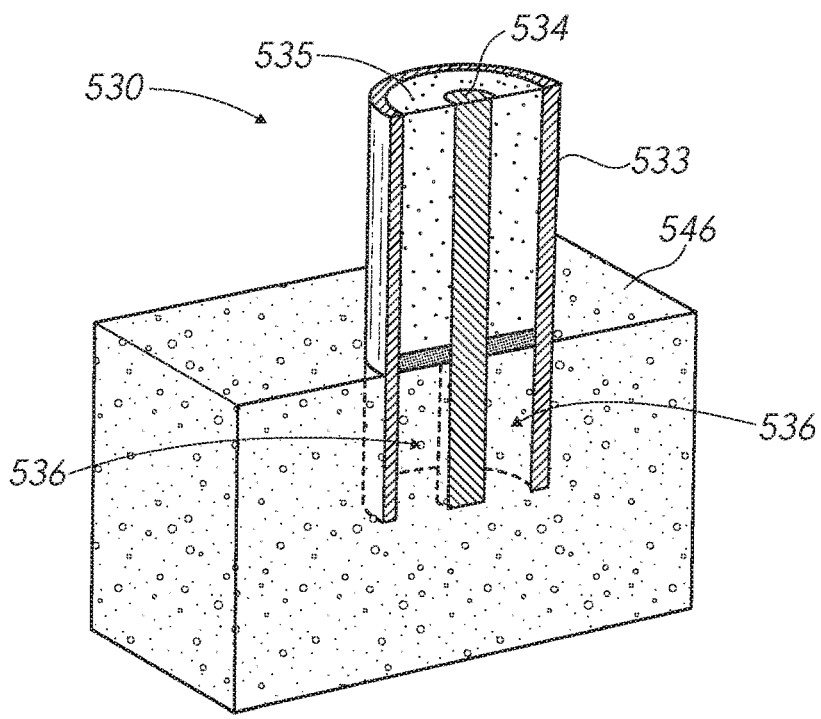
FIG. 5B illustrates a perspective view of a portion of the sensor shown in FIG. 5A, wherein a resonating portion thereof is disposed at least partially within sample media.

FIG. 5A illustrates a perspective view of a portion of an example sensor 530 that has a substantially cylindrical shape in accordance with one or more embodiments of the present disclosure. FIG. 5B shows a perspective view of the portion of the sensor 530 shown in FIG. 5A, wherein a resonating portion 532 thereof is disposed at least partially within sample media 546, as shown. FIGS. 5A and 5B show cross-sectional perspective views of the sensor 530. The sensor 530 represents an example embodiment of a sensor device/system (or component/portion thereof) that can be implemented in the various example devices and systems disclosed herein.

The sensor 530 includes a transmitting portion 531 (sometimes referred to as the "proximal elongate transmitting portion 531") and a resonating portion 532 (sometimes referred to as the "distal resonating portion 532"). As illustrated, the sensor 530 can include a cylindrical elongated form. However, in some embodiments, the sensor 530 can take other forms. The transmitting portion 531 and/or the resonating portion 532 can include an outer conductor 533 and/or an inner conductor 534, which may be configured in a coaxial arrangement, as shown. For example, the outer conductor 530 may be configured to at least partially surround the inner conductor 534, as shown. In some embodiments, the outer conductor 533 is formed at least in part of a continuous and/or unitary structure or form that spans at least a portion of the transmitting portion 531 and the resonating portion 532 with respect to the longitudinal axis 543 of the sensor 530. In some embodiments, the outer conductor 533 comprises two or more separate structures or forms, each of which is associated with one or more of the transmitting portion 531 and the resonating portion 532. If separate outer conductor structures/forms are implemented, the structures can be configured to be connected or physically coupled in some manner. Similarly, the inner conductor 534 can be formed at least in part of a continuous and/or unitary structure or form that spans at least a portion of the transmitting portion 531 and the resonating portion 532 with respect to the longitudinal axis 543 of the sensor 530. In some embodiments, the inner conductor 534 comprises two or more separate structures or forms, each of which is associated with one or more of the transmitting portion 531 and the resonating portion 532. If separate inner conductor structures/forms are implemented, the structures can be configured to be connected or physically coupled in some manner. The outer conductor 533 and/or the inner conductor 534 are advantageously formed at least partially of a conductive material, such as a metal (e.g., copper, steel, stainless steel, etc.), in some embodiments.

In the example of FIGS. 5A and 5B, the inner conductor 534 extends along the central axis 543 of the outer conductor 533 and/or sensor 530. That is, the inner conductor 534 can generally be concentric with the outer conductor 533 in some embodiments. In other embodiments, the inner conductor 534 can be offset from the central axis 543. The inner conductor 534 can have any length, which can be different than a length of the outer conductor 533, or may be substantially the same length. As in the illustrated embodiment of FIGS. 5A and 5B, the inner conductor 534 can have a cylindrical elongated form/shape. However, other forms can be used within the scope of the present disclosure.

The transmitting portion 531 of the sensor 530 can include a dielectric material 535 disposed at least partially within one or more portions of a space disposed between the outer conductor 533 and the inner conductor 534 (e.g., disposed in an interior portion of the transmitting portion 531). In some embodiments, the dielectric material 535 can include a variety of electrically insulating materials, such as air, Teflon, Delrin, etc. The dielectric material 535 can be polarized by an electric field in some implementations.

The portions of the outer conductor 533 and/or the inner conductor 534 associated with the resonating portion 532 can form a cavity 536 (also referred to herein as the "resonator cavity"). The cavity 536 can be used to transmit/propagate electromagnetic signals, including reflected electromagnetic signals having characteristics indicative of the concentration of one or more constituents in at least a portion of the sample 546. The cavity 536 can enable electromagnetic waves transmitted on the inner conductor 534 and/or outer conductor 533 to reflect back and forth between walls of the cavity 536. In some embodiments, the cavity 536 is fluidly isolated from an interior of the transmitting portion 531 (e.g., an interior portion of the transmitting portion 531 where the dielectric material 535 is located). In some embodiments, the cavity 536 is advantageously at least partially hollow. In some embodiments, the cavity 536 can be at least partially filled with a material (e.g., dielectric), such as a non-conducting material. In one example, the cavity 536 is at least partially filled with a sponge-like material that enables a liquid to be absorbed into the material/cavity 536 (e.g., a liquid solution comprising glucose), while blocking other substances (e.g., cells). A length 544 of the cavity 536 (and/or a thickness of an absorptive material 537) can define an available sensing depth of the sensor 530. In some embodiments, a sample within the cavity 536 can affect a propagation velocity of incident electromagnetic signals.

In some embodiments, the absorptive material 537 (also referred to as "the electrically absorptive material 537") can be disposed at an interface between the dielectric material 535 of the transmitting portion 531 and the cavity 536 of the resonating portion 532. In some embodiments, as shown, the absorptive material 537 can be disposed between the outer conductor 533 and the inner conductor 534. The absorptive material 537 can serve to absorb at least a portion of electromagnetic signals incident thereon to isolate or shield the cavity 536 and/or shield the outer conductor 533 from the inner conductor 534. The absorptive material 537 can have a predetermined thickness, which may be selected to produce the desired absorption characteristics/functionality. In some embodiments, a thickness of the absorptive material 537 can be less than a length 544 of the cavity 536. The absorptive material 537 may provide electrical functionality that is substantially equivalent to a grounded resistance in some implementations. Although the absorptive material 537 is illustrated here, in other examples the absorptive material 537 can be replaced with a surface mount resistor or another device/component in some implementations. In some embodiments, the absorptive material 537 can block or at least partially prevent the sample 546 from penetrating into the dielectric material 535 (and/or space occupied thereby) of the transmitting portion 531.

In some embodiments, the sensor 530 can be designed for various applications or contexts. That is, one or more dimensions of the sensor 530 can be determined/designed for any number of applications. For example, any of the following dimensions can be adjusted: a length 538 of the transmitting portion 531 (which can include or exclude the absorptive material 537), a length 539 of the resonating portion 532 (which can include or exclude the absorptive material 537), a diameter 540 of an inner surface of the outer conductor 533, a diameter 541 of the inner conductor 534, the length 544 of the cavity 536, a length of the sensor 530 (which includes the length 538 and the length 539), a distance between an inner surface of the outer conductor 533 and an outer surface of the inner conductor 534, a thickness of the outer conductor 533 (e.g., a radial thickness), etc. Any of such dimensions can be tuned to achieve a desired performance characteristic. To illustrate, the length 544 of the cavity 536 (e.g., a length of the inner conductor 534 within the cavity 536) can be tuned for a particular application.

A proximal end 542 of the sensor 530 can provide an interface to electrically and/or physically connect/couple to control circuitry (not illustrated) or another device. The end 542 can be considered a proximal end of the sensor 530 with respect to the control circuitry, whereas an end portion 545 of the sensor 530 can be considered a distal end of the sensor 530 with respect to the control circuitry. In some embodiments, the proximal end 542 of the sensor 530 can be connected to one or more interface components, such as components that represent example embodiments of the one or more interface components 460 of FIG. 4. Additionally or alternatively, the end 542 of the sensor 530 can be connected to other layers, structures, and/or features that can be implemented to use the sensor 530. In some embodiments, the sensor 530 can be constructed at least partially with a transmission line structure, such as a coaxial transmission line, for example.

FIG. 5B shows an example of the sensor 530 immersed in a sample 546. In the illustrated disposition, the resonating portion 532 of the sensor 530 is fully immersed into the sample 546. However, it should be understood that in some implementations, the resonation portion 532 is only partially submerged in the sample 546, or may not be submerged, but rather disposed in physical proximity to the sample 546 and/or container or tissue associated therewith. The sample 546 can include a liquid, a semi-liquid, a solid substance, a gas, a vacuum space, etc. In the illustrated disposition, the sample 546 is disposed at least partially within the resonator cavity 536. In some implementations, the resonating portion 532 can be partially immersed into the sample 546 or the sensor 530 can be immersed into the sample 546 so that the sample 546 is above the resonating portion 532 (e.g., surrounding at least a portion of the outer surface of the transmitting portion 531).

Figure 6A:
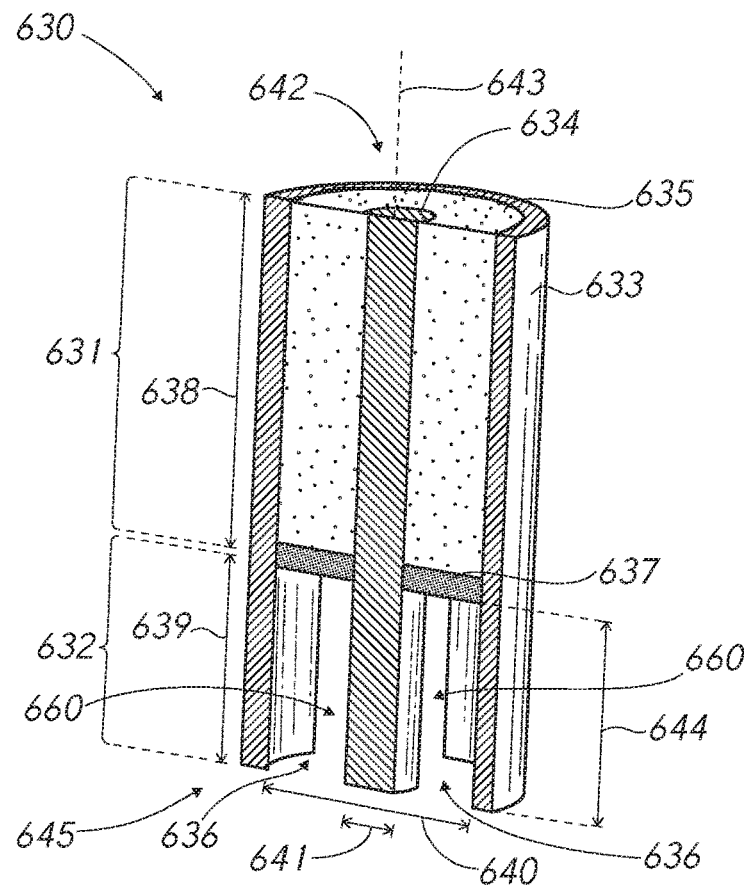
FIG. 6A illustrates a cross-sectional perspective view of an example sensor that has a substantially cylindrical shape and includes one or more slot features.
Figure 6B:
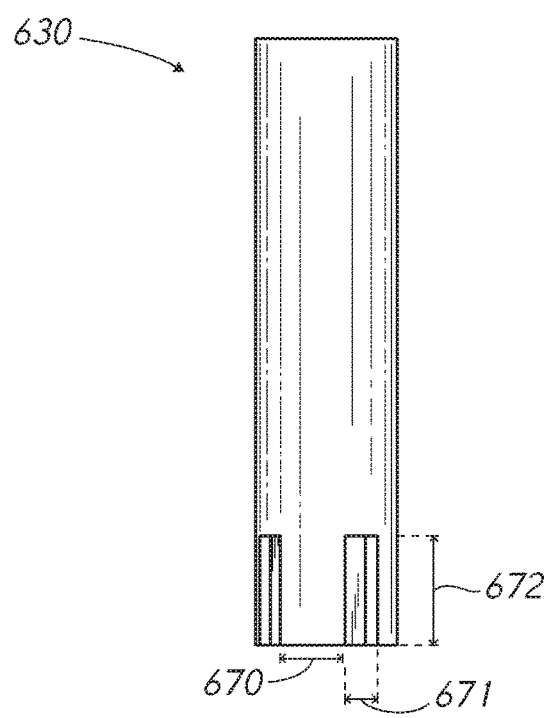
FIG. 6B illustrates a front view of an example sensor that has a substantially cylindrical shape and includes one or more slot features.

FIGS. 6A-6B illustrate an example sensor 630 that has a substantially cylindrical shape and includes one or more slot features associated with one or more portions of the sensor 630 (e.g., resonating portion). In particular, FIG. 6A shows a cross-sectional perspective view of the sensor 630, while FIG. 6B shows a front view of the sensor 630. Sensor devices/systems like the sensor 630 can be implemented in any of the examples discussed herein.

The sensor 630 includes a transmitting portion 631 and a resonating portion 632. As illustrated, the sensor 630 can include a cylindrical elongated form. Although in other examples the sensor 630 can take other forms. The transmitting portion 631 and/or the resonating portion 632 can include an outer conductor 633 and/or an inner conductor 634. The outer conductor 633 surrounds the inner conductor 634. The outer conductor 633 can form a continuous structure or separate structures that are configured to connected. Similarly, the inner conductor 634 can form a continuous structure or separate structures that are configured to connected. The outer conductor 633 and/or the inner conductor 634 can be formed at least partially of a conductive material, such as a metal (e.g., copper, steel, stainless steel, etc.).

In the example of FIGS. 6A and 6B, the inner conductor 634 extends along a center axis 643 of the outer conductor 633. That is, the inner conductor 634 is concentric with the outer conductor 633. In other examples, the inner conductor 634 can be offset from the center axis 643. The inner conductor 634 can have any length, which can be different than a length of the outer conductor 633 or the same. In this example, the inner conductor 634 includes a cylindrical elongated form. However, other forms can be used. The outer conductor 633 of the transmitting portion 631 can include a dielectric material 635 disposed therein.

The outer conductor 633 and/or the inner conductor 634 of the resonating portion 632 can form a cavity 636 (also referred to as the "resonator cavity 636"). The cavity 636 can be used to transmit or collect an electromagnetic signal (e.g., a reflected signal). The cavity 636 can enable electromagnetic waves to reflect back and forth between walls of the cavity 636. In some embodiments, the cavity 636 is hollow cavity. However, in some examples the cavity 636 can be at least partially filled with a material, such as a non-conducting material. In one example, the cavity 636 is at least partially filled with a sponge-like material that enables a liquid to be absorbed into the cavity 636, while blocking other substances. A length 644 of the cavity 636 can define a sensing depth of the sensor 630.

In some embodiments, an absorptive material 637 (also referred to as the "electrically absorptive material 637") can be disposed at an interface between the dielectric material 635 of the transmitting portion 631 and the cavity 636 of the resonating portion 632. The absorptive material 637 can be disposed between the outer conductor 633 and the inner conductor 634. The absorptive material 637 can serve to absorb at least a portion of electromagnetic signals incident thereon to isolate or shield the cavity 636. The absorptive material 637 can have a predetermined thickness. In some embodiments, a thickness of the absorptive material 637 can be less than a length 644 of the cavity 636. The absorptive material 637 can be represented as a resistor in some examples. Although the absorptive material 637 is illustrated here, in other examples the absorptive material 637 can be replaced with a surface mount resistor or another component. In some embodiments, the absorptive material 637 can block a sample from penetrating into the dielectric material 635 of the transmitting portion 631.

In some embodiments, the sensor 630 can include slots 660 (e.g., radial openings/breaks) formed (e.g., cut) in the outer conductor 633 of the resonating portion 632 at or near the distal end 645 thereof. The sensor 630 can include any number of slots 660 formed in the outer conductor 633. The slot(s) 660 can allow for flow of a sample into and/or out of the cavity 636 of the resonating portion 632 when the resonating portion 632 is disposed at least partially therein. This may ultimately lead to a more accurate measurement of a constituent in a sample. In some embodiments, the slots 660 can allow a greater amount of flow into the cavity 636 compared to a sensor that does not include such slots. The slots 660 can generally structurally provide empty space in circumferential and/or axial regions of the outer conductor 633. However, in some implementations, a material, such as a non-conducting material (e.g., dielectric), can be disposed within at least a portion of one or more of the slots 660.

As illustrated in FIG. 6B, each slot 660 can be defined by an axial length 672 and an arc/circumferential width 671. In the example illustrated, the length 672 of each slot 660 is the same as a length of the resonating portion 632. That is, each slot 660 can extend axially from a distal end of the resonating portion 632 (e.g., an end that contacts a sample) to a proximal end of the resonating portion 632 (e.g., an end adjacent to the absorptive material 637). However, in other examples the length 672 of each slot 660 can be different, such as shorter in length than the resonating portion 632, longer in length than the resonating portion 632 (e.g., extending into the transmitting portion 631, etc.

The slots 660 can be separated from each other around a circumference of the outer conductor 633 by an arc/circumferential distance 670. The arc distance 670 can be the same or different for adjacent slots 660. For example, the slots 660 can be equally spaced around the circumference/perimeter of the outer conductor 633, or the slots 660 can be spaced around the outer conductor 633 with different distances.

In some embodiments, the sensor 630 can be designed for various applications or contexts. That is, one or more dimensions of the sensor 630 can be designed for a specific application. For example, any of the following dimensions can be adjusted: a length 638 of the transmitting portion 631, a length 639 of the resonating portion 632, a diameter 640 of an inner surface of the outer conductor 633, a diameter 641 of the inner conductor 634, the length 644 of the cavity 636, a length of the sensor 630 (which includes the length 638 and the length 639), a distance between an inner surface of the outer conductor 633 and an outer surface of the inner conductor 634, a thickness of the outer conductor 633 (e.g., a radial thickness), the axial length 672, the arc width 671, the arc distance 670 between adjacent slots 660, etc. Any of such dimensions can be tuned to achieve a desired performance metric.

An end 642 of the sensor 630 can be an interface to connect to control circuitry (not illustrated) or another device. The end 642 can be a proximal end of the sensor 630 to the control circuitry and an end 645 can be a distal end of the sensor 630 to the control circuitry. In some embodiments, the end 642 of the sensor 630 can be connected to one or more interface components, such as the one or more interface components 460 of FIG. 4. Additionally or alternatively, the end 642 of the sensor 630 can be connected to other layers, structures, and/or features that can be implemented to use the sensor 630. In some embodiments, the sensor 630 can be constructed at least partially with a transmission line structure, such as a coaxial transmission line.

Figure 7:
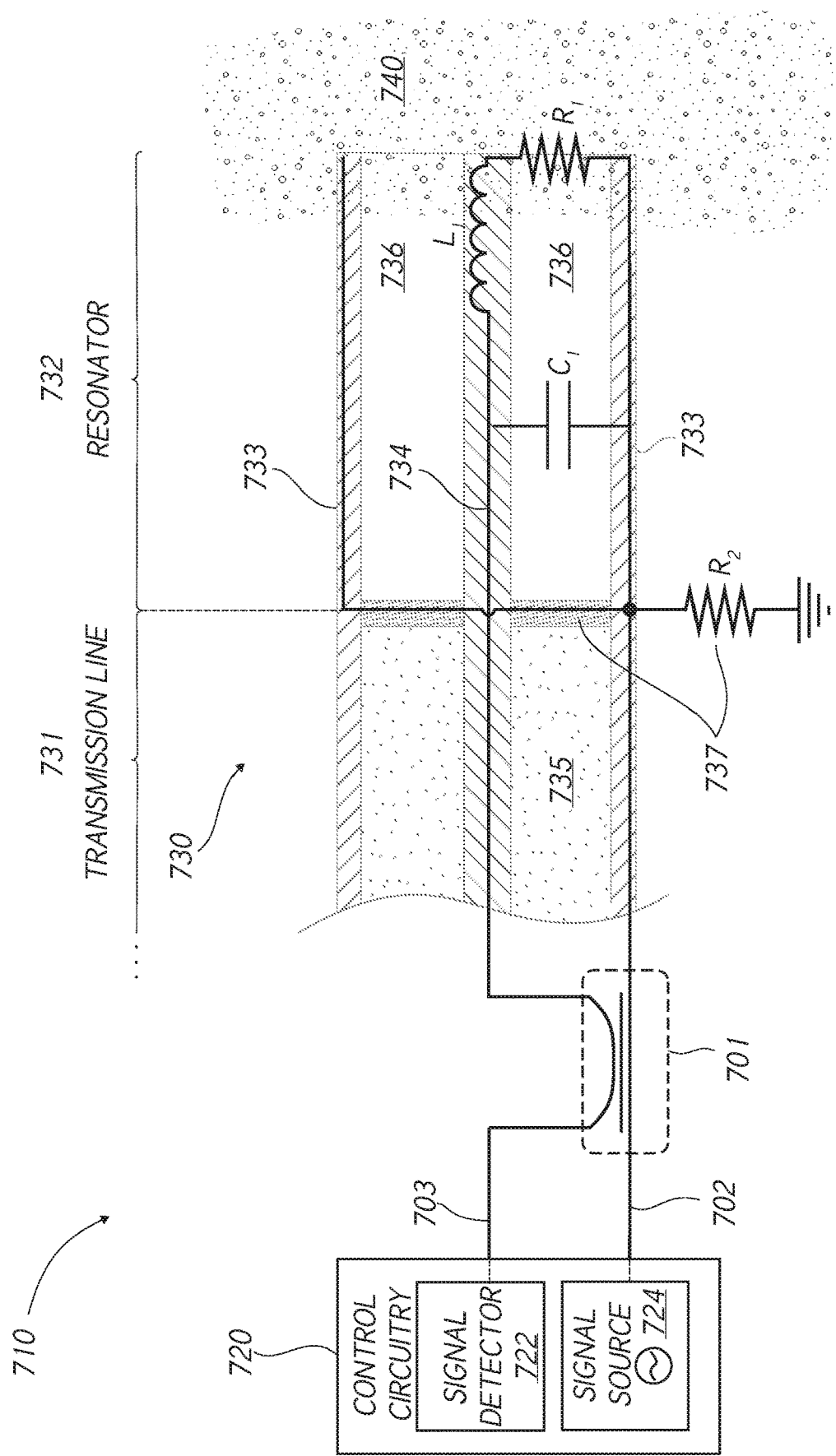
FIG. 7 provides a schematic block diagram representing a system for sensing constituents in a sample in accordance with one or more embodiments of the present disclosure.

For illustrative purposes, FIG. 7 provides a schematic block diagram representing a system 710 for sensing constituents in a sample 740 in accordance with one or more embodiments of the present disclosure. For example, the illustrated circuit representations of various components and features may be understood to be representative of electrical functionality associated with certain components or portions of a sensor in accordance with certain embodiments of the present disclosure.

For example, as with various embodiments illustrated and disclosed in connection with the present disclosure, FIG. 7 shows a sensor 730 including a resonating portion 732 (also referred to as the "resonator 732") and a transmitting portion 731 (also referred to as the "transmission line 731"). Some of the illustrated circuitry is shown overlaying various components or portions of the illustrated sensor 730 for purposes of illustration. However, it should be understood, that embodiments of the present disclosure may have any suitable or desirable electrical characteristics and may operate according to electrical principles and features that are different in one or more respects than that illustrated in FIG. 7.

FIG. 7 further shows block diagram representation of control circuitry 720, which includes, in addition to other functional circuitry and components not illustrated for the sake of simplicity in FIG. 7, signal source circuitry 724 and signal detector circuitry 722. Although the signal source circuitry 724 and the signal detector circuitry 722 are illustrated as separate blocks in the diagram of FIG. 7, it should be understood that in some embodiments, such functional circuitry may be embodied in a single device, chip, or other partition or circuitry.

In some implementations, the signal source circuitry 724 of the control circuitry 720 may be configured to generate electromagnetic signals, wherein such signals may be provided on connectivity circuitry 702 to one or more conductors or portions of the sensor 730. For example, in some embodiments, the generated electromagnetic signals (e.g., radiofrequency signals) may be transmitted on connectivity circuitry and/or conduction path(s) 702 that are electrically coupled to, either directly or indirectly, one or more outer conductors 733 of the sensor 730. Although certain description herein describes transmitted signals from the control circuitry 720 as being provided primarily on the outer conductor(s) 733, in some embodiments such signals may be transmitted primarily on one or more inner conductor 734, as described herein. The various conductors of the sensor 730 can comprise copper, silver, stainless steel, gold, and/or any other suitably conductive material.

In some embodiments, the outer conductor(s) 733 and/or the inner conductor(s) 734 may be in contact with, or otherwise electrically coupled at least in part to, an absorbing material 737, which may serve to effectively shunt some amount of electrical signal present on such conductors to a ground or other reference. The form of absorbing material 737 may be disc- or washer-shaped, with a central hole or aperture generally accommodating the presence of the inner conductor 734. The functionality of the signal-absorbing material 737 may be embodied in and/or represented at least in part by an electrical coupling between one or more conductors of the sensor 730 and a ground reference, wherein the signal-absorbing material 737 has certain resistive characteristics that can be represented as shown in the diagram of FIG. 7 as a resistance $R_2$. In some embodiments, the sensor 730 does not comprise signal-absorbing material 737, but rather includes an electrical connection between one or more conductors of the sensor 730 and a resistance (e.g., one or more surface mount resistor devices and/or resistor forms formed in one or more layers of a circuit board or other substrate), which may be coupled to a reference node/connection, such as a ground reference.

The control circuitry 720 advantageously utilizes the signal source circuitry 724 to provide probing signals to the resonator 732 of the sensor 730. The signal source circuitry 724 may be configured to generate probing signals using an oscillator (e.g., voltage-controlled oscillator). The resonator 732 of the sensor 730 may be represented at least in part by the circuitry shown in the portion 732 of the diagram of FIG. 7. In coaxial embodiments, as described in detail herein, wherein an inner conductor 734 is disposed coaxially with an outer conductor 733, the inner conductor 734 may be electrically coupled to some degree with the outer conductor(s) 733 via a capacitance that may exist inherently between the conductors 734, 733. The diagram of FIG. 7 illustrates such capacitance as the capacitor $C_1$. Although a single capacitor element $C_1$ is illustrated in the diagram FIG. 7, it should be understood that the capacitance represented thereby may exist at least in part between the inner conductor 734 and one or more circumferential regions of a cylindrically-shaped outer conductor 733. Generally, the dimensions and/or configuration of the inner conductor 734 may determine at least in part an inductance (e.g., parasitic inductance) that may be provided by at least a portion of the inner conductor 734. Such inductance associated with the inner conductor 734 is conveniently represented in the diagram of FIG. 7 has an inductance Li, which is illustrated as being electrically coupled to the inner conductor 734.

Generally, when the cavity 736 in the resonator 732 of the sensor 730 is not filled with sample media or other substance, that is, when the cavity 736 is filled at least partially with air, the electrical resistance between the inner conductor 734 and the outer conductor 733 may be considered to be relatively high, such that a circuit representation of the resonator 732 may practically represent such resistance as an open circuit. However, when the resonator 732 becomes submerged in, or otherwise contacts or comes within close proximity to, target sample media 740, such media may serve to at least partially electrically bridge the inner conductor 734 to the outer conductor 733. For example, where the sample media 740 comprises liquid, such as blood and/or water, such media may present a substantially lower electrical resistance than air, such that the electrical path between the inner conductor 734 and the outer conductor 733 may be represented by an electrical connection associated with a resistance $R_1$, as illustrated in FIG. 7. The sample media 740 may be permitted to flow into and out of the resonator cavity 736 of the resonator 732 in embodiments comprising slots or other features associated with the resonator 732 configured to allow for the passage of fluid therethrough.

In some embodiments, the present capacitances, inductances, and/or resistances associated with the resonator 732 of the sensor 730 may form, together with one or more of the inner 734 and outer 733 conductors, a resonant circuit (e.g., tank circuit), which may have a tendency to oscillate at a resonant frequency that is determined and/or based at least in part on the values associated with the present capacitances, inductances, and/or resistances. Therefore, attenuation of a signal provided on one or more of the inner 734 and outer 733 conductors may be determined and/or based at least in part on the values of the capacitances, inductances, and/or resistances that may be present in the circuit of the resonator 732 of the sensor 730.

The value of the resistance $R_1$ between the inner conductor 734 and the outer conductor 733 can be based on and/or determined at least in part by the material characteristics and/or constituents of the media 740. For example, concentrations of certain constituents in the media 740 may be associated with certain resistance values. Therefore, the attenuation of a signal provided by the signal source 724 on one or more of the inner 734 and outer 733 conductors of the resonator 732 may be based at least in part on the particular characteristics of the sample media 740, such as the presence and/or concentration of certain constituents thereof. The control circuitry 720 may advantageously be configured to make determinations and/or measurements indicative of the resistance $R_1$ associated with the sample media 740 based at least in part on determinations of signal attenuation and/or other changes in parameters or characteristics of a signal provided by the signal source 724, passed through at least a portion of the sample media 740, and detected using the signal detector circuitry 722. Therefore, analysis of reflected signals that have propagated on or through the inner 734 and outer 733 conductors and at least partially through the sample media 740, thereby being subject to the resistance $R_1$ and/or other signal-altering characteristics of the sample media 740, can indicate properties associated with one or more specific constituents of interest of the sample media 740. For example, such analysis can involve evaluation of signal attenuation, phase offset, and/or other characteristics or parameters associated with reflected signals detected by the signal detector 722. The resistance $R_1$ may be due to signal loss in the media 740.

In some embodiments, the signal detector circuitry 722 may utilize circuitry 701, such as a coupler (e.g., directional coupler), a signal separator, a circulator, or the like, to detect reflected signals present on the one or more conductive paths 702, which may be coupled to the inner 734 and/or outer 733 conductors of the sensor 730. Although the circuit illustration and FIG. 7 shows the signal detector circuitry 722 coupled primarily to the inner conductor 734, the signal detector circuitry 722 and/or associated electrical coupling paths 703 may be coupled to any suitable or desirable conductors of the resonator 732, either indirectly or directly. Furthermore, although a coupler 701 is illustrated in FIG. 7, in some embodiments, the signal detector circuitry 722 is coupled directly to the signal line(s) 702.

In some embodiments, the signal detector circuitry 722 can be configured to determine the resonant frequency associated with the sample media 740 by determining a frequency associated with a largest or smallest detected signal amplitude among a plurality of probing signal frequencies over a frequency range. Since the electrical resistance/impedance of the sample can be based at least in part on a concentration of a constituent in the sample, the control circuitry 720 and/or detector circuitry 722 can correlate a detected resonant frequency to a concentration of a compound (e.g., glucose) in the sample to thereby determine or estimate the concentration of the compound in the sample.

Figure 8:
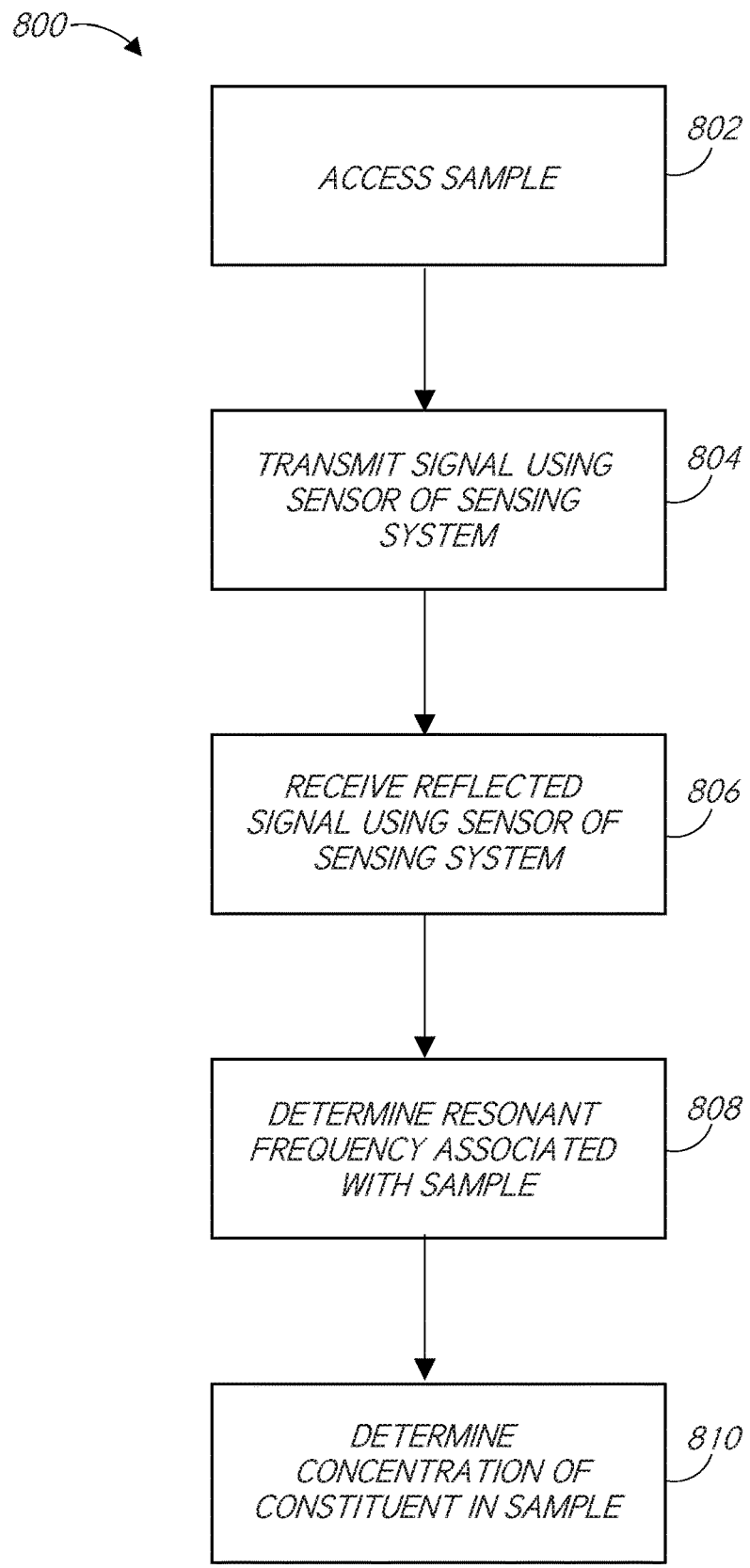
FIG. 8 illustrates an example process for determining a concentration of a constituent in a sample.

FIG. 8 illustrates an example process 800 for determining a concentration of a constituent in a sample. In some embodiments, the process 800 can be implemented at least in part by a sensing system, such as any of the sensing systems discussed herein. In other examples, the process 800 can be performed by other devices and/or systems.

At 802, a sample can be accessed. In some embodiments, a volume of a sample media can be provided. In one example, a sensing system can be inserted into a port of a bioreactor to come into contact with, or proximity of (e.g., within a predetermined distance), a sample located within the bioreactor. In another example, a sensing system can be placed on a surface of human tissue. In yet another example, a sensing system can be placed in proximity or contact to a sample in another type of container.

At 804, a signal can be transmitted using a sensor of a sensing system. For example, control circuitry can cause a signal to be generated and transmitted to the sensor. The sensor can include a transmitting portion that is connected to the control circuitry and can include a resonating portion that is placed in contact with or in proximity to a sample. The signal can propagate through the sensor into the sample. In some embodiments, the control circuitry can transmit multiple signals across a frequency range.

At 806, a reflected signal can be received using a sensor of a sensing system. For example, a resonating portion of the sensor can receive a signal that is reflected from a sample. The reflected signal can propagate through the sensor and return to control circuitry connected to the sensor. In some embodiments, multiple signals associated with different frequencies can be received (e.g., over a period of time as multiple signals are transmitted to the sample).

At 808, a resonant frequency associated with a sample can be determined. For example, control circuitry can analyze properties of multiple reflected signals to determine a resonant frequency. To illustrate, control circuitry can analyze multiple reflected signals to identify a reflected signal that is associated with a lowest (or highest) amplitude/magnitude.

At 810, a concentration of a constituent in a sample can be determined. For example, control circuitry can determine a concentration of a constituent in a sample based on a resonant frequency that is determined for the sample. In some embodiments, the control circuitry can correlate a resonant frequency to a concentration of a constituent. To illustrate, if a sample is associated with a first resonant frequency at a first time, a first concentration can be determined for the sample. If the sample is then associated with a second resonant frequency at a second time, a second concentration can be determined for the sample. In some embodiments, a concentration of a constituent in a sample changes proportionally or inversely proportional to a resonant frequency associated with the sample (e.g., linearly proportional, etc.). In some embodiments, a resonant frequency can be correlated to a dielectric constant of a material, and a dielectric constant can change as a concentration of a constituent changes.

In some embodiments, the process 800 can determine a concentration of a constituent in a sample in a non-destructive manner (e.g., in a way that maintains a sample in its initial state).

Figure 9A:
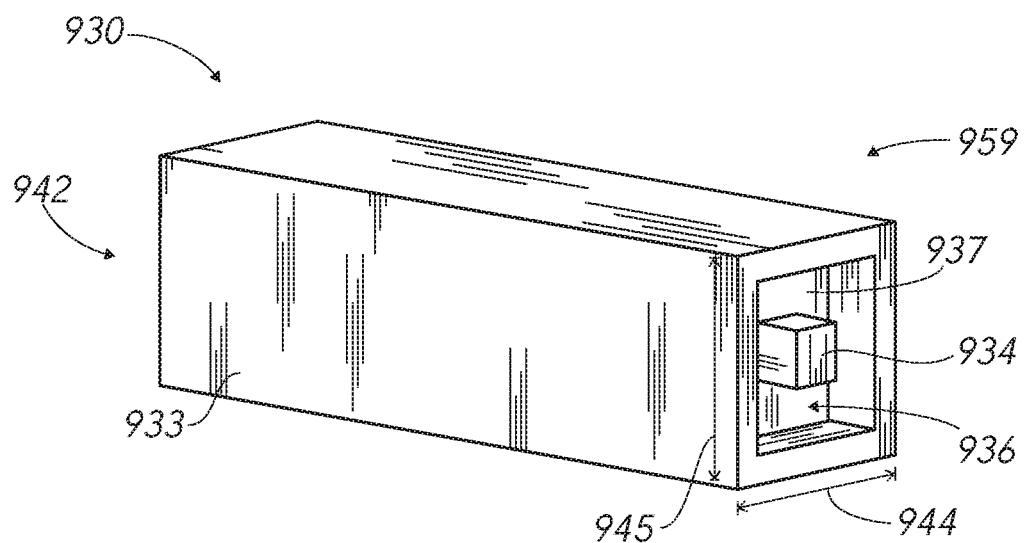
FIG. 9A illustrates a perspective view of an example sensor that has a hyperrectangular shape.
Figure 9B:
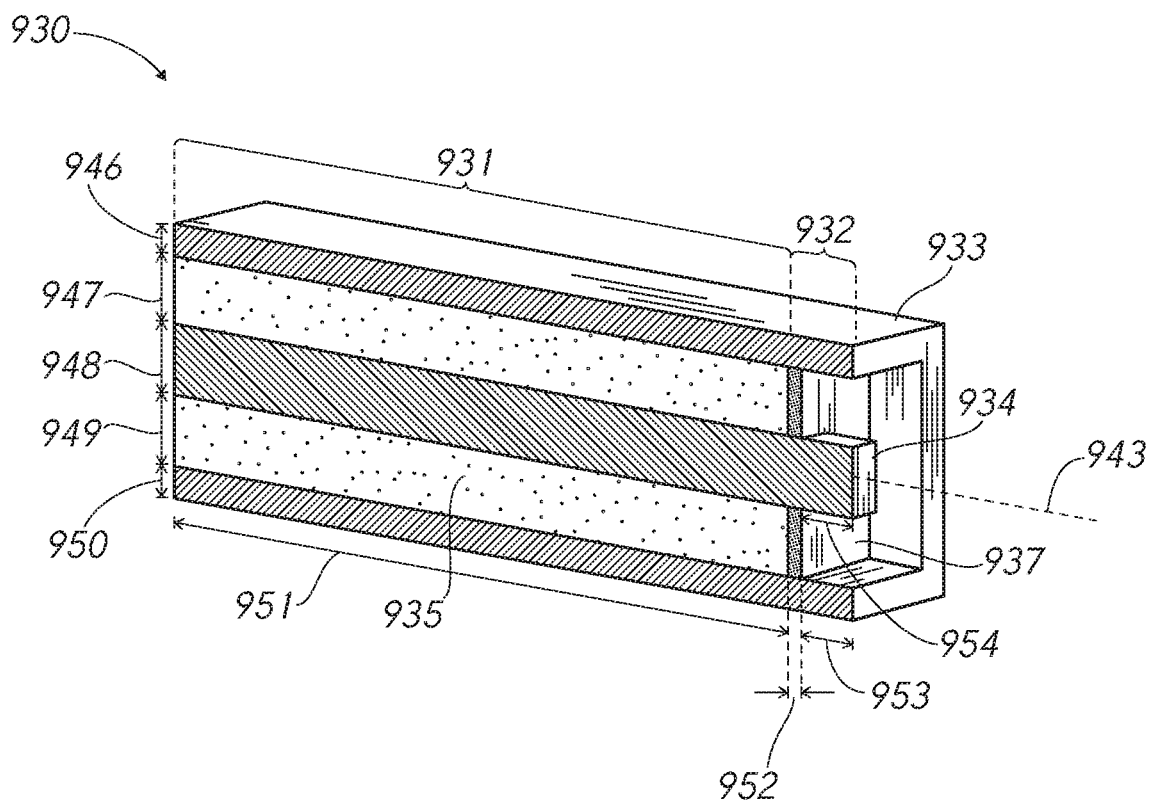
FIG. 9B illustrates a cross-sectional perspective view of the sensor shown in FIG. 9A.

FIGS. 9A-9B illustrate an example sensor 930 that has a hyperrectangular shape. FIG. 9A shows a perspective view of the sensor 930, while FIG. 9B shows a cross-sectional perspective view of the sensor 930. The sensor 930 represents an example embodiment of a sensor device/system (or component/portion thereof) that can be implemented in the various example devices and systems disclosed herein.

As illustrated, the sensor 930 can include a transmitting portion 931 and a resonating portion 932. The transmitting portion 931 and/or the resonating portion 932 can include an outer conductor 933 and/or an inner conductor 934. The inner conductor can extend along a center axis 943 of the outer conductor 933. However, in other examples the inner conductor 934 can be offset from the center axis 943.

The outer conductor 933 of the transmitting portion 931 can include a dielectric material 935 disposed therein. Further, the outer conductor 933 and/or the inner conductor 934 of the resonating portion 932 can form a cavity 936. The outer conductor 933 can be formed of a continuous structure or separate structures for the transmitting portion 931 and the resonating portion 932. If separate structures are implemented, the structures can be configured to be connected. Similarly, the inner conductor 934 can form a continuous structure or separate structures that are configured to connected. An absorptive material 937 can be disposed at an interface between the dielectric material 935 and the cavity 936.

The sensor 930 can be connected to control circuitry at a first end 942 of the sensor 930 (e.g., an interface end of the sensor 930). The sensor 930 can be placed in proximity to or contact with a sample at a second end 959 of the sensor 930. In this example, the resonating portion 932 of the sensor 930 includes a substantially square-shaped profile (e.g., a transverse cross-section of the sensor 930 has a substantially square shape, providing a square shaped resonator cavity). In some embodiments, a length 953 defines a sensing depth of the resonating portion 932.

In some embodiments, the sensor 930 can be designed for various contexts. That is, one or more dimensions of the sensor 930 can be designed for any number of applications. A dimension of the sensor 930 can include: a depth 944 of the sensor 930, a height 945 of the sensor 930, an upper thickness 946 of the outer conductor 933, a first distance 947 of the dielectric material 935 between an upper inner surface of the outer conductor 933 and an upper surface of the inner conductor 934, a height 948 of the inner conductor 934, a second distance 949 of the dielectric material 935 between a lower inner surface of the outer conductor 933 and a lower surface of the inner conductor 934 (the second distance 949 can be the same as or different than the first distance 947), a lower thickness 950 of the outer conductor 933 (the lower thickness 950 can be the same as or different than the upper thickness 946), a length 951 of the dielectric material 935 from the first end of the sensor 930 to the absorptive material 937, a thickness 952 of the absorptive material 937, the length 953 of the cavity 936, a length 954 of the inner conductor 934 that extends into the cavity 936, the length of the sensor 930 (which can include the length 951, the thickness 952, and the length 953), a length of the transmitting portion 931 (which can include or exclude the thickness 952 of the absorptive material 937), a length of the resonating portion 932 (which can include or exclude the thickness 952 of the absorptive material 937), etc.

Figure 10A:
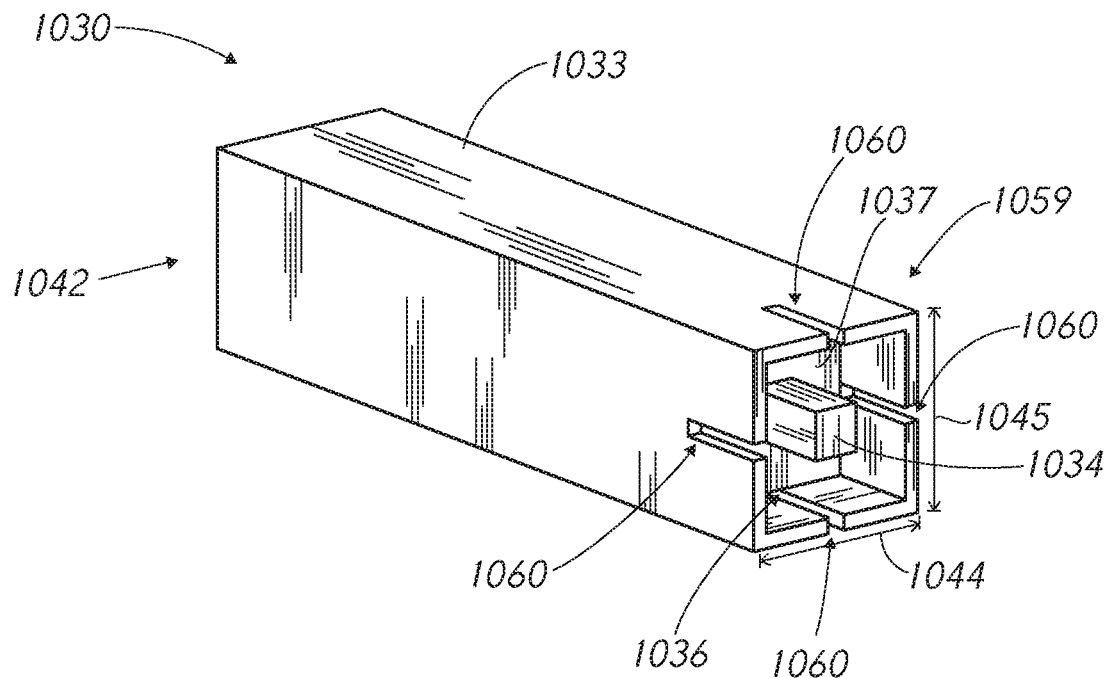
FIG. 10A illustrates a perspective view of an example sensor that has a hyperrectangular shape and slots.
Figure 10B:
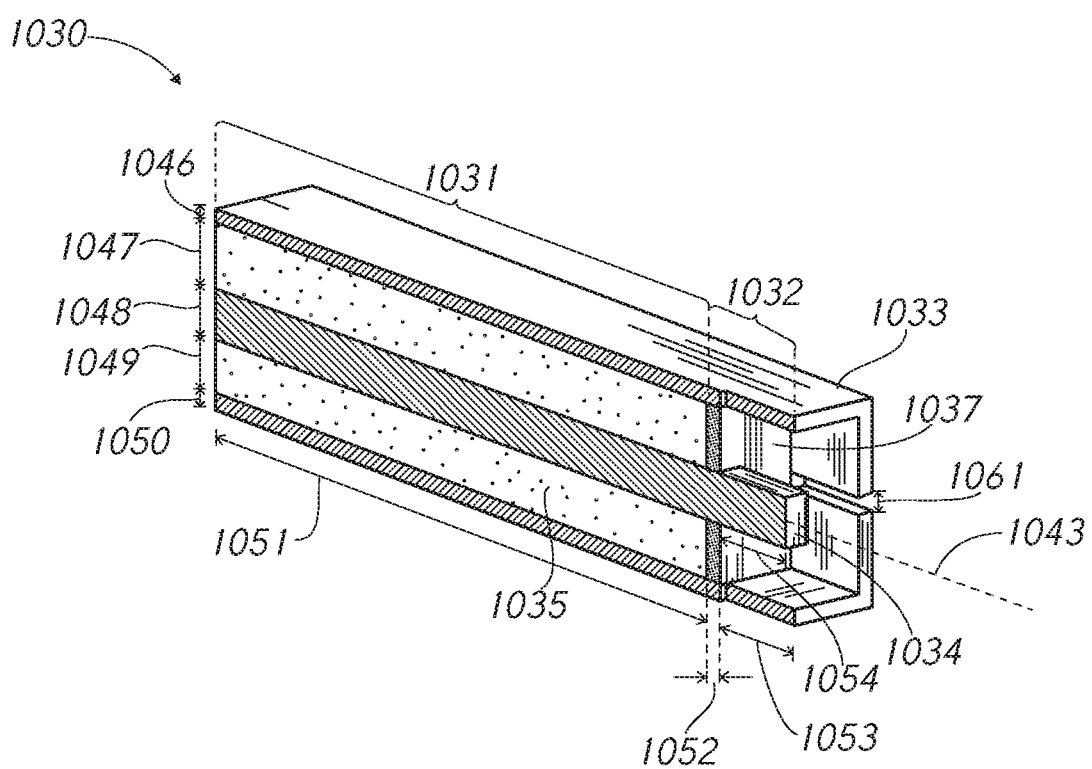
FIG. 10B illustrates a cross-sectional perspective view of the sensor shown in FIG. 10A.

FIGS. 10A-10B illustrate an example sensor 1030 that has a hyperrectangular shape and slots. FIG. 10A shows a perspective view of the sensor 1030, while FIG. 10B shows a cross-sectional perspective view of the sensor 1030. The sensor 1030 represents an example embodiment of a sensor device/system (or component/portion thereof) that can be implemented in the various example devices and systems disclosed herein.

As illustrated, the sensor 1030 can include a transmitting portion 1031 and a resonating portion 1032. The transmitting portion 1031 and/or the resonating portion 1032 can include an outer conductor 1033 and/or an inner conductor 1034. The inner conductor 1034 can extend along a center axis 1043 of the outer conductor 1033. However, in other examples the inner conductor 1034 can be offset from the center axis 1043.

The outer conductor 1033 of the transmitting portion 1031 can include a dielectric material 1035 disposed therein. Further, the outer conductor 1033 and/or the inner conductor 1034 of the resonating portion 1032 can form a cavity 1036.

The outer conductor 1033 can be formed of a continuous structure or separate structures for the transmitting portion 1031 and the resonating portion 1032. If separate structures are implemented, the structures can be configured to be connected. Similarly, the inner conductor 1034 can form a continuous structure or separate structures that are configured to connected. An absorptive material 1037 can be disposed at an interface between the dielectric material 1035 and the cavity 1036.

The sensor 1030 can be connected to control circuitry at a first end 1042 of the sensor 1030 (e.g., an interface end of the sensor 1030). The sensor 1030 can be placed in proximity to or contact with a sample at a second end 1059 of the sensor 1030. In this example, the resonating portion 1032 of the sensor 1030 includes a substantially square-shaped profile (e.g., a transverse cross-section of the sensor 1030 has a substantially square shape, providing a square shaped resonator cavity). In some embodiments, a length 1053 defines a sensing depth of the resonating portion 1032.

In some embodiments, the sensor 1030 can include slots 1060 formed in the outer conductor 1033 of the resonating portion 1033. This can allow flow of a sample into or out of the cavity 1036 of the resonating portion 1032. This may ultimately lead to a more accurate measurement of a constituent in a sample. In some embodiments, the slots 1060 can allow a larger amount of flow into the cavity 1036 than a sensor that does not include such slots. The slots 1060 can generally include empty space. However, in some examples a material, such as a non-conducting material, can be disposed within the slots 1060. Each of the slots 1060 can extend from the second end 1059 of the sensor 1030 to the absorptive material 1037. As such, each of the slots 1060 can have a length that corresponds to the length 1053 of the cavity 1036, or a different length in some embodiments. Each of the slots 1060 can also have a height 1061.

In some embodiments, the sensor 1030 can be designed for various contexts. That is, one or more dimensions of the sensor 1030 can be designed for any number of applications. A dimension of the sensor 1030 can include: a depth 1044 of the sensor 1030, a height 1045 of the sensor 1030, an upper thickness 1046 of the outer conductor 1033, a first distance 1047 of the dielectric material 1035 between an upper inner surface of the outer conductor 1033 and an upper surface of the inner conductor 1034, a height 1048 of the inner conductor 1034, a second distance 1049 of the dielectric material 1035 between a lower inner surface of the outer conductor 1033 and a lower surface of the inner conductor 1034 (the second distance 1049 can be the same as or different than the first distance 1047), a lower thickness 1050 of the outer conductor 1033 (the lower thickness 1050 can be the same as or different than the upper thickness 1046), a length 1051 of the dielectric material 1035 from the first end of the sensor 1032 to the absorptive material 1037, a thickness 1052 of the absorptive material 1037, the length 1053 of the cavity 1036, a length 1054 of the inner conductor 1034 that extends into the cavity 1036, the length of the sensor 1030 (which can include the length 1051, the thickness 1052, and the length 1053), the height 1061 of the slot 1060, a length of the slot 1060, a length of the transmitting portion 1031 (which can include or exclude the thickness 1052 of the absorptive material 1037), a length of the resonating portion 1032 (which can include or exclude the thickness 1052 of the absorptive material 1037), etc.

Figure 11A:
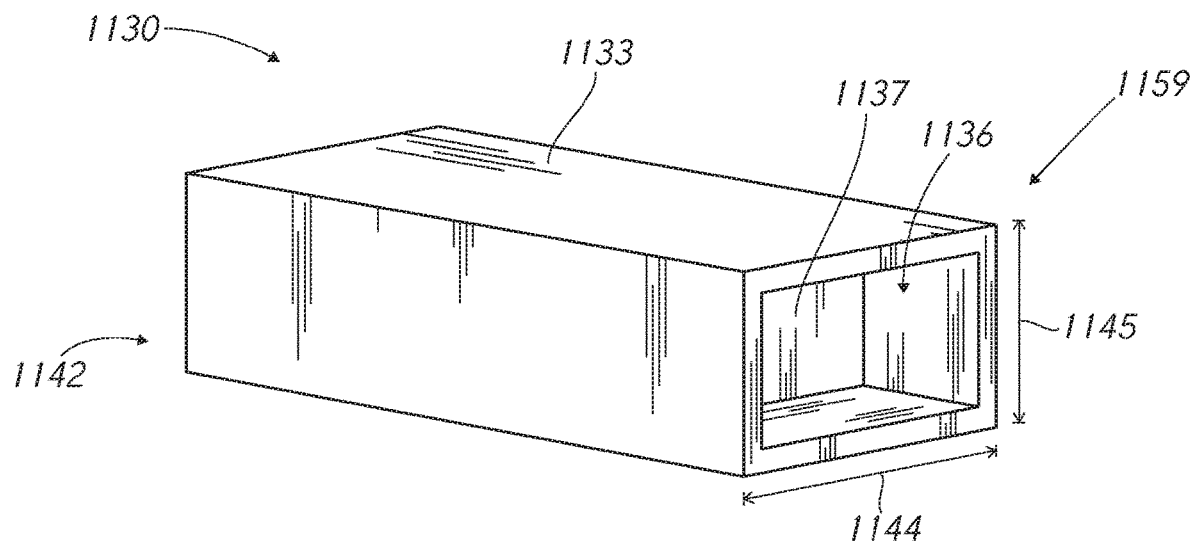
FIG. 11A illustrates a perspective view of an example sensor that has a hyperrectangular shape.
Figure 11B:
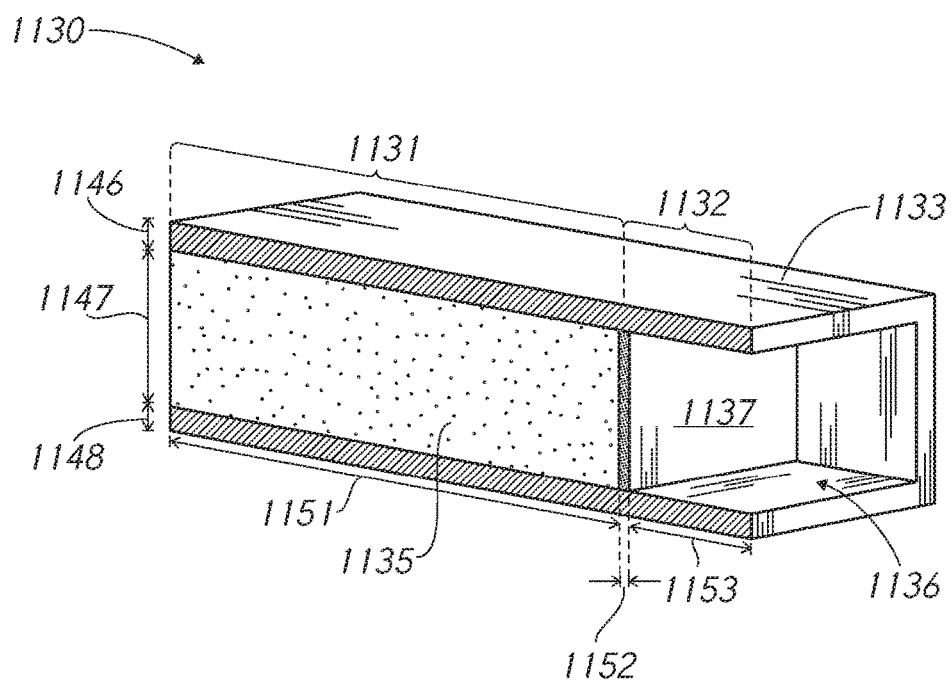
FIG. 11B illustrates a cross-sectional perspective view of the sensor shown in FIG. 11A.

FIGS. 11A-11B illustrate an example sensor 1130 that has a hyperrectangular shape. FIG. 11A shows a perspective view of the sensor 1130, while FIG. 11B shows a cross-sectional perspective view of the sensor 1130. In this example, the sensor 1130 is implemented without an inner conductor. The sensor 1130 can be representative of a waveguide-type sensor. The sensor 1130 represents an example embodiment of a sensor device/system (or component/portion thereof) that can be implemented in the various example devices and systems disclosed herein.

As illustrated, the sensor 1130 can include a transmitting portion 1131 and a resonating portion 1132. The transmitting portion 1131 and/or the resonating portion 1132 can include an outer conductor 1133. The outer conductor 1133 of the transmitting portion 1131 can include a dielectric material 1135 disposed therein. Further, the outer conductor 1133 of the resonating portion 1132 can form a cavity 1136. The outer conductor 1133 can be formed of a continuous structure or separate structures for the transmitting portion 1131 and the resonating portion 1132. If separate structures are implemented, the structures can be configured to be connected. An absorptive material 1137 can be disposed at an interface between the dielectric material 1135 and the cavity 1136.

The sensor 1130 can be connected to control circuitry at a first end 1142 of the sensor 1130 (e.g., an interface end of the sensor 1130). The sensor 1130 can be placed in proximity to or contact with a sample at a second end 1159 of the sensor 1130. In this example, the resonating portion 1132 of the sensor 1130 includes a substantially rectangular profile (e.g., a transverse cross-section of the sensor 1130 has a substantially rectangular shape, providing a rectangular-shaped resonator cavity). In some embodiments, a length 1153 defines a sensing depth of the resonating portion 1132.

In some embodiments, the sensor 1130 can be designed for various contexts. That is, one or more dimensions of the sensor 1130 can be designed for any number of applications. A dimension of the sensor 1130 can include: a depth 1144 of the sensor 1130, a height 1145 of the sensor 1130, an upper thickness 1146 of the outer conductor 1133, a height 1147 of the dielectric material 1135 between an upper inner surface of the outer conductor 1133 and a lower inner surface of the outer conductor 1133, a lower thickness 1150 of the outer conductor 1133 (the lower thickness 1150 can be the same as or different than the upper thickness 1146), a length 1151 of the dielectric material 1135 from the first end 1142 of the sensor 1130 to the absorptive material 1137, a thickness 1152 of the absorptive material 1137, the length 1153 of the cavity 1136, the length of the sensor 1130 (which can include the length 1151, the thickness 1152, and the length 1153), a length of the transmitting portion 1131 (which can include or exclude the thickness 1152 of the absorptive material 1137), a length of the resonating portion 1132 (which can include or exclude the thickness 1152 of the absorptive material 1137), etc.

Figure 12A:
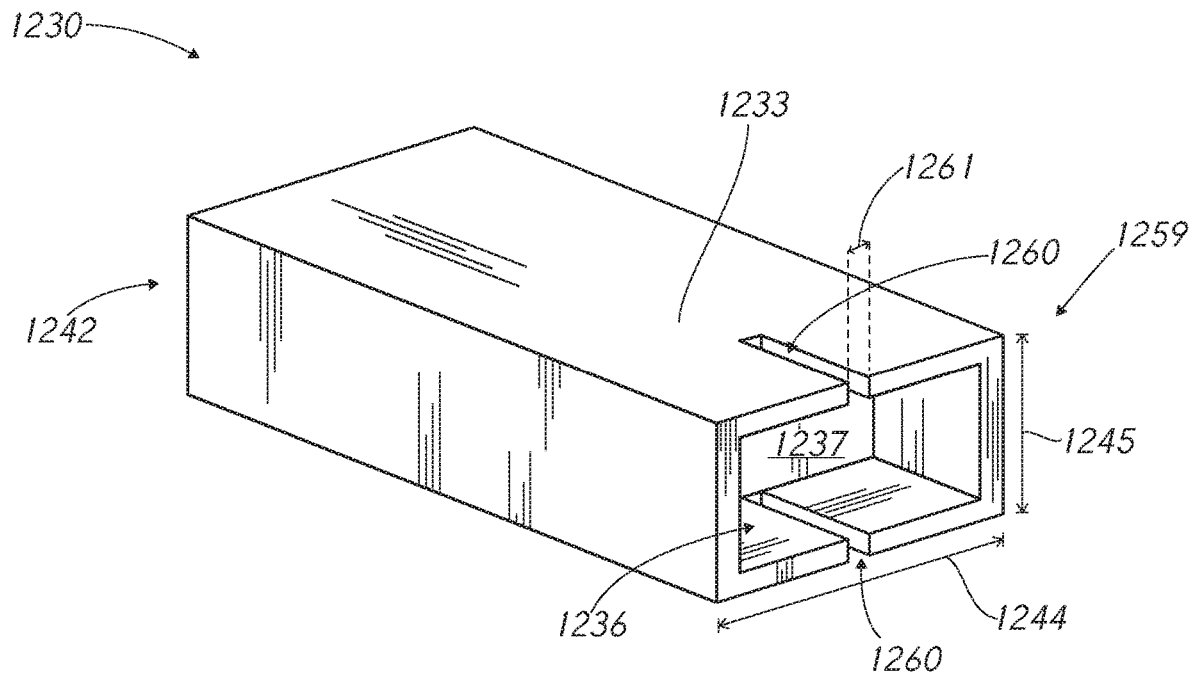
FIG. 12A illustrates a perspective view of an example sensor that has a hyperrectangular shape and slots.
Figure 12B:
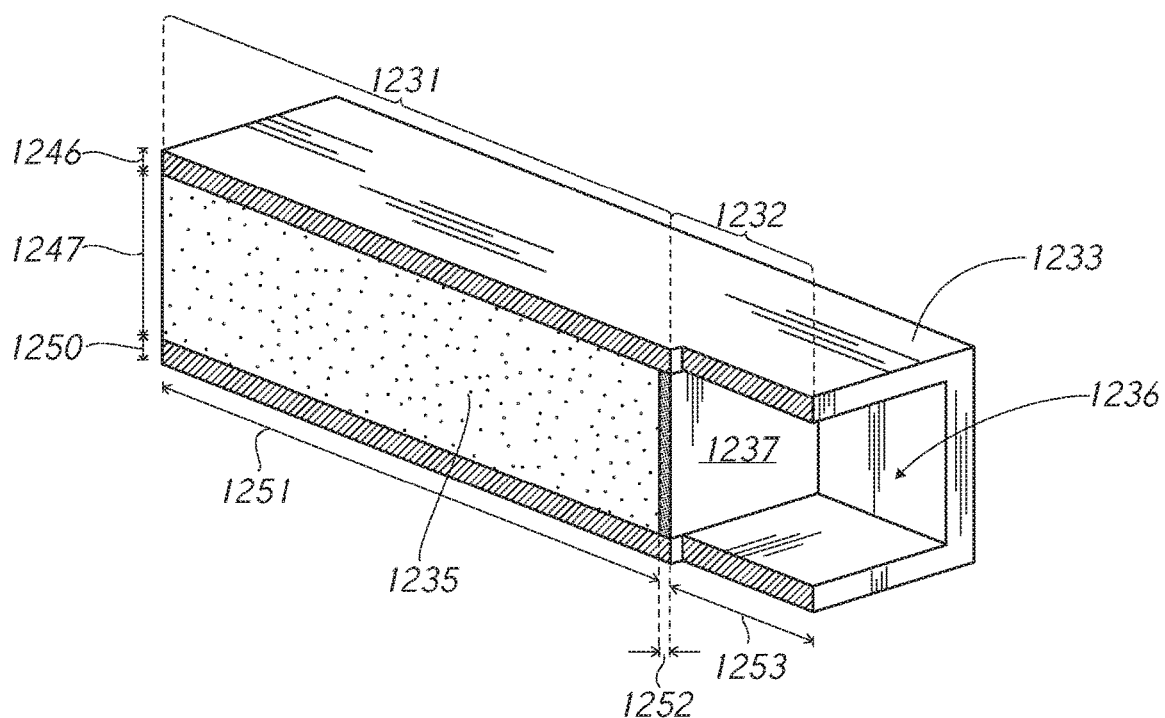
FIG. 12B illustrates a cross-sectional perspective view of the sensor shown in FIG. 12A.

FIGS. 12A-12B illustrate an example sensor 1230 that has a hyperrectangular shape and slots. FIG. 12A shows a perspective view of the sensor 1230, while FIG. 12B shows a cross-sectional perspective view of the sensor 1230. In this example, the sensor 1230 is implemented without an inner conductor. The sensor 1230 can be representative of a waveguide-type sensor. The sensor 1230 represents an example embodiment of a sensor device/system (or component/portion thereof) that can be implemented in the various example devices and systems disclosed herein.

As illustrated, the sensor 1230 can include a transmitting portion 1231 and a resonating portion 1232. The transmitting portion 1231 and/or the resonating portion 1232 can include an outer conductor 1233. The outer conductor 1233 of the transmitting portion 1231 can include a dielectric material 1235 disposed therein. Further, the outer conductor 1233 of the resonating portion 1232 can form a cavity 1236. The outer conductor 1233 can be formed of a continuous structure or separate structures for the transmitting portion 1231 and the resonating portion 1232. If separate structures are implemented, the structures can be configured to be connected. An absorptive material 1237 can be disposed at an interface between the dielectric material 1235 and the cavity 1236.

The sensor 1230 can be connected to control circuitry at a first end 1242 of the sensor 1230 (e.g., an interface end of the sensor 1230). The sensor 1230 can be placed in proximity to or contact with a sample at a second end 1259 of the sensor 1230. In this example, the resonating portion 1232 of the sensor 1230 includes a substantially rectangular-shaped profile (e.g., a transverse cross-section of the sensor 1230 has a substantially rectangular shape, providing a rectangular shaped resonator cavity). In some embodiments, a length 1253 defines a sensing depth of the resonating portion 1232.

In some embodiments, the sensor 1230 can include slots 1260 formed in the outer conductor 1233 of the resonating portion 1233. This can allow flow of a sample into or out of the cavity 1236 of the resonating portion 1232. This may ultimately lead to a more accurate measurement of a constituent in a sample. In some embodiments, the slots 1260 can allow a larger amount of flow into the cavity 1236 than a sensor that does not include such slots. The slots 1260 can generally include empty space. However, in some examples a material, such as a non-conducting material, can be disposed within the slots 1260. Each of the slots 1260 can extend from the second end 1259 of the sensor 1230 to the absorptive material 1237. As such, each of the slots 1260 can have a length that corresponds to the length 1253 of the cavity 1236, or a different length in some embodiments. Each of the slots 1260 can also have a depth 1261.

In some embodiments, the sensor 1230 can be designed for various contexts. That is, one or more dimensions of the sensor 1230 can be designed for any number of applications. A dimension of the sensor 1230 can include: a depth 1244 of the sensor 1230, a height 1245 of the sensor 1230, an upper thickness 1246 of the outer conductor 1233, a height 1247 of the dielectric material 1235 between an upper inner surface of the outer conductor 1233 and a lower inner surface of the outer conductor 1233, a lower thickness 1250 of the outer conductor 1233 (the lower thickness 1250 can be the same as or different than the upper thickness 1246), a length 1251 of the dielectric material 1235 from the first end 1242 of the sensor 1230 to the absorptive material 1237, a thickness 1252 of the absorptive material 1237, the length 1253 of the cavity 1236, the length of the sensor 1230 (which can include the length 1251, the thickness 1252, and the length 1253), the depth 1261 of a slot 1260, a length of a slot 1260, a length of the transmitting portion 1231 (which can include or exclude the thickness 1252 of the absorptive material 1237), a length of the resonating portion 1232 (which can include or exclude the thickness 1252 of the absorptive material 1237), etc.

Figure 13A:
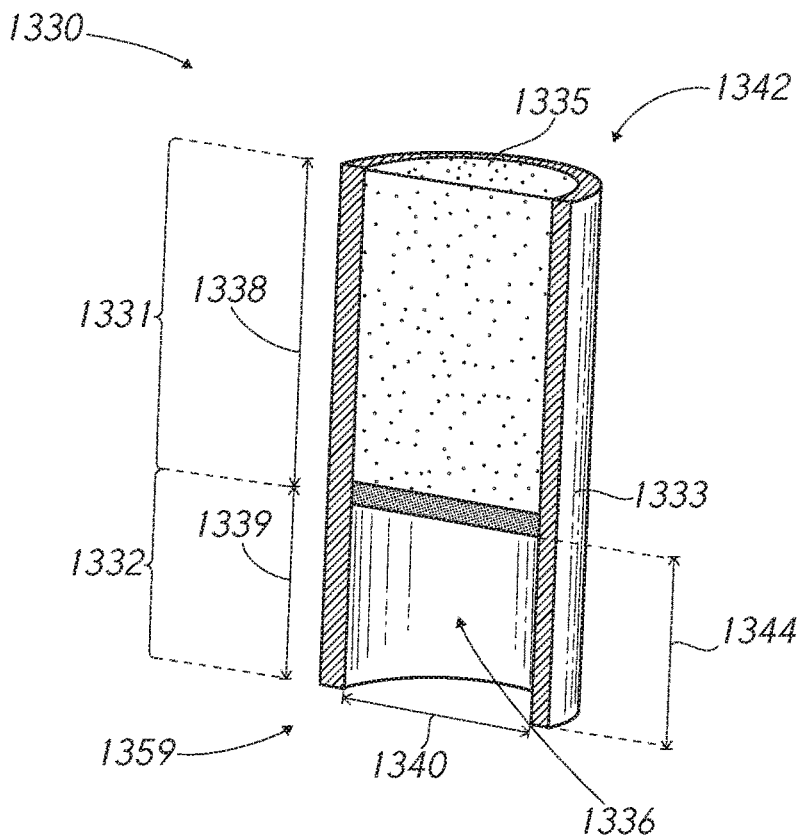
FIG. 13A illustrates a perspective cross-sectional view of an example sensor that has a substantially cylindrical shape and no inner conductor.
Figure 13B:
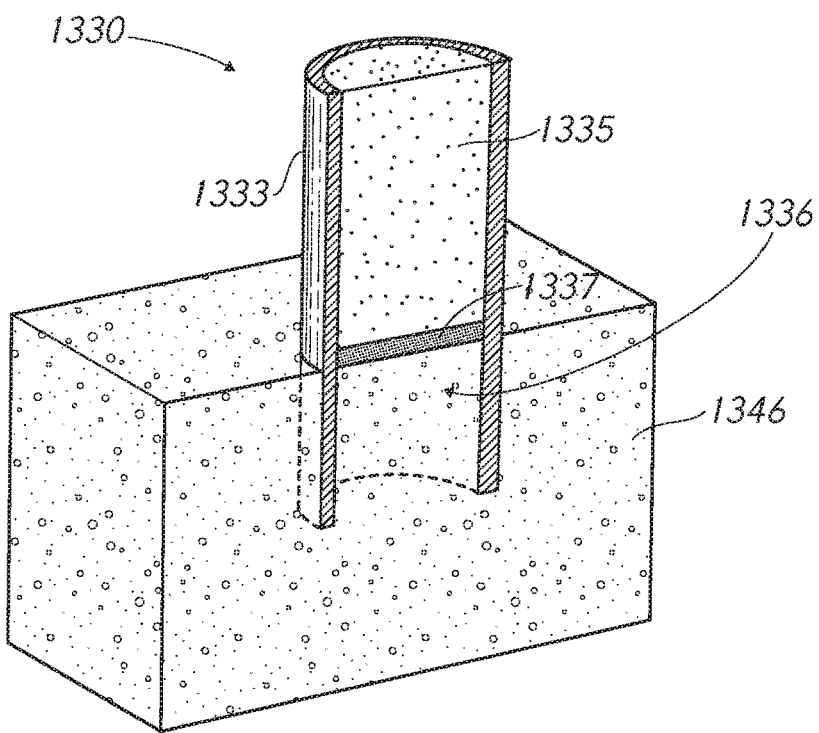
FIG. 13B illustrates a perspective cross-sectional view of the sensor shown in FIG. 13A, wherein a resonating portion thereof is disposed at least partially within sample media.

FIGS. 13A-13B illustrate an example sensor 1330 that has a substantially cylindrical shape. FIGS. 13A-13B show cross-sectional views of the sensor 1330. In this example, the sensor 1330 is implemented without an inner conductor. FIG. 13B shows a perspective view of the sensor 1330 shown in FIG. 13A, wherein a resonating portion 1332 thereof is disposed at least partially within a sample 1346, as shown. The sensor 1330 represents an example embodiment of a sensor device/system (or component/portion thereof) that can be implemented in the various example devices and systems disclosed herein.

The sensor 1330 includes a transmitting portion 1331 and the resonating portion 1332. The transmitting portion 1331 and/or the resonating portion 1332 can include an outer conductor 1333. The outer conductor 1333 can be formed of a continuous structure or separate structures for the transmitting portion 1331 and the resonating portion 1332. If separate structures are implemented, the structures can be configured to be connected. The outer conductor 1333 of the transmitting portion 1331 can include a dielectric material 1335 disposed therein. The outer conductor 1333 of the resonating portion 1332 can form a cavity 1336. A length 1344 of the cavity 1336 can define a sensing depth of the sensor 1330. An absorptive material 1337 (also referred to as the electrically absorptive material 1337) can be disposed at an interface between the dielectric material 1335 of the transmitting portion 1331 and the cavity 1336 of the resonating portion 1332.

The sensor 1330 can be connected to control circuitry at a first end 1342 of the sensor 1330 (e.g., an interface end of the sensor 1330). The sensor 1330 can be placed in proximity to or contact with a sample at a second end 1359 of the sensor 1330. In this example, the resonating portion 1332 of the sensor 1330 includes a substantially circular-shaped profile (e.g., a transverse cross-section of the sensor 1330 has a substantially circular shape, providing a cylindrical resonator cavity).

In some embodiments, the sensor 1330 can be designed for various contexts. That is, one or more dimensions of the sensor 1330 can be designed for any number of applications. A dimension of the sensor 1330 can include: a length 1338 of the transmitting portion 1331 (which can include or exclude the absorptive material 1337), a length 1339 of the resonating portion 1332 (which can include or exclude the absorptive material 1337), a diameter 1340 of an inner surface of the outer conductor 1333, the length 1344 of the cavity 1336, a length of the sensor 1330 (which includes the length 1338 and the length 1339), a thickness of the outer conductor 1333 (e.g., a radial thickness), etc. Any dimension can be tuned to achieve a desired performance metric.

FIG. 13B shows an example of the sensor 1330 immersed in the sample 1346. Here, the resonating portion 1332 of the sensor 1330 is fully immersed into the sample 1346. The sample 1346 can include a liquid, a semi-liquid, a solid substance, a gas, a vacuum space, etc. As illustrated, the sample 1346 is located within the resonator cavity 1336. However, in other examples the resonating portion 1332 can be partially immersed into the sample 1346, the sensor 1330 can be immersed into the sample 1346 so that the sample 1346 is above the resonating portion 1332 (e.g., surrounding at least a portion of the transmitting portion 1331), the sensor 1330 can be placed in proximity to the sample 1346, and so on.

Figure 14A:
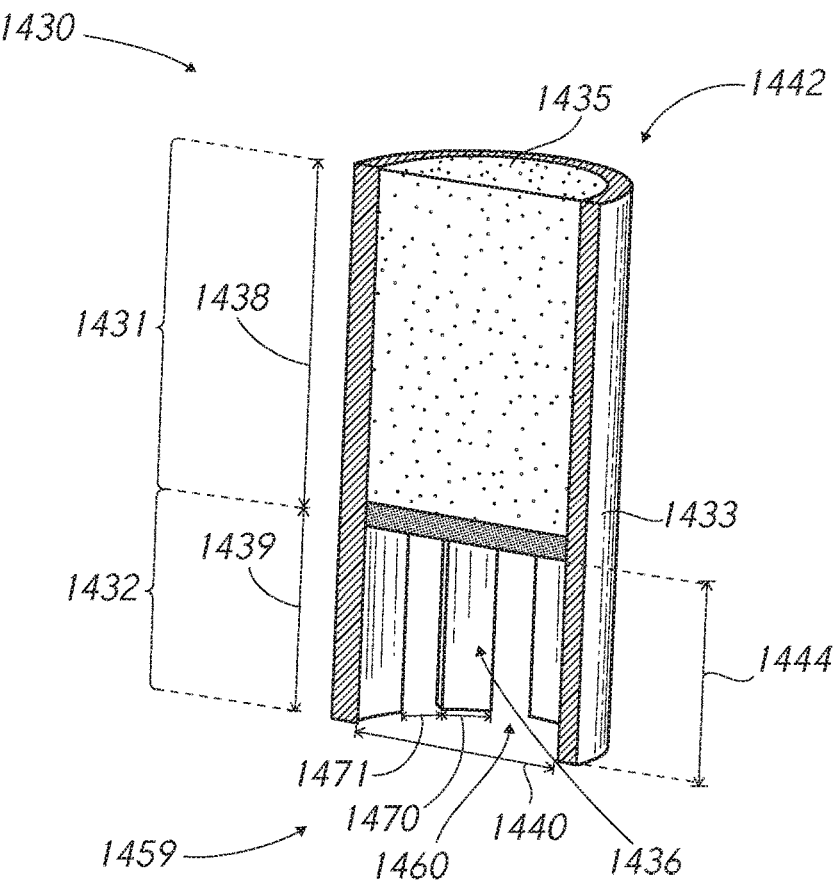
FIG. 14A illustrates a perspective cross-sectional view of an example sensor that has a substantially cylindrical shape and slots, and no inner conductor.
Figure 14B:
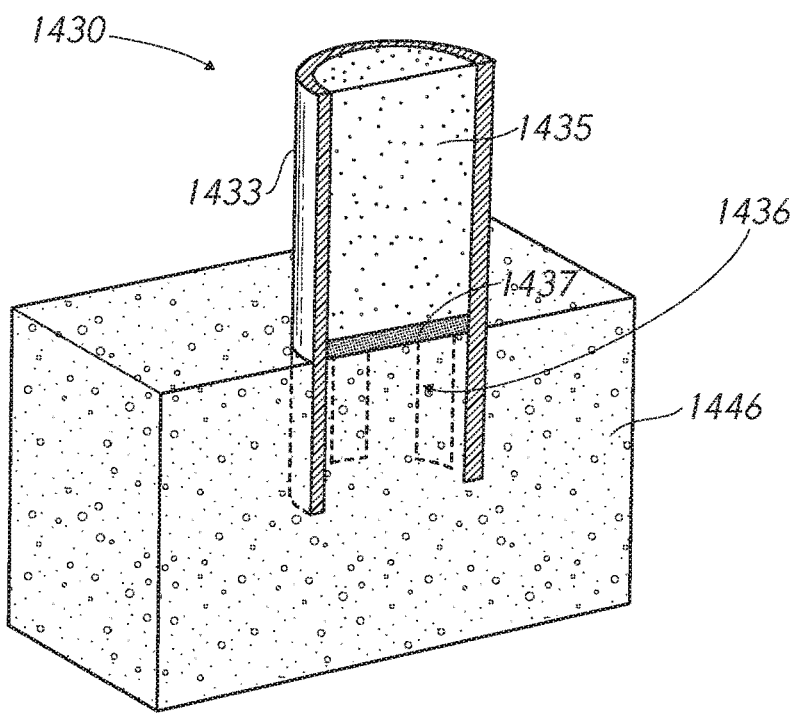
FIG. 14B illustrates a perspective cross-sectional view of the sensor shown in FIG. 14A, wherein a resonating portion thereof is disposed at least partially within sample media.

FIGS. 14A-14B illustrate an example sensor 1430 that has a substantially cylindrical shape and slots. FIGS. 14A-14B show cross-sectional views of the sensor 1430. In this example, the sensor 1430 is implemented without an inner conductor. FIG. 14B shows a perspective view of the sensor 1430 shown in FIG. 14A, wherein a resonating portion 1432 thereof is disposed at least partially within a sample 1446, as shown. The sensor 1430 represents an example embodiment of a sensor device/system (or component/portion thereof) that can be implemented in the various example devices and systems disclosed herein.

The sensor 1430 includes a transmitting portion 1431 and the resonating portion 1432. The transmitting portion 1431 and/or the resonating portion 1432 can include an outer conductor 1433. The outer conductor 1433 can be formed of a continuous structure or separate structures for the transmitting portion 1431 and the resonating portion 1432. If separate structures are implemented, the structures can be configured to be connected. The outer conductor 1433 of the transmitting portion 1431 can include a dielectric material 1435 disposed therein. The outer conductor 1433 of the resonating portion 1432 can form a cavity 1436. A length 1444 of the cavity 1436 can define a sensing depth of the sensor 1430. An absorptive material 1437 (also referred to as the electrically absorptive material 1437) can be disposed at an interface between the dielectric material 1435 of the transmitting portion 1431 and the cavity 1436 of the resonating portion 1432.

The sensor 1430 can be connected to control circuitry at a first end 1442 of the sensor 1430 (e.g., an interface end of the sensor 1430). The sensor 1430 can be placed in proximity to or contact with a sample at a second end 1459 of the sensor 1430. In this example, the resonating portion 1432 of the sensor 1430 includes a substantially circular-shaped profile (e.g., forming a cylindrical resonator cavity).

In some embodiments, the sensor 1430 can include slots 1460 formed in the outer conductor 1433 of the resonating portion 1433. This can allow flow of a sample into or out of the cavity 1436 of the resonating portion 1432. This may ultimately lead to a more accurate measurement of a constituent in a sample. In some embodiments, the slots 1460 can allow a larger amount of flow into the cavity 1436 than a sensor that does not include such slots. The slots 1460 can generally include empty space. However, in some examples a material, such as a non-conducting material, can be disposed within the slots 1460. Each of the slots 1460 can extend from the second end 1459 of the sensor 1432 to the absorptive material 1437. As such, each of the slots 1460 can have a length that corresponds to the length 1444 of the cavity 1436, or a different length in some embodiments. Each of the slots 1460 can also have an arc width 1471. An arc distance 1470 between adjacent slots 1460 around a circumference of the outer conductor 1433 is also shown.

In some embodiments, the sensor 1430 can be designed for various contexts. That is, one or more dimensions of the sensor 1430 can be designed for any number of applications. A dimension of the sensor 1430 can include: a length 1438 of the transmitting portion 1431 (which can include or exclude the absorptive material 1437), a length 1439 of the resonating portion 1432 (which can include or exclude the absorptive material 1437), a diameter 1440 of an inner surface of the outer conductor 1433, the length 1444 of the cavity 1436, a length of the sensor 1430 (which includes the length 1438 and the length 1439), a thickness of the outer conductor 1433 (e.g., a radial thickness), the arc width 1471, the arc distance 1470, etc. Any dimension can be tuned to achieve a desired performance metric.

FIG. 14B shows an example of the sensor 1430 immersed in a sample 1446. Here, the resonating portion 1432 of the sensor 1430 is fully immersed into the sample 1446. The sample 1446 can include a liquid, a semi-liquid, a solid substance, a gas, a vacuum space, etc. As illustrated, the sample 1446 is located within the resonator cavity 1436. However, in other examples the resonating portion 1432 can be partially immersed into the sample 1446, the sensor 1430 can be immersed into the sample 1446 so that the sample 1446 is above the resonating portion 1432 (e.g., surrounding at least a portion of the transmitting portion 1431), the sensor 1430 can be placed in proximity to the sample 1446, and so on.

Although sensors of various forms are illustrated in the figures, a sensor can include other shapes, sizes, or forms, such as an oval-shaped profile, a rectangular-shaped profile with rounded corners, etc.

Figures 1, 15:
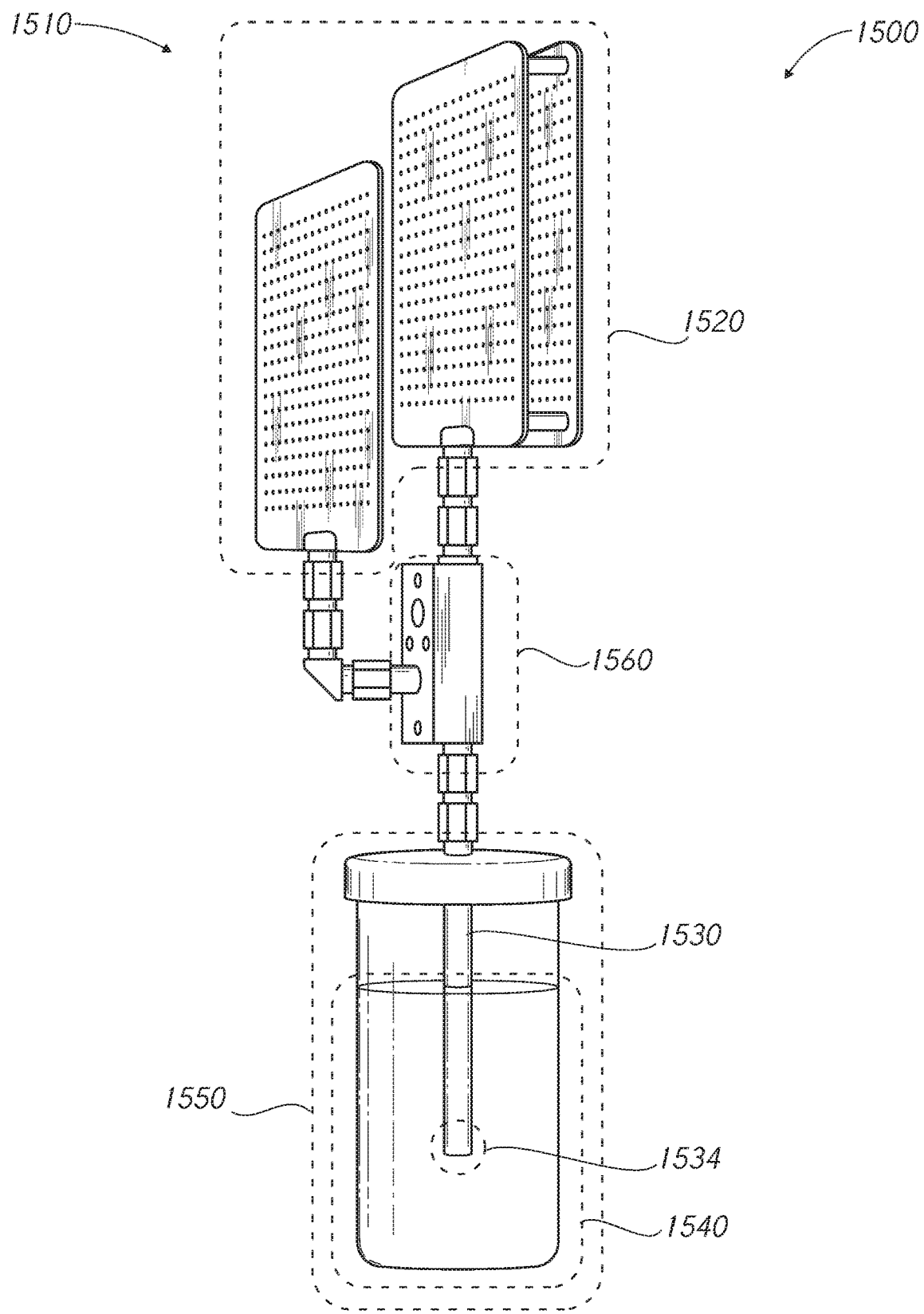
Figures 2, 15:
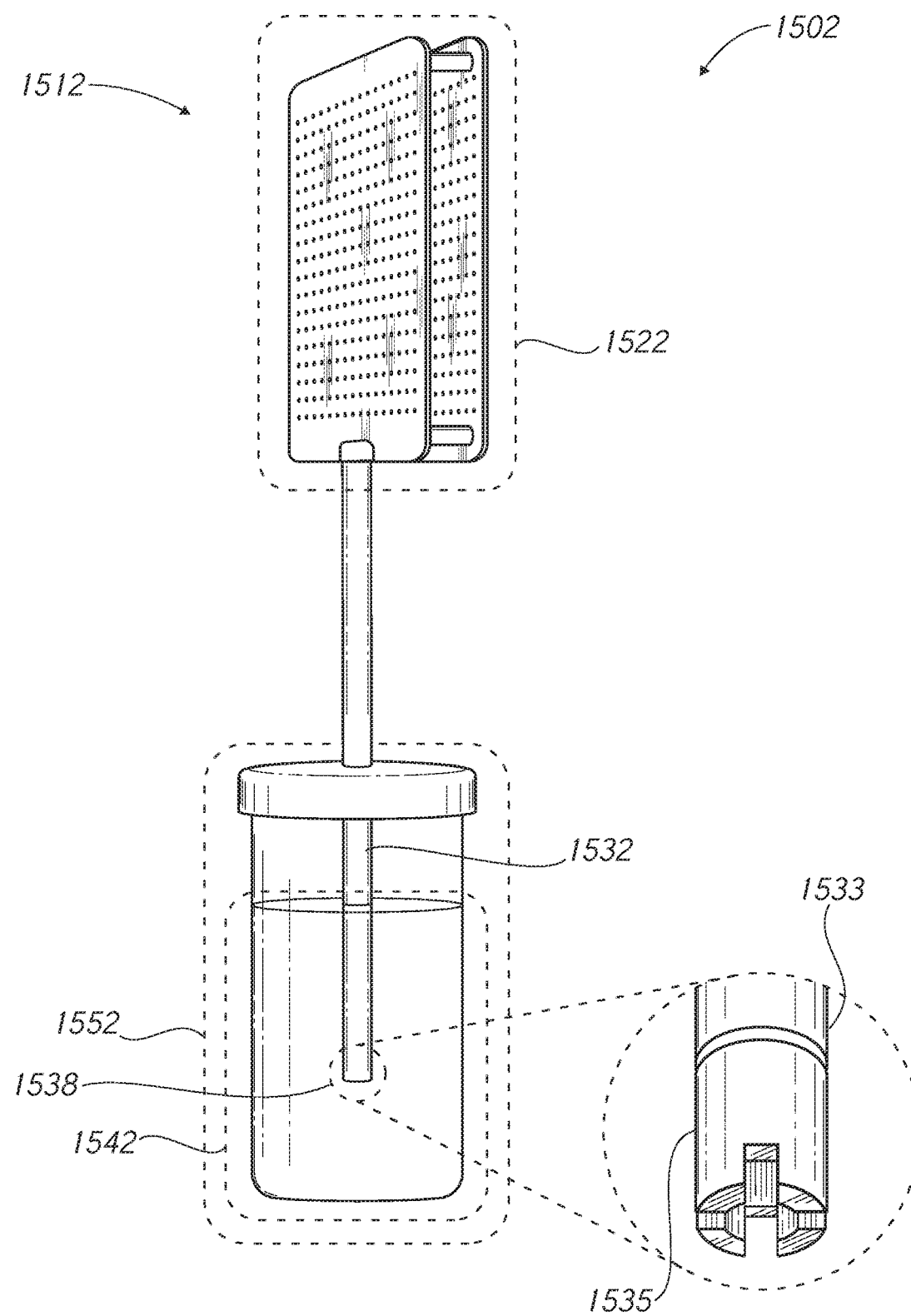

FIG. 15-1 illustrates an example system 1500 with a sensing system 1510 implemented at least in part with a circuit board(s). Although a number of circuit boards are illustrated in this example, any number of circuit boards can be implemented.

In this illustration, the sensing system 1510 includes control circuitry 1520 and a sensor 1530 electrically coupled to the control circuitry 1520 via the one or more interface components 1560. As illustrated, the control circuitry 1520 can be implemented at least in part by one or more circuit boards. However, in other examples the control circuitry 1520 can be implemented in other manners, such as with a computing device or other circuitry, as in various embodiments discussed herein. The one or more interface components 1560 can include connectors, splitters, etc. to facilitate transmission and/or reception of signals via the sensor 1530. For example, the one or more interface components 1560 can allow separate transmission and reception circuit boards to connect to the sensor 1530.

In this illustration, the sensing system 1510 is disposed (or attached) to a container 1550 that includes a sample 1540. Here, the container 1550 is a bioreactor that is used to grow cells, and the sample 1540 is a solution that includes at least water and glucose. The sensor 1530 of the sensing system 1510 is at least partially immersed in the sample to detect a concentration of glucose in the sample 1540. As illustrated, a resonating portion 1534 of the sensor 1530 is immersed in the sample 1540. In other examples the resonating portion 1534 can be partially immersed in the sample 1540 or placed within a distance to the sample 1540.

FIG. 15-2 illustrates another example system 1502 with a sensing system 1512 implemented at least in part with a circuit board(s). Although a number of circuit boards are illustrated in this example, any number of circuit boards can be implemented.

In this illustration, the sensing system 1512 includes control circuitry 1522 and a sensor 1532 electrically coupled to the control circuitry 1522. As illustrated, the control circuitry 1522 can be implemented at least in part by one or more circuit boards. However, in other examples the control circuitry 1522 can be implemented in other manners, such as with a computing device or other circuitry, as in various embodiments discussed herein.

In this illustration, the sensing system 1512 is disposed (or attached) to a container 1552 that includes a sample 1542. Here, the container 1552 is a bioreactor that is used to grow cells, and the sample 1542 is a solution that includes at least water and glucose. In this illustration, the sensor 1532 of the sensing system 1512 is at least partially immersed in the sample to detect a concentration of glucose in the sample 1542. For example, a resonating portion 1535 and/or a transmitting portion 1533 of the sensor 1532 can be immersed in the sample 1542. In other examples the resonating portion 1535 can be partially immersed in the sample 1542 or placed within a distance to the sample 1542.

An end portion 1538 of the sensor 1532 is illustrated in further detail to the right of the container 1552 in FIG. 15-2. In some embodiments, the resonating portion 1535 can be removably attached to the transmitting portion 1533 with, for example, threads, an adhesive, or another attachment mechanism. In other embodiments, the resonating portion 1535 and a first portion of the transmitting portion 1533 can form a single piece that is removably attached to a second portion of the transmitting portion 1533. Although the resonating portion 1535 is illustrated without an inner conductor, in many embodiments the resonating portion 1535 includes an inner conductor.

FIGS. 16A-D illustrate an example sensor 1630 with a membrane structure 1650 that includes a semi-permeable membrane 1654. The sensor 1630 represents an example embodiment of a sensor device/system (or component/portion thereof) that can be implemented in the various example devices and systems disclosed herein. In some embodiments, the sensor 1630 and/or the membrane structure 1650 can be implemented within a bioreactor or another device.

The membrane structure 1650 (sometimes referred to as the "container structure 1650") can include a cylinder-shaped slotted supporting fixture 1655, cylinder-shaped extruded guide rings 1657, a cylinder-shaped semi-permeable membrane 1654 disposed over or in openings of the cylinder-shaped slotted supporting fixture 1655 (and/or around other portions of the cylinder-shaped slotted supporting fixture 1655), elastic securing rings 1653, a cap 1651 (which is threaded in this example), and/or a cylinder-shaped shrinkable encasing material 1656. In some embodiments, the cylinder-shaped slotted supporting fixture 1655 of the membrane structure 1650 can form a cavity 1658 to receive a sample. The cavity 1658 can be at least partially enclosed by the semi-permeable membrane 1654. Although many components of the membrane structure 1650 are discussed as being cylinder-shaped, the components can include other forms. In some embodiments, the components can be designed to fit the form of a sensor, which can take various forms as discussed herein.

The membrane structure 1650 can removably receive at least a portion of the sensor 1630. The sensor 1630 can be slide into an opening in the membrane structure 1650 to enable a resonating portion 1634 and/or a transmitting portion 1632 of the sensor 1630 to be located within the membrane structure 1650. In some embodiments, the resonating portion 1634 can be slid into the cavity 1658 of the membrane structure 1650. This can allow the resonating portion 1634 to come into contact to a sample within the cavity 1658.

The membrane structure 1650 can be used to filter particles into or out of the cavity 1658 of the membrane structure 1650. For example, the membrane structure 1650 can permit particles that are smaller than a threshold size (e.g., a solution of water and glucose) to pass through into the cavity 1658, and block particles that are larger than the threshold size (e.g., cells growing in the solution) from passing through into the cavity 1658. The semi-permeable membrane 1654 can cover openings and/or structure of the cylinder-shaped slotted supporting fixture 1655 to enclose the cavity 1658. The semi-permeable membrane 1654 can act as a filter to permit or block particles from flowing into or out of the cavity 1658. As such, the membrane structure 1650 can enclose the resonating portion 1634 of the sensor 1630 using the semi-permeable membrane 1654.

As shown, FIG. 16A illustrates a cross-sectional view of the membrane structure 1650 and the sensor 1630, FIG. 16B illustrates the membrane structure 1650 (and the sensor 1630) with the cylinder-shaped shrinkable encasing material 1656, FIG. 16C illustrates the membrane structure 1650 (and the sensor 1630) with the cylinder-shaped shrinkable encasing material 1656 removed, and FIG. 16D illustrates the membrane structure 1650 (and the sensor 1630) with the cylinder-shaped shrinkable encasing material 1656, the cap 1651, and the elastic securing rings 1653 removed.

Figure 17:
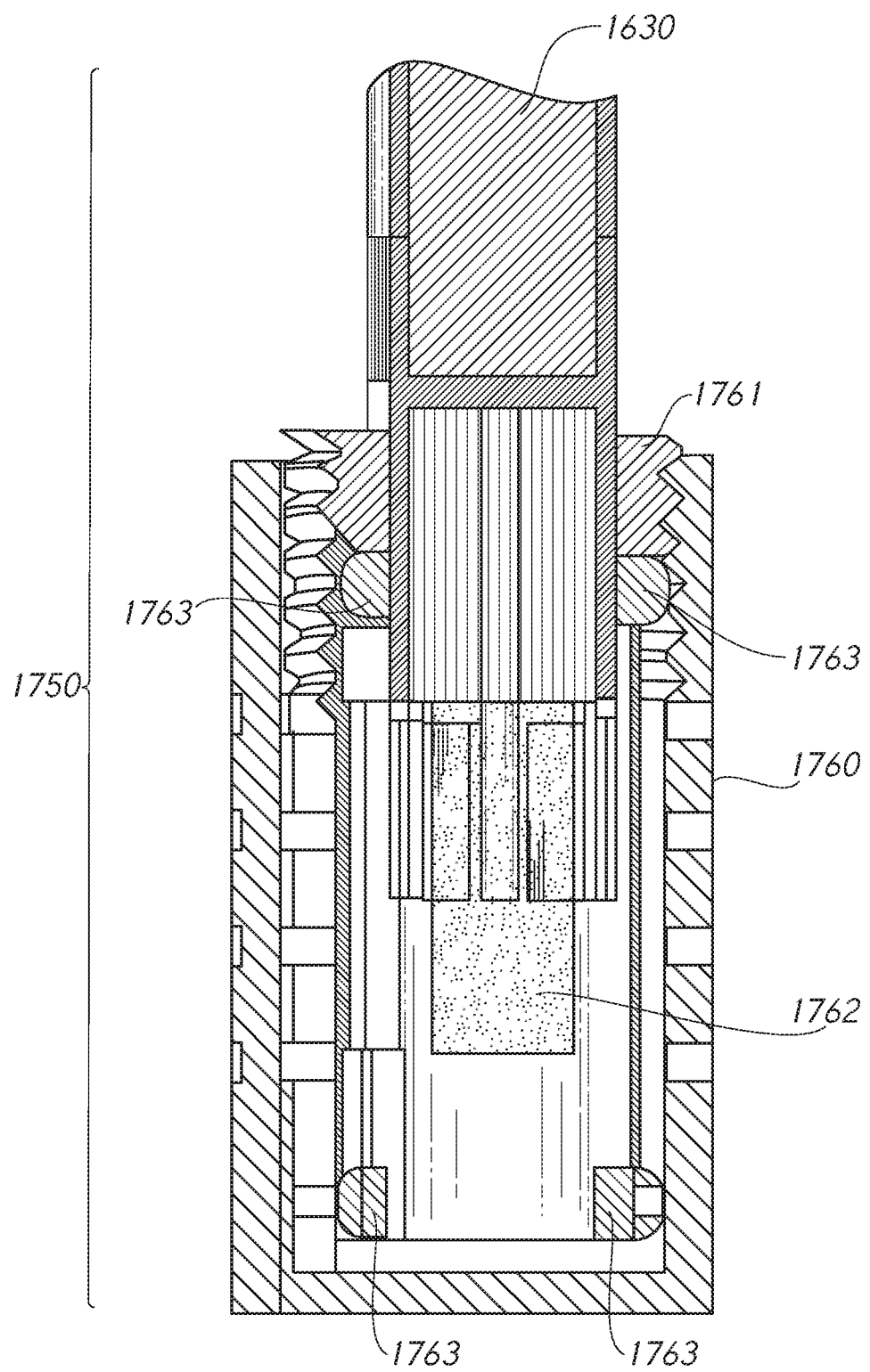
FIG. 17 illustrates another example membrane structure that includes a semi-permeable membrane.

FIG. 17 illustrates another example membrane structure 1750 that includes a semi-permeable membrane 1762. The membrane structure 1750 is similar to the membrane structure 1650 of FIGS. 16A-16D, however, the cap 1651 and the cylinder-shaped slotted supporting fixture 1655 have been replaced with different structure. In particular, for the membrane structure 1750, the cap 1651 has been replaced with a slotted enclosure 1760 (to receive the sensor 1630), and the cylinder-shaped slotted supporting fixture 1655 has been replaced with a slotted supporting fixture 1761 (to support the semi-permeable membrane 1762).

The slotted enclosure 1760 can be removably attached to the slotted supporting fixture 1761. In this example, the slotted enclosure 1760 and the slotted supporting fixture 1761 are attached using threads. However, in other examples other attachment mechanisms can be used, such as clips, an adhesive, etc. The slotted enclosure 1760 can provide additional structural protection for the semi-permeable membrane 1762. The membrane structure 1750 can also include elastic securing rings 1763 disposed in between the slotted enclosure 1760 and the slotted supporting fixture 1761.

Figure 18:
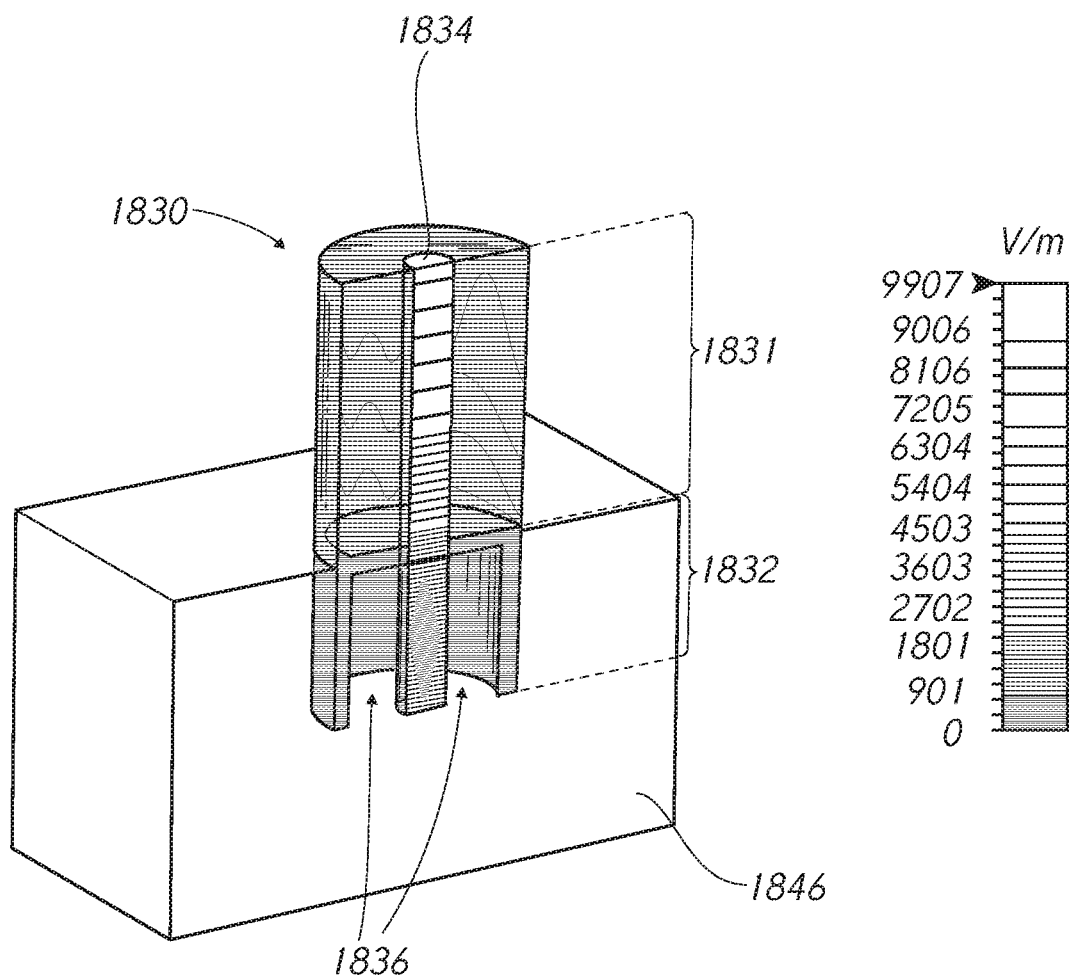
FIG. 18 illustrates an example electromagnetic simulation overlaid on a sensor.

FIG. 18 illustrates an example electromagnetic simulation overlaid on a sensor 1830. Here, the electromagnetic simulation illustrates a strength of an electric field in volts per meter as the sensor 1830 detects a constituent in a sample 1846 (e.g., as a signal is transmitted and/or received by the sensor 1830). The sensor 1830 can include any of the example sensors discussed herein.

As illustrated, the sensor 1830 includes a transmitting portion 1831 and a resonating portion 1832. The sensor 1830 also includes an inner conductor 1834 disposed through a center of the sensor 1830. The resonating portion 1832 is immersed in the sample 1846 such that the sample 1846 fills a cavity 1836 of the resonating portion 1832.

Figure 19:
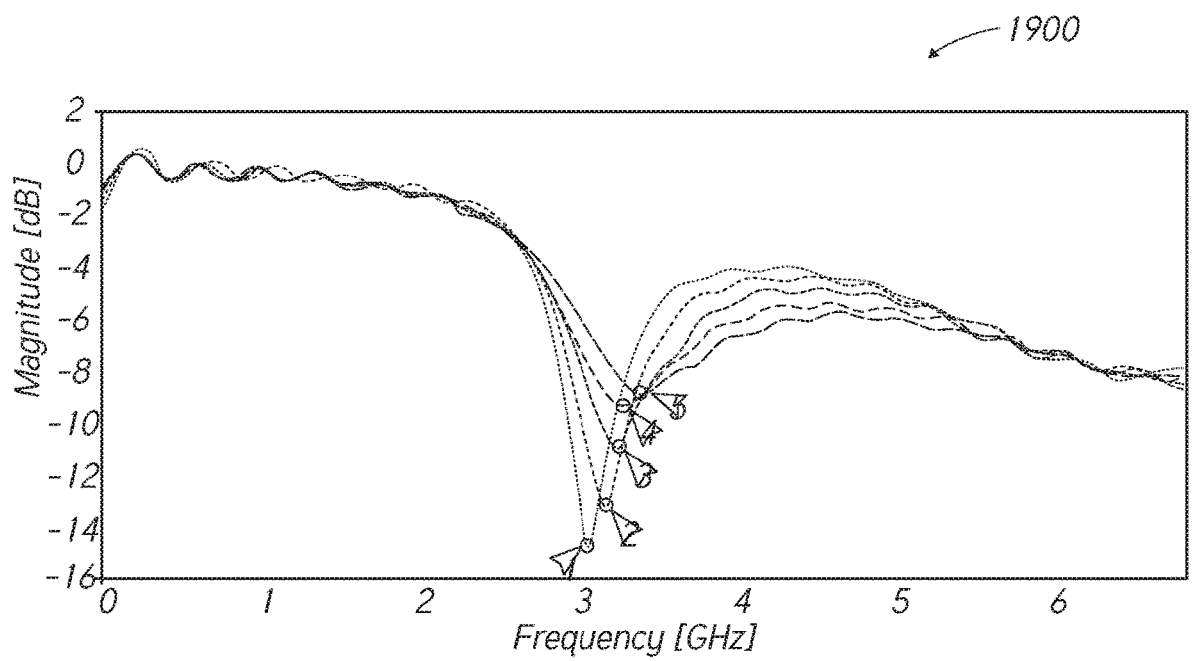
FIG. 19 illustrates an example graph of data of signals detected by any of the sensors discussed herein.

FIG. 19 illustrates an example graph 1900 of data of signals that can be detected by any of the sensors discussed herein. Here, the graph 1900 shows a magnitude of reflected signals in decibels (dB) with respect to frequency (GHz) of the reflected signals.

To obtain the data for the graph 1900, a sensing system can sweep across a frequency range from 0 GHz to about 7 GHz and detect reflected signals. The graph 1900 shows the magnitude of reflected signals for such frequency range. A magnitude of a reflected signal can be associated with an amplitude of a reflected signal. In some embodiments, the graph 1900 represents data that is obtained over time as a concentration of glucose or water changes or that is obtained from solutions of different concentrations of glucose or water.

As illustrated, the graph 1900 shows resonant frequencies for different concentrations of glucose or water in a solution. The marked points in the graph 1900 (e.g., lowest magnitude points) indicate the resonant frequencies. A resonant frequency can be correlated to a concentration of glucose or water in the solution. As shown, a resonant frequency of the solution having a concentration of water is labeled at a point "1" (i.e., 3.0532 GHz), a resonant frequency of a solution having a first concentration of glucose is labeled at a point "2" (i.e., 3.18424 GHz), a resonant frequency of a solution having a second concentration of glucose is labeled at a point "3" (i.e., 3.2648 GHz), and so on.

Figure 20:
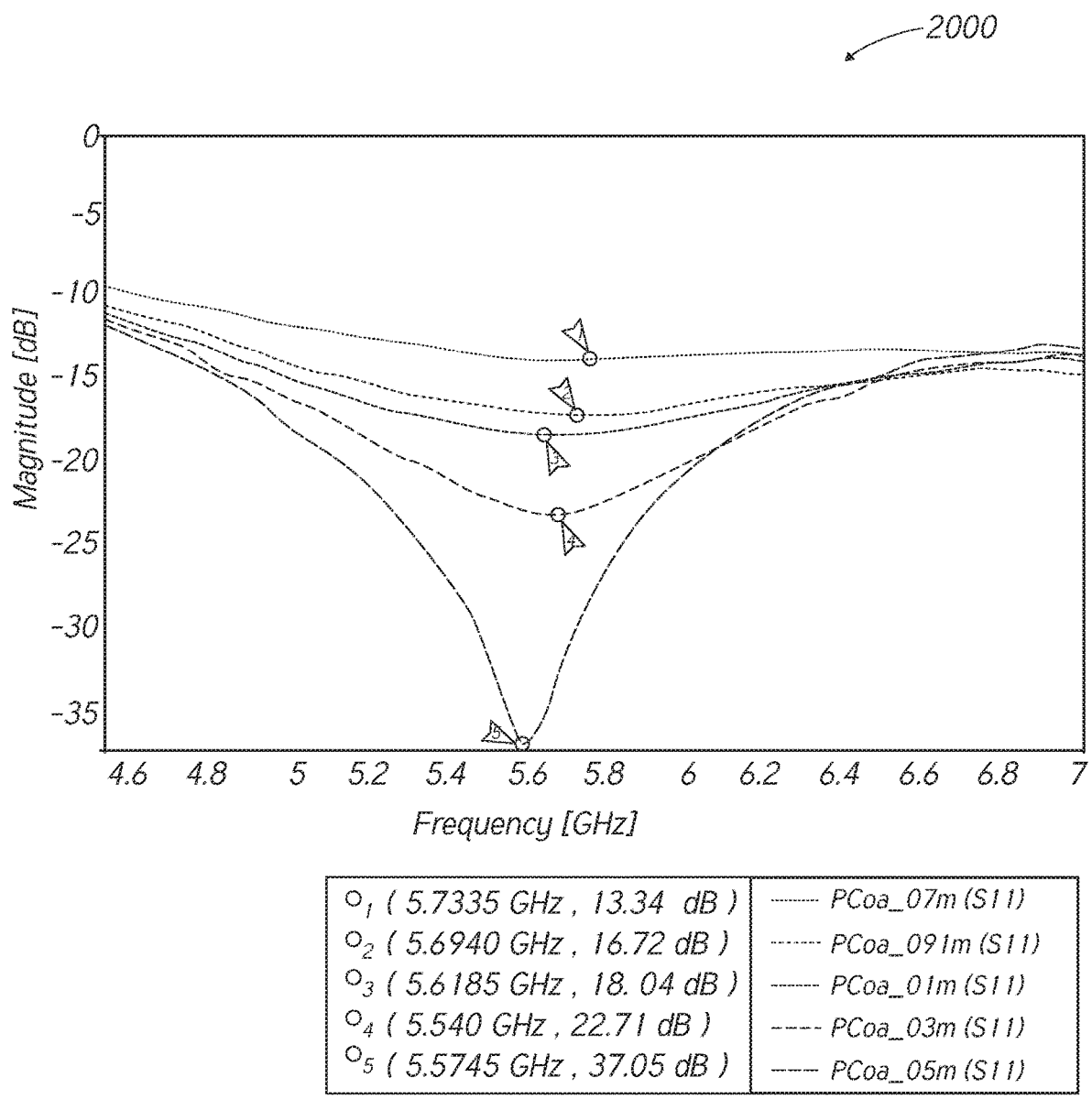
FIG. 20 illustrates an example graph of data of signals detected by any of the sensors discussed herein.

FIG. 20 illustrates an example graph 2000 of data of signals that can be detected by any of the sensors discussed herein. Here, the graph 2000 shows a magnitude of reflected signals in decibels (dB) with respect to frequency (GHz) of the reflected signals.

To obtain the data for the graph 2000, a sensing system can sweep across a frequency range from about 4.5 GHz to 7 GHz and detect reflected signals. The graph 2000 shows the magnitude of reflected signals for such frequency range. A magnitude of a reflected signal can be associated with an amplitude of a reflected signal. In some embodiments, the graph 2000 represents data that is obtained over time as a concentration of a constituent changes or that is obtained from solutions of different concentrations of a constituent.

As illustrated, the graph 2000 shows resonant frequencies for different concentrations of a constituent in a solution. The marked points in the graph 2000 (e.g., lowest magnitude points) indicate the resonant frequencies. A resonant frequency can be correlated to a concentration of a constituent in the solution. As shown, a resonant frequency of the solution having a first concentration of a constituent is labeled at a point "1" (i.e., 5.7335 GHz), a resonant frequency of the solution having a second concentration of a constituent is labeled at a point "2" (i.e., 5.6940 GHz), a resonant frequency of the solution having a third concentration of a constituent is labeled at a point "3" (i.e., 5.6185 GHz), and so on.

FIGS. 21-32 illustrate various aspects of example radiating devices that are configured to detect properties of a sample. FIGS. 21-30 show radiating devices implemented as stripline transmission lines. However, other types of transmission lines can be used, as discussed below. Although FIGS. 21-32 illustrate various aspects of radiating devices, in some embodiments a radiating device can include aspects of other devices discussed herein. Further, the other devices discussed herein can include aspects of a radiating device in some examples.

In some embodiments, a radiating device can comprise a physically non-invasive sensing device that can detect properties of external samples placed on or near a radiating aperture of the device. The device can detect external samples located within the radiating field of a single aperture or multiple radiating apertures. The samples can be in contact with the radiating aperture or they can be physically separated from the aperture. In addition, the device can detect samples that are completely exposed to the radiating field, or that are partially enclosed within a separating medium, or that are completely enclosed within a separating medium. The device can detect the entirety or a portion of the external sample. The device can be placed in any practical location as the device is not limited to a through measurement configuration. Moreover, the device can detect biological, organic chemical, and/or inorganic chemical compositions in solid, liquid, and/or gas forms.

In some embodiments, the radiating device can include a radiating aperture or multiple radiating apertures that use electromagnetic energy to detect an external sample. Several peripheral elements can be added to the radiating aperture element for convenience in interconnecting the radiating aperture to electromagnetic signal sources and/or recording elements. These peripheral elements can include an input interface, an input interface transition section, an input transmission line, an input transmission line coupling section, an output transmission line coupling section, an output transmission line, an output interface transition section, an output interface, and/or layers and features to make and use the device.

In some embodiments, the radiating aperture is formed in at least one layer of metallized dielectrics. The peripheral elements can also be formed in at least one layer of metallized dielectrics. These peripheral elements can include an input interface, input interface transition section, input transmission line, input transmission line coupling section, output transmission line coupling section, output transmission line, output interface transition section, and/or output interface. The device can be formed with all or none of the peripheral elements.

In some embodiments, the device is formed in multiple layers of metallized dielectrics, where the layers form a stripline structure, and the transmission line sections are in the form of a stripline. The stripline structure can be formed using a combination of two metallized dielectric layers. The first metallized dielectric layer can include a combination of a dielectric material of uniform predetermined thickness and an unpatterned metal layer located under and connected to the dielectric material, and the unpatterned metal layer can form a ground plane. The second metallized dielectric layer can include a combination of a dielectric material of uniform predetermined thickness, a first patterned metal layer located under and connected to the same dielectric layer, and a second patterned metal layer located on the surface of and connected to this dielectric layer. The first patterned metal layer can be located on the surface of and connected to the dielectric material of the first metallized dielectric layer, and the first patterned metal layer can form a center conductor of the stripline transmission line. Also, the second patterned metal layer can include a radiating aperture of a predetermined length and width, and the radiating aperture can be formed perpendicular to the center conductor of the stripline transmission line. The radiating aperture can be straight, curved, or shaped to accommodate physical or electrical constraints of the device. In addition, the stripline-based sensing device can further comprise multiple ground vias, an input signal via, and/or an output signal via.

In some embodiments, the device can be implemented with a stripline transmission line. However, in other embodiments the device can take different forms, such as a micro square-ax, microstrip, co-planar waveguide, waveguide, suspended stripline, coaxial line, or a combination of these transmission lines.

In some embodiments, a method of sensing an external sample includes providing an input electromagnetic signal to a radiating aperture, where the electromagnetic signal is modified by the external sample. The modified electromagnetic signal can be collected from the radiating aperture. In such a manner, a radiating field from the radiating aperture can non-destructively and non-invasively sense at least a portion of an external sample located within the range of the radiating field, wherein the external sample can be exposed directly to the radiating field, or the external sample can be completely enclosed within a separating medium, or the external example can be partially enclosed with the separating medium.

In some embodiments, a radiating device can be a non-invasive device that senses an external sample and collects characterization information about the sample. The information sensed by this device can be measured and quantified by an external characterization tool and/or algorithm so that detailed properties of an external sample can be known. In some embodiments, the device includes a radiating aperture. Additional peripheral interconnecting elements can also be used depending on how the radiating aperture is placed within a higher assembly. Peripheral elements can include an input interface, an input interface transition section, an input transmission line, an input transmission line coupling section, a radiating aperture, an output transmission line coupling section, an output transmission line, an output interface transition section, an output interface, and/or layers and features to make and use the device.

Figure 21:
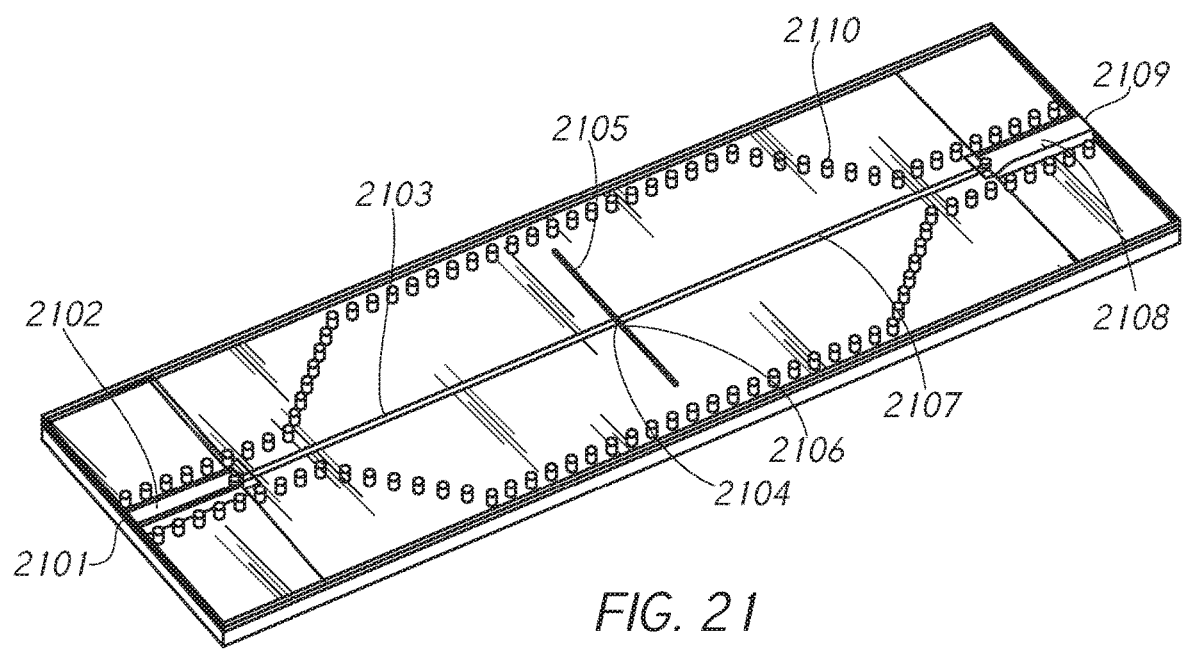
FIG. 21 illustrates an example radiating device in accordance with one or more embodiments of the present disclosure.

FIG. 21 illustrates one embodiment of a radiating device, which includes an input interface 2101, an input interface transition section 2102, an input transmission line section 2103, an input transmission line coupling section 2104, a radiating aperture 2105, an output transmission line coupling section 2106, an output transmission line section 2107, an output interface transition section 2108, an output interface 2109, and/or a series of ground vias 2110 placed in locations (which can be predetermined).

Figure 22:
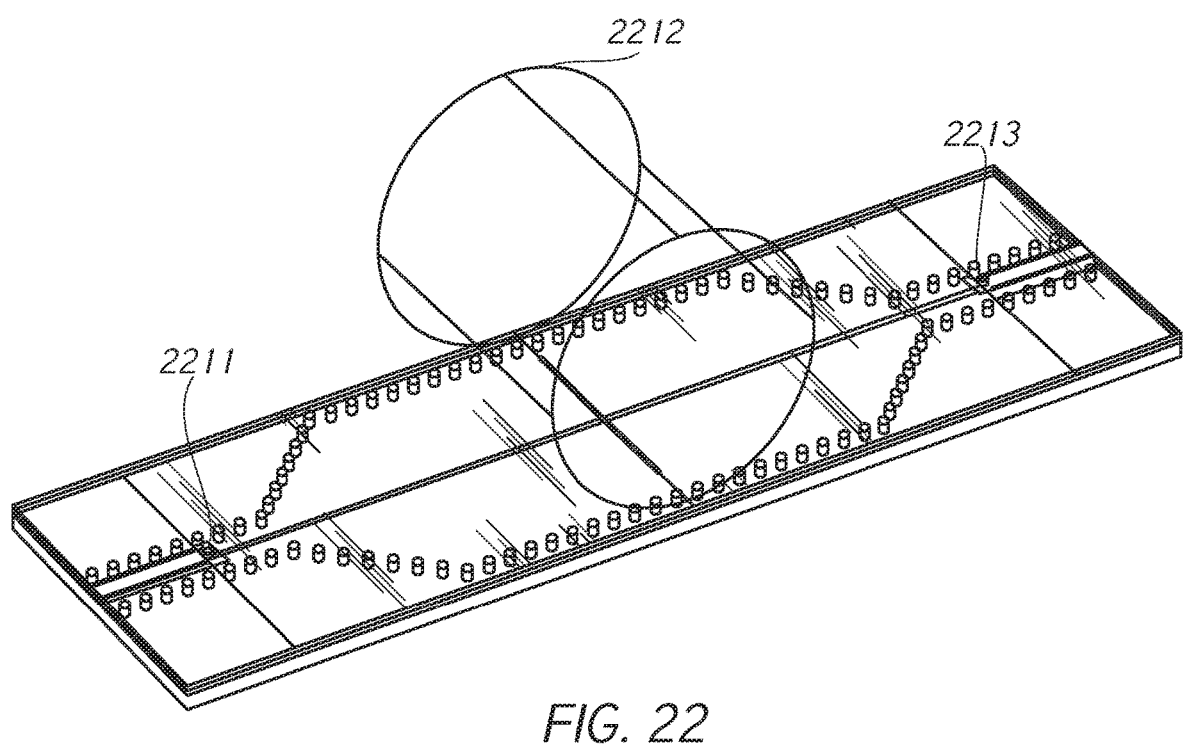
FIG. 22 illustrates example details of the radiating device of FIG. 21.

FIG. 22 shows example details of the radiating device of FIG. 21. FIG. 22 shows an input signal via 2211, an external sample 2212 having a size and shape, and/or an output signal via 2213. The external sample 2212 can be placed on the surface of or within the radiating field of the radiating aperture 2105 so that the device can sense and detect the external sample 2212.

The input interface 2101 can be in communication with the input interface transition section 2102. The input interface transition section 2102 can be in communication with the input transmission line section 2103 through the input signal via 2111. The input transmission line section 2103 can be in communication with the input transmission line coupling section 2104. The input transmission line coupling section 2104 can be in communication with the radiating aperture 2105. The radiating aperture 2105 can be in communication with the output transmission line coupling section 2106. The output transmission line coupling section 2106 can be in communication with the output transmission line section 2107. The output transmission line section 2107 can be in communication with the output interface transition section 2108 through the output signal via 2213. The output transition section 2108 can be in communication with the output interface 2109.

In some embodiments, an electromagnetic signal is applied at the input interface 2101, from which the signal propagates to the input interface transition section 2102 towards the input transmission line section 2103. The signal then propagates from the input interface transition section 2102, through the input signal via 2211, and into the input transmission line section 2103 towards the input transmission line coupling section 2104. The signal continues to propagate into and through the input transmission line coupling section 2104 until the signal travels to the radiating aperture 2105. The signal radiates from the radiating aperture 2105, where the signal interacts with an external sample 2212 through the radiating aperture 2105. The signal continues propagating from the radiating aperture 2105 to the output transmission line coupling section 2106, then to the output transmission line section 2107, then through the output signal via 2213 to the output interface transition section 2108, then to the output interface 2109, and down the line until the signal is collected at the output interface 2109 of the device, where the signal can be measured and recorded.

Figure 23:
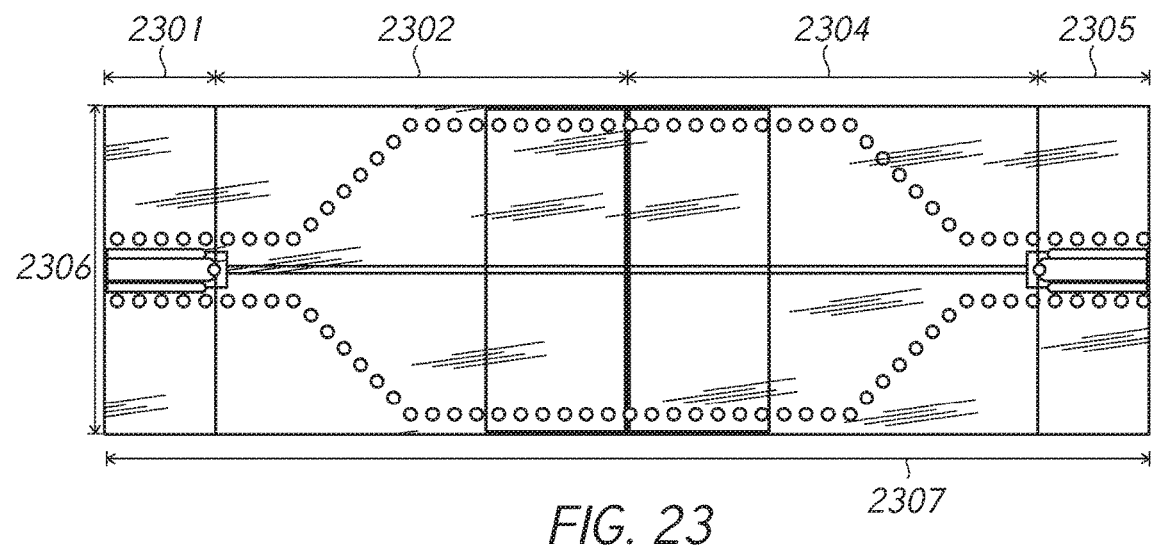
FIG. 23 illustrates an example plan view of the radiating device of FIG. 21 to show example dimensions of the radiating device.
Figure 24:
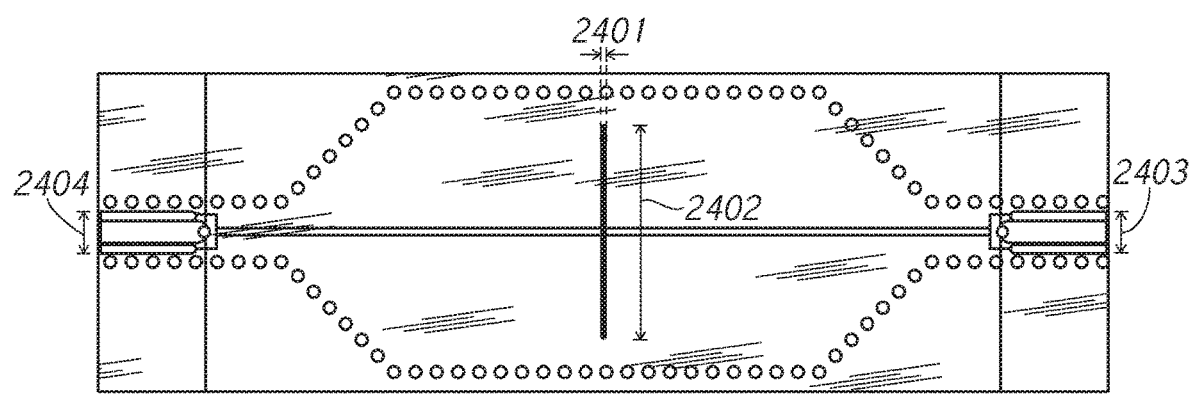
FIG. 24 illustrates an example plan view of the radiating device of FIG. 21 to show additional example dimensions of the radiating device.

In some embodiments, elements of a radiating device can be placed in predetermined locations, as shown in FIGS. 23 and 24. The radiating device of FIGS. 23 and 24 can represent any of the radiating device of FIGS. 21-30.

As shown in FIG. 23, an example radiating device can include various dimensions. For example, the device can include a dimension 2302 representing a length of an input transmission line section, a dimension 2304 representing a length of an output transmission line section, a dimension 2307 representing a length of a sensing device, a dimension 2301 representing a length of an input interface transition section, a dimension 2305 representing a length of an output interface transition section, a dimension 2306 representing a width of a sensing device, etc. In some embodiments, any of such dimensions can be predetermined.

Further, as shown in FIG. 24, the example radiating device can include a dimension 2401 representing a length of a radiating aperture, a dimension 2402 represents a width of the radiating aperture, a dimension 2403 representing a width of an output interface transition section, a dimension 2404 representing a width of an input interface transition section, etc. In some embodiments, any of such dimensions can be predetermined.

In some embodiments, the radiating aperture 2105 is designed to radiate electromagnetic energy into the sample. The magnitude of radiation can be determined by the dimensions of the radiating aperture 2105 and/or the transmission line, as shown in FIG. 24. The aperture radiation can be directly related to a known input signal and/or a measured output signal response. The presence of an external sample 2212 located on or within the radiating field of the radiating aperture 2105 can change the supplied electromagnetic signal. The measured responses of various biological, organic chemical, inorganic chemical, viral, bacterial, etc. samples in solid, liquid, or gas form can show a unique signature for the type and concentration of the external samples. In some embodiments, devices and techniques discussed herein enable the development of commercially viable non-invasive detection, characterization, and/or quantifying instruments.

Figure 25:
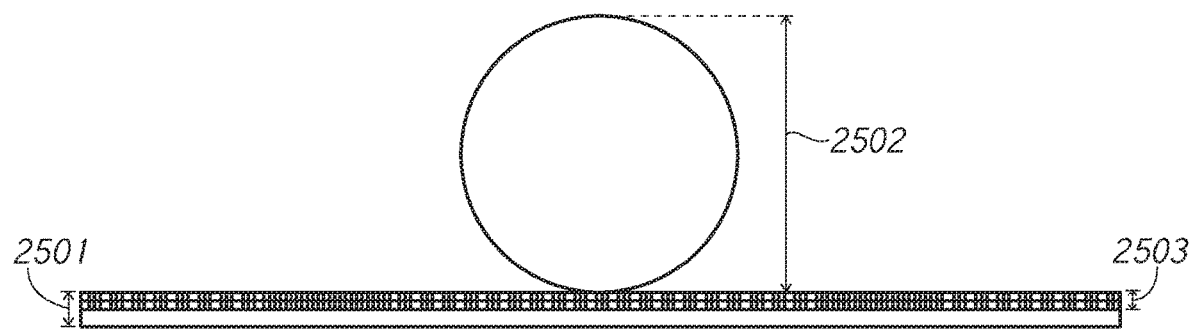
FIG. 25 illustrates a side view of an example radiating device.

FIG. 25 shows a side view of an example radiating device, such as a radiating device of any of FIGS. 21-30, and an external sample of a size and shape. A dimension 2501 can represent a thickness of the device, a dimension 2502 can represent an external sample height of an amount, and a dimension 2503 can represent a thickness of metallized dielectric layers. The thicknesses can be determined so that a transmission line sections function in a manner to transmit a signal to and from a radiating aperture as needed.

Figure 26:
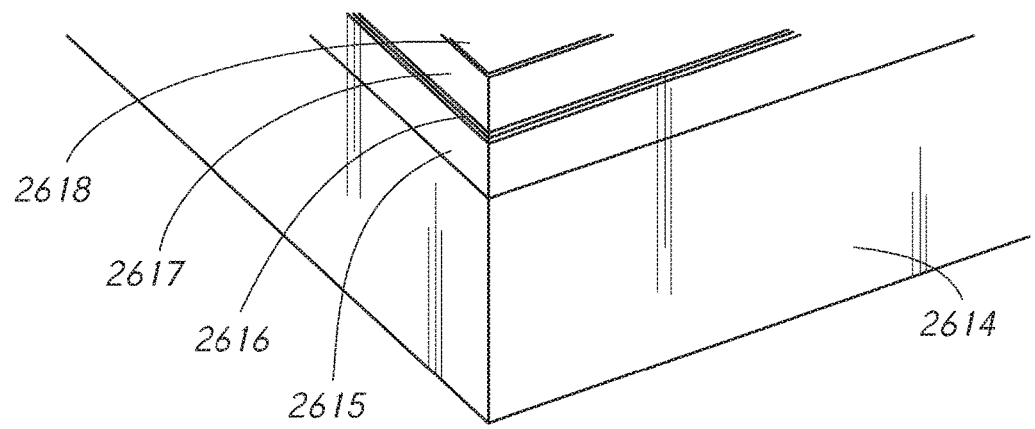
FIG. 26 illustrates a perspective view of metallized dielectric layers of an example radiating device.

FIG. 26 shows a perspective view of metallized dielectric layers of an example radiating device, such as a radiating device of any of FIGS. 21-30. In the example of FIG. 26, the layers form a stripline structure. An unpatterned metal layer 2614 can form a ground plane and/or be connected to a first metallized dielectric layer 2615, which can be of a uniform predetermined thickness. A first patterned metal layer 2616 can be attached to the dielectric surface of the first metallized dielectric layer 2615 and/or the underside dielectric surface of the second metallized dielectric layer 2617. In such a configuration, the first patterned metal layer 2616 forms a center conductor. The second patterned metal layer 2618 can be attached to the top-side surface of the second metallized dielectric layer 2617.

Figure 27:
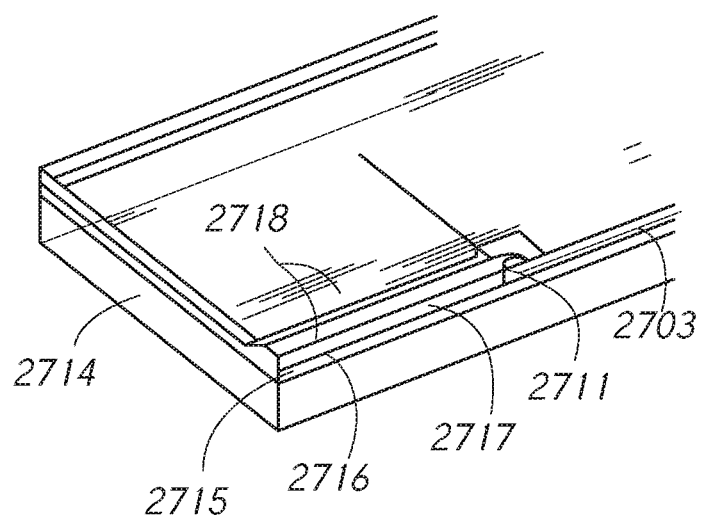
FIG. 27 illustrates a perspective cross-sectional view of a center of an example device input section of an example radiating device.

FIG. 27 shows a perspective cross-sectional view of a center of an example device input section of an example radiating device, such as a radiating device of any of FIGS. 21-30.

Figure 28:
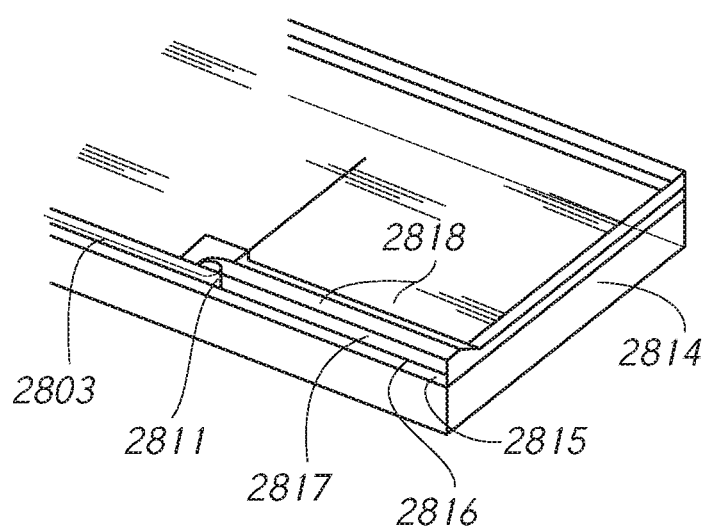
FIG. 28 illustrates a perspective cross-sectional view of a center of a device output section of an example radiating device.

FIG. 28 shows a perspective cross-sectional view of a center of a device output section of an example radiating device, such as a radiating device of any of FIGS. 21-30.

Figure 29:
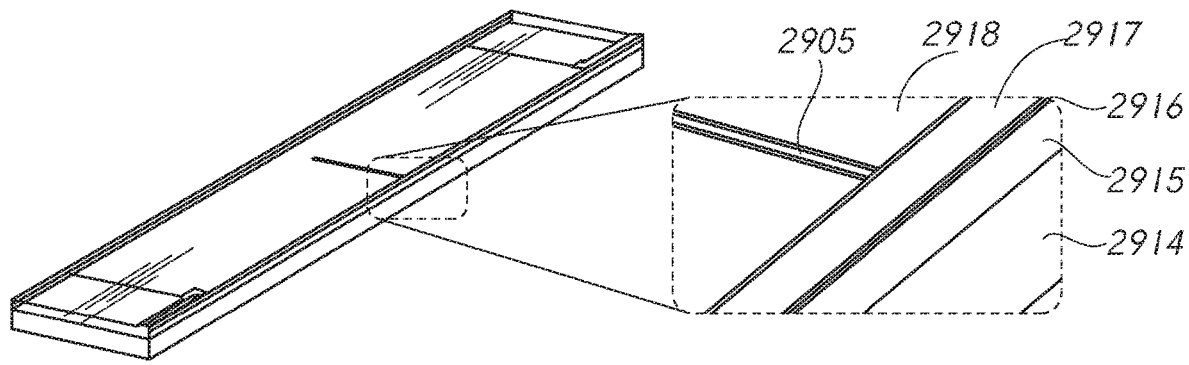
FIG. 29 illustrates a perspective cross-sectional view of a center of a radiating aperture section of an example radiating device.

FIG. 29 shows a perspective cross-sectional view of a center of a radiating aperture section of an example radiating device, such as a radiating device of any of FIGS. 21-30. The second patterned metal layer 2618 is shown on the top-side surfaces of the device illustrations in FIGS. 27-29. The radiating aperture 2205 can be formed by removing a metal section from the second patterned metal layer 2618 in predetermined shape, size, and/or location. The stripline transmission line sections can be formed by patterning a strip of metal within the first patterned metal layer 2616.

Figure 30:
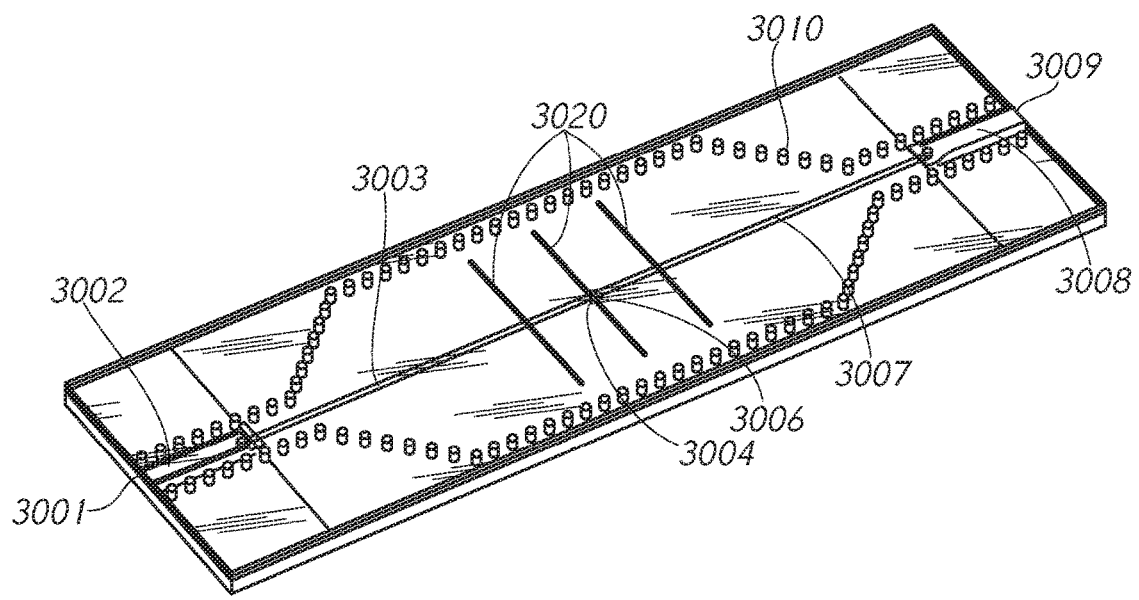
FIG. 30 illustrates another embodiment of a radiating device, where an array of multiple apertures is used.

FIG. 30 shows another embodiment of a radiating device, where an array of multiple apertures 3020 is used instead of a single radiating aperture. In some embodiments, the array of multiple apertures 3020 is connected in the same way and retains the same basic function as a single radiating aperture, such as the single radiating aperture 2105. An example difference in the array of multiple apertures 3020 is the amount and/or location of electromagnetic energy that can be radiated from the device. The size and/or spacing of the array of multiple apertures 3020 can be predetermined based on the design and/or need of the application.

In some embodiments, the radiating device of FIG. 30 can also include an input interface 3001, an input interface transition section 3002, an input transmission line section 3003, an input transmission line coupling section 3004, an output transmission line coupling section 3006, an output transmission line section 3007, an output interface transition section 3008, an output interface 3009, and/or a series of ground vias 3010.

Figure 31:
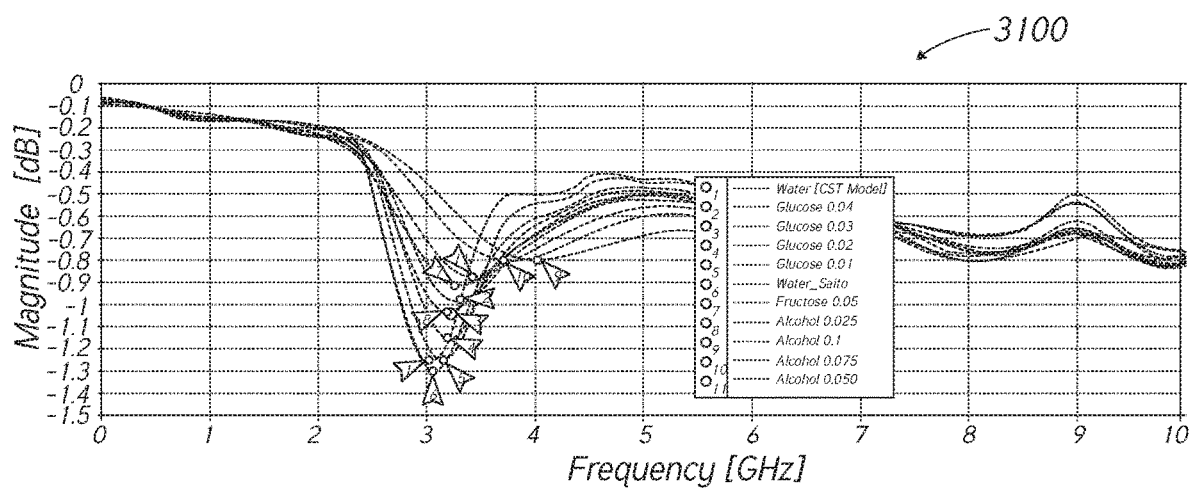
FIG. 31 illustrates a graph of data associated with detecting external samples with an example radiating device.
Figure 32:
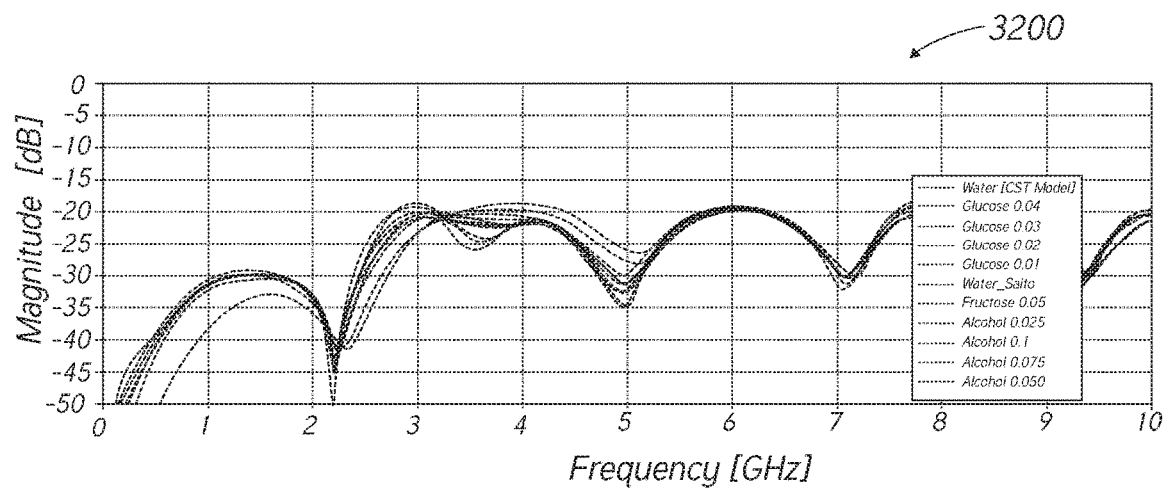
FIG. 32 illustrates another graph of data associated with detecting external samples with an example radiating device.

FIG. 31 shows a graph 3100 of data associated with detecting external samples with an example radiating device. FIG. 32 shows another graph 3200 of data associated with detecting external samples with an example radiating device. In some embodiments, a radiating device can be implemented at least in part as micro square-ax, microstrip, co-planar waveguide, waveguide, suspended stripline, stripline, coaxial line, or a combination of these transmission lines. Example elements of a radiating device are discussed below.

In some embodiments, a transmission line function can be performed by several types of transmission lines, including micro square-ax, microstrip, co-planar waveguide, waveguide, suspended stripline, stripline, coaxial line, or a combination of these transmission lines. Each type of transmission line is a transport medium or channel that supports propagation of electromagnetic signals through the line. Each type of transmission line offers its own advantages, such as compactness, low loss, low fabrication cost, and/or frequency bandwidth capacity. In some embodiments, devices and techniques discussed herein can be realized by any type of transmission line.

In some embodiments, a radiating aperture (also referred to as an aperture) along a transmission line serves as an electromagnetic window, through which electromagnetic energy exits the transmission line and radiates into a sample. The aperture can also be called a radiating aperture. A size of the aperture can determine an amount of radiated energy and/or frequency behavior of the electromagnetic signal that radiate towards the sample. The presence of an aperture can also affect transmission line performance since it uses energy from a transmission line to generate this radiation pattern into the sample. Aperture features can vary in multiple ways depending on the desired location and/or type of radiation pattern required for the detected external sample. Aperture features are described below.

In some embodiments, a shape of an aperture is rectangular. However, the aperture is not restricted to a rectangular shape and can hold the form of any geometric shape that is able to produce a radiation pattern towards the sample. In some embodiments, the aperture shape can be a planar or a 3D radiation element, such as a small post that radiates outside the element.

In some embodiments, an aperture may be a single slot or an array of slots. The aperture(s) can also have multiple two-dimensional and three-dimensional shapes or multiple combinations of two-dimensional and three-dimensional geometric shapes to generate the desired radiation pattern to detect a specific sample type.

In some embodiments, an aperture position(s) can be both symmetric and non-symmetric about the transmission line. The radiating aperture can be placed at various angles along a transmission line with varying distances from the transmission line center. In some embodiments, an aperture can be tuned electrically using components placed in aperture region.

In some embodiments, a radiating device can include a planar shape or form factor. However, a radiating device is not restricted to a planar shape or form factor. In some embodiments, because a radiating uses an aperture or multiple apertures placed along the length of the transmission line, the device can be bent in two or three dimensions and still perform its detection and characterization functions as intended. Moreover, the device can be composed of flexible material, so that the device retains its function while bending. This feature can expand the breadth of the device to wearable and/or bendable embodiments.

In some embodiments, measurement of a sample can be performed by adding input and/or output RF connectors to interfaces one and two of a transmission line. This can allow a device to be connect to input and output interfaces of a network analyzer that is capable of generating and measuring a wide range of frequencies. In some embodiments, various biological, organic chemical, inorganic chemical, viral, bacterial, etc. samples in solid, liquid, or gas form can be targeted over multiple frequency bands through a single set up.

In some embodiments, a radiating device and associated techniques use RF measurements to characterize a sample while keeping the sample external to the detector, and not enclosing or attaching to the sample. In some embodiments, external sample characterization can be achieved using electromagnetic energy that travels into a sample placed on the surface of the sample, instead of characterizing the sample by transmitting through it. In some embodiments, an aperture on a transmission line is a gateway to radiating electromagnetic energy. This property can be tuned through aperture dimensions, count, features, and/or additional components.

In some embodiments, a radiating device can include a variety of types of transmission lines. As such, a radiating device is not limited to a single type of transmission line and has the flexibility to leverage advantageous properties of multiple transmission line types. In some embodiments, broadband transmission lines, such as microstrip or coaxial lines can be used for ultrabroad sample characterization. In some embodiments, a radiating device enables a single device to characterize an array of various biological, organic chemical, inorganic chemical, viral, bacterial, etc. samples in solid, liquid, or gas form across the electromagnetic frequency spectrum.

In some embodiments, various biological, organic chemical, inorganic chemical, viral, bacterial, etc. samples in solid, liquid, or gas form response through an aperture can be detected using a one-port transmission line with a properly terminated second port. A sample can also be characterized using a two-port transmission line. In some embodiments, a port can refer to input and/or output interfaces. In some embodiments, multiple signals can be injected independently from each interface.

In some embodiments of operating a radiating device, the device senses an external sample using an electromagnetic signal. The radiating aperture can receive an electromagnetic input signal, then the radiating aperture can radiate the electromagnetic signal into an external sample, at which point the electromagnetic signal is modified by the external sample. Then the modified electromagnetic signal can be collected from the radiating aperture. In such a manner, a radiating field from the radiating aperture non-destructively and non-invasively senses at least a portion of an external sample located within the range of the radiating field, wherein the external sample can be exposed directly to said radiating field, or the external sample can be completely enclosed within a separating medium, or the external example can be partially enclosed with the separating medium.

In some embodiments, additional peripheral elements can be used to interface a radiating aperture with elements outside the device. When such peripheral elements are involved, the device can operate in essentially the same manner. For example, electromagnetic energy (also referred to as an electromagnetic signal) is first transmitted into an input interface from an external source. The electromagnetic signal can then travel along an input transmission line towards a radiating aperture. Next, the signal can radiate from the aperture into an external sample, where the signal interacts with the external sample and is modified by the properties of the external sample. The modified signal can then travel away from the aperture along the output transmission line to an output interface. Next, the signal can exit the output interface where it is recorded by an external measuring device, and a plurality of material properties of the external sample are recorded. The external sample that is placed directly on top of the aperture may be enclosed within some container or it may be not enclosed. The device can sense and characterize the external sample whether it is enclosed or not enclosed. An input source and/or output measuring device can be used to stimulate and/or characterize the electromagnetic energy used in this device.

Figure 33:
FIG. 33 illustrates a side and proximal end perspective view of an example sensor in accordance with one or more embodiments of the present disclosure.
Figure 34:
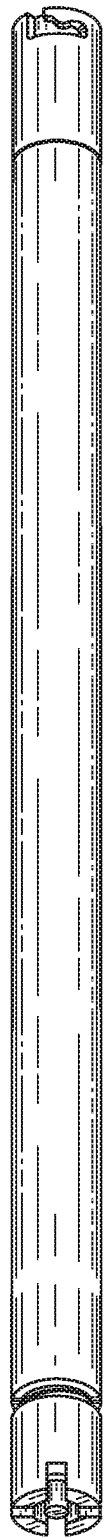
FIG. 34 illustrates a side and distal end perspective view of the example sensor of FIG. 33 in accordance with one or more embodiments of the present disclosure.
Figure 35:
FIG. 35 illustrates a side view of the example sensor of FIG. 33.
Figure 36:
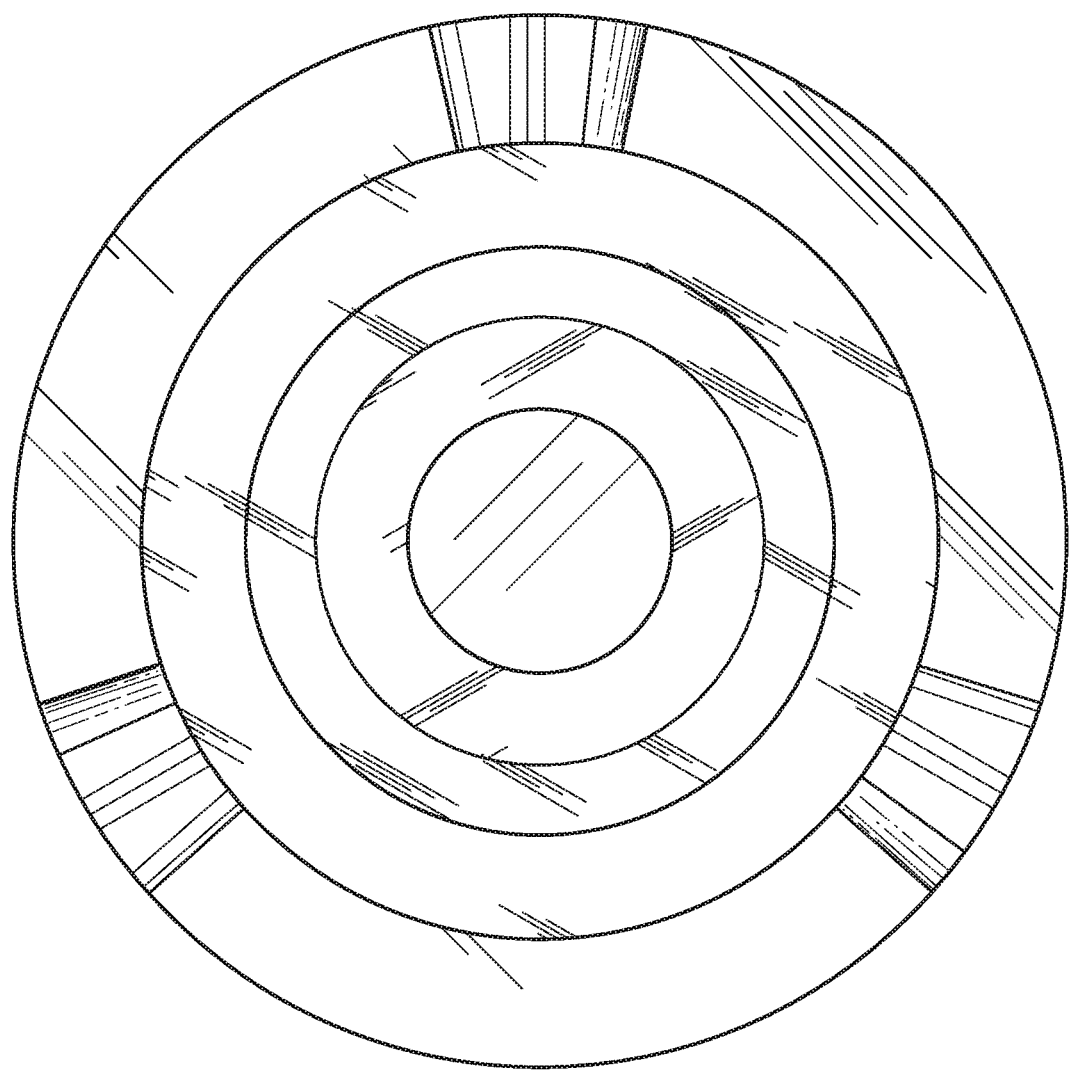
FIG. 36 illustrates a proximal end view of the example sensor of FIG. 33.
Figure 37:
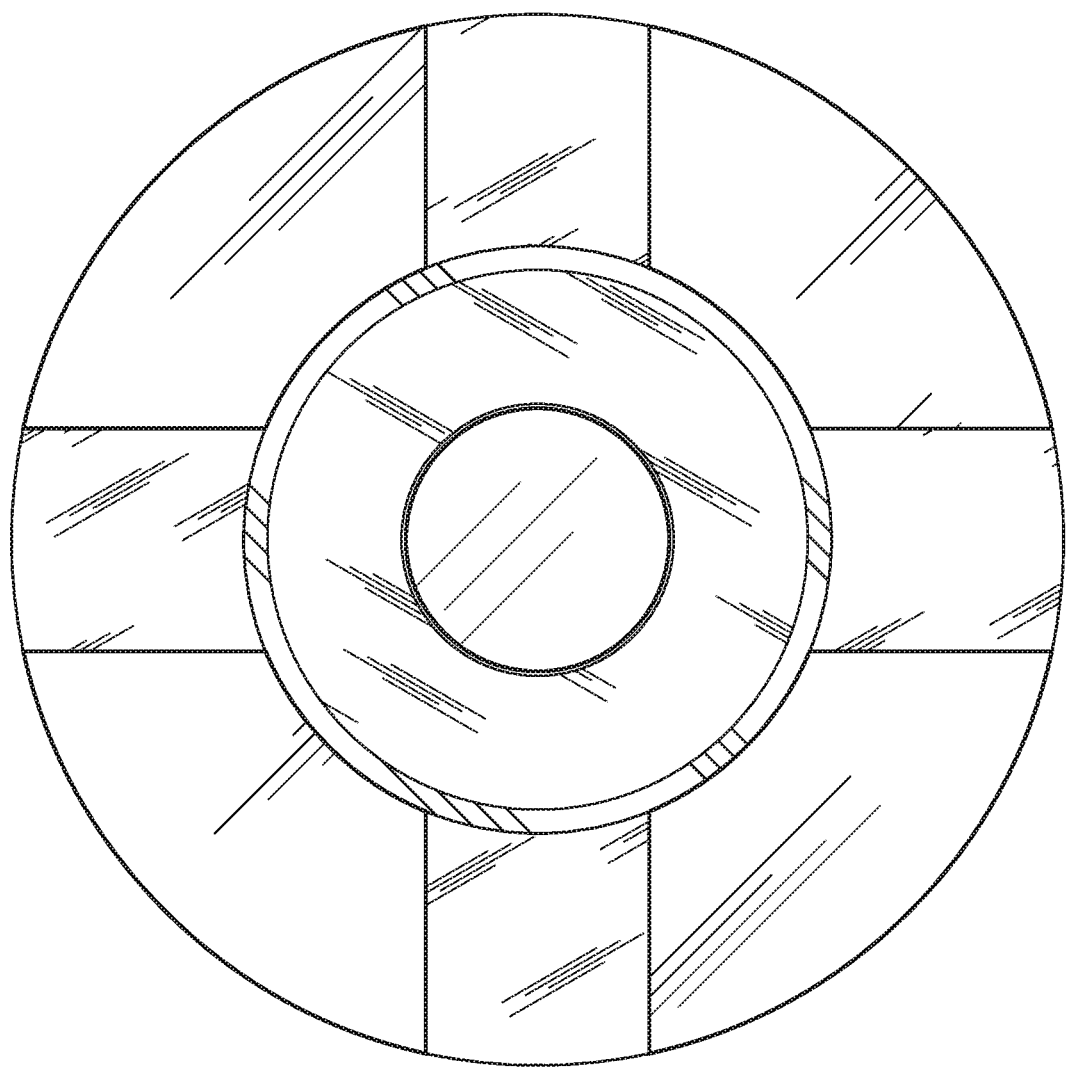
FIG. 37 illustrates a distal end view of the example sensor of FIG. 33.

FIG. 33 illustrates a side and proximal end perspective view of an example sensor in accordance with one or more embodiments of the present disclosure. FIG. 34 illustrates a side and distal end perspective view of the example sensor of FIG. 33 in accordance with one or more embodiments of the present disclosure. FIG. 35 illustrates a side view of the example sensor of FIG. 33. FIG. 36 illustrates a proximal end view of the example sensor of FIG. 33. FIG. 37 illustrates a distal end view of the example sensor of FIG. 33. The sensor of FIGS. 33-37 includes certain inventive design aspects and features. For example, although the illustrations of FIGS. 33-37 are presented using solid lines, it should be understood that the inventive design features shown in FIGS. 33-37 can relate to any portion thereof. Therefore, in design illustrations relating to the embodiment of FIGS. 33-37, any of the illustrated lines may be represented by dashed lines in accordance with the scope of the present disclosure.

Additional Features and Embodiments

The above description of embodiments of the disclosure is not intended to be exhaustive or to limit the disclosure to the precise form disclosed above. While specific embodiments, and examples, are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

Certain terms of location are used herein with respect to the various disclosed embodiments. Although certain spatially relative terms, such as "outer," "inner," "upper," "lower," "below," "above," "vertical," "horizontal," "top," "bottom," and similar terms are used herein to describe a spatial relationship of one device/element or anatomical structure relative to another device/element or anatomical structure, it is understood that these terms are used herein for ease of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited. In some contexts, description of an operation or event as occurring or being performed "based on," or "based at least in part on," a stated event or condition can be interpreted as being triggered by or performed in response to the stated event or condition.

With respect to the various methods and processes disclosed herein, although certain orders of operations or steps are illustrated and/or described, it should be understood that the various steps and operations shown and described may be performed in any suitable or desirable temporal order. Furthermore, any of the illustrated and/or described operations or steps may be omitted from any given method or process, and the illustrated/described methods and processes may include additional operations or steps not explicitly illustrated or described.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

Unless the context clearly requires otherwise, throughout the description and the claims, the terms "comprise," "comprising," "have," "having," "include," "including," and the like are to be construed in an open and inclusive sense, as opposed to a closed, exclusive, or exhaustive sense; that is to say, in the sense of "including, but not limited to."

The word "coupled", as generally used herein, refers to two or more elements that may be physically, mechanically, and/or electrically connected or otherwise associated, whether directly or indirectly (e.g., via one or more intermediate elements, components, and/or devices. Additionally, the words "herein," "above," "below," and words of similar import, when used in this application, shall refer to this application as a whole, including any disclosure incorporated by reference, and not to any particular portions of the present disclosure. Where the context permits, words in present disclosure using the singular or plural number may also include the plural or singular number, respectively.

The word "or" in reference to a list of two or more items, that word covers all of the following interpretations of the word: any of the items in the list, all of the items in the list, and any combination of the items in the list. Furthermore, as used herein, the term "and/or" used between elements (e.g., between the last two of a list of elements) means any one or more of the referenced/related elements. For example, the phrase "A, B, and/or C" means "A," "B," "C," "A and B," "A and C," "B and C," or "A, B, and C."

As may be used herein, the terms "substantially" and "approximately" provides an industry-accepted tolerance for its corresponding term and/or relativity between items. For some industries, an industry-accepted tolerance is less than one percent, while for other industries, the industry-accepted tolerance may be 10 percent or more. Other examples of industry-accepted tolerances range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the terms "processing circuitry," "processing circuit," "processor," "processing module," and/or "processing unit" may refer to a single processing device or a plurality of processing devices. Such a processing device may comprise a chip, die (e.g., semiconductor die including come or more active and/or passive devices and/or connectivity circuitry), microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be remotely located (e.g., cloud computing via indirect coupling via a local area network and/or a wide area network). Further note that if the processing module, module, processing circuit, processing circuitry and/or processing unit implements one or more of its functions via a hardware and/or software state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from Figure to figure, the embodiments may incorporate the same or similarly named functions, steps, modules, etc. that may use the same, related, or unrelated reference numbers. The relevant features, elements, functions, operations, modules, etc. may be the same or similar functions or may be unrelated.

Unless specifically stated to the contra, signals to, from, and/or between elements in a Figure of any of the Figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

What is claimed is:

1. A sensing system, comprising:
   a sensor comprising:
   an outer conductor comprising a first outer conductor portion and a second outer conductor portion;
   a transmitting portion comprising the first outer conductor portion and a dielectric material disposed at least partially within the first outer conductor portion; and
   a resonating portion comprising the second outer conductor portion and a resonator cavity formed by the second outer conductor portion; and
   control circuitry electrically coupled to the sensor, the control circuitry being configured to:
   transmit a first signal into a liquid sample using the sensor while the resonating portion contacts the liquid sample;
   receive a first reflected signal; and
   determine a resonant frequency associated with the resonating portion based at least in part on the first reflected signal.

2. The sensing system of claim 1, wherein the control circuitry is further configured to determine a concentration of a constituent in the liquid sample based at least in part on the resonant frequency.

3. The sensing system of claim 2, wherein the constituent comprises glucose, lactase, or alcohol.

4. The sensing system of claim 1, wherein the control circuitry is further configured to:
   transmit a second signal into the liquid sample using the sensor;
   receive a second reflected signal, and
   determine the resonant frequency based at least in part on the first reflected signal and the second reflected signal.

5. The sensing system of claim 1, wherein the control circuitry is configured to determine the resonant frequency based on one or more of an amplitude of the first reflected signal and a phase of the first reflected signal.

6. The sensing system of claim 1, wherein the transmitting portion is proximate to the control circuitry and the resonating portion is distal to the control circuitry.

7. The sensing system of claim 1, further comprising a container structure configured to receive the sensor, wherein the container structure includes an opening and a semipermeable membrane associated with the opening.

8. The sensing system of claim 1, further comprising an interface configured to communicate data based on at least one of the first signal, the first reflected signal, and the resonant frequency to a computing device that is communicatively coupled to the interface.

9. A sensor comprising:
   an outer conductor comprising a first outer conductor portion and a second outer conductor portion;
   a transmitting portion comprising the first outer conductor portion and an interior portion defined at least in part by the first outer conductor portion; and
   a resonating portion comprising the second outer conductor portion and a resonator cavity formed by the second outer conductor portion, wherein the second outer conductor portion has at least one slot formed therein; wherein
   the at least one slot is configured to allow for flow of a liquid sample into or out of the resonator cavity when the resonating portion is disposed at least partially therein; and
   the resonator cavity is fluidly isolated from the interior portion of the transmitting portion.

10. The sensor of claim 9, further comprising an electrically absorptive material disposed at an interface between the interior portion of the transmitting portion and the resonator cavity of the resonating portion.

11. The sensor of claim 10, wherein the sensor has an elongated form and further comprises an inner conductor that extends along a center axis of the sensor.

12. The sensor of claim 11, wherein the absorptive material is disposed between the first outer conductor portion and the inner conductor.

13. The sensor of claim 11, wherein the inner conductor extends through both the transmitting and the resonating portions.

14. The sensor of claim 9, wherein the at least one slot extends axially from a distal end of the resonating portion.

15. The sensor of claim 9, wherein the sensor has a cylindrical elongated form.

16. A method of using a sensor, the sensor comprising an outer conductor comprising a first outer conductor portion and a second outer conductor portion, a transmitting portion comprising the first outer conductor portion and a dielectric material disposed at least partially within the first outer conductor portion, and a resonating portion comprising the second outer conductor portion and a resonator cavity formed by the second outer conductor portion, the method comprising:

providing a volume of a liquid sample;
   causing the resonating portion to contact the liquid sample;
   transmitting, using the sensor, a signal into the liquid sample.
   receiving a reflected signal; and
   determining, by control circuitry that is coupled to the sensor, a resonant frequency associated with the resonating portion based at least in part on the reflected signal.

17. The method of claim 16, wherein:
   the transmitting includes transmitting multiple signals having different frequencies;
   the receiving includes receiving multiple reflected signals; and
   the determining includes determining the resonant frequency based at least in part on the multiple reflected signals.

18. The method of claim 16, further comprising determining, by the control circuitry, a concentration of a constituent in the liquid sample based at least in part on the resonant frequency.

19. A sensing system, comprising:
   a sensor comprising:
      an outer conductor comprising a first outer conductor portion and a second outer conductor portion;
      a transmitting portion comprising the first outer conductor portion and a dielectric material disposed at least partially within the first outer conductor portion; and
      a resonating portion comprising the second outer conductor portion and a resonator cavity formed by the second outer conductor portion; and
   control circuitry electrically coupled to the sensor, the control circuitry being configured to:
      transmit a first signal into a liquid sample using the sensor while the resonating portion contacts at least a portion of the liquid sample;
      receive a first reflected signal; and
      determine a magnitude, attenuation, or phase offset associated with the first reflected signal.

20. The sensing system of claim 19, wherein the control circuitry is further configured to determine a concentration of a constituent in the liquid sample based at least in part on the magnitude, attenuation, or the phase offset.

21. The sensing system of claim 20, wherein the constituent comprises glucose, lactase, or alcohol.

22. The sensing system of claim 20, wherein the sensor further comprises an inner conductor comprising a first inner conductor portion and a second inner conductor portion, the first inner conductor portion is part of the transmitting portion of the sensor, the second inner conductor portion is part of the resonating portion of the sensor, and the dielectric material is between the first outer conductor portion and the first inner conductor portion.

* * * * *